US010364457B2

(12) United States Patent
Wassie et al.

(10) Patent No.: US 10,364,457 B2
(45) Date of Patent: *Jul. 30, 2019

(54) NANOSCALE IMAGING OF PROTEINS AND NUCLEIC ACIDS VIA EXPANSION MICROSCOPY

(71) Applicants: Massachusetts Institute of Technology, Cambridge, MA (US); President and Fellows of Harvard College, Cambridge, MA (US)

(72) Inventors: Asmamaw Wassie, Cambridge, MA (US); Fei Chen, Cambridge, MA (US); Edward Stuart Boyden, Chestnut Hill, MA (US); Shahar Alon, Cambridge, MA (US); George Church, Brookline, MA (US); Evan Daugharthy, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/229,539

(22) Filed: Aug. 5, 2016

(65) Prior Publication Data
US 2017/0067096 A1 Mar. 9, 2017

Related U.S. Application Data

(60) Provisional application No. 62/202,421, filed on Aug. 7, 2015.

(51) Int. Cl.
*C12Q 1/6841* (2018.01)
*C12Q 1/6806* (2018.01)
*G01N 1/36* (2006.01)

(52) U.S. Cl.
CPC ......... *C12Q 1/6841* (2013.01); *C12Q 1/6806* (2013.01); *G01N 1/36* (2013.01); *G01N 2001/364* (2013.01)

(58) Field of Classification Search
CPC .. C12Q 1/6841; G01N 33/543; B01J 37/0018
See application file for complete search history.

(56) References Cited

U.S. PATENT DOCUMENTS

| 5,952,232 A | 9/1999 | Rothman |
| 6,107,081 A | 8/2000 | Feeback et al. |
| (Continued) | | |

FOREIGN PATENT DOCUMENTS

| JP | 2005291759 A | 10/2005 |
| JP | 2009191125 | 8/2009 |
| (Continued) | | |

OTHER PUBLICATIONS

Chen et al, Nanoscale imaging of RNA with expansion microscopy, 2016, Nature methods, 13, 679-684, Post art. (Year: 2016).*
(Continued)

*Primary Examiner* — Narayan K Bhat
(74) *Attorney, Agent, or Firm* — Elmore Patent Law Group, P.C.; Joseph Zucchero; Carolyn Elmore

(57) ABSTRACT

The invention enables in situ genomic and transcriptomic assessment of nucleic acids to be conducted in biological specimens that have been physically expanded. The invention leverages the techniques for expansion microscopy (ExM) to provide new methods for in situ genomic and transcriptomic assessment of nucleic in a new process referred to herein as "expansion fluorescent in situ hybridization" (ExFISH).

13 Claims, 46 Drawing Sheets
(37 of 46 Drawing Sheet(s) Filed in Color)
Specification includes a Sequence Listing.

(56) References Cited

U.S. PATENT DOCUMENTS

| | | |
|---|---|---|
| 6,271,278 B1 | 8/2001 | Park et al. |
| 6,287,870 B1 | 9/2001 | Wardlaw et al. |
| 2002/0176880 A1 | 11/2002 | Cruise et al. |
| 2003/0120231 A1 | 6/2003 | Wang et al. |
| 2005/0090016 A1 | 4/2005 | Rich et al. |
| 2006/0000767 A1* | 1/2006 | Trauger ............... B09C 1/002 210/503 |
| 2006/0115146 A1 | 6/2006 | Ogura et al. |
| 2008/0261834 A1* | 10/2008 | Simon .................. C09K 8/516 507/221 |
| 2009/0011420 A1 | 1/2009 | Barron et al. |
| 2009/0191627 A1 | 7/2009 | Fadeev et al. |
| 2009/0241681 A1 | 10/2009 | Machauf et al. |
| 2010/0041128 A1 | 2/2010 | Banes et al. |
| 2010/0068725 A1 | 3/2010 | Armbruster et al. |
| 2010/0096334 A1* | 4/2010 | Edmiston ............... B01J 20/02 210/691 |
| 2011/0070604 A1 | 3/2011 | Gimzewski et al. |
| 2011/0091922 A1 | 4/2011 | Krishnan et al. |
| 2012/0184670 A1 | 7/2012 | Kobayashi et al. |
| 2012/0220478 A1 | 8/2012 | Shaffer |
| 2013/0045503 A1 | 2/2013 | Miyawaki et al. |
| 2013/0203605 A1 | 8/2013 | Shendure et al. |
| 2016/0116384 A1 | 4/2016 | Boyden et al. |
| 2016/0252528 A1 | 9/2016 | Sangaralingham et al. |
| 2016/0304952 A1 | 10/2016 | Boyden et al. |
| 2016/0305856 A1 | 10/2016 | Chen et al. |
| 2017/0067096 A1 | 3/2017 | Wassie et al. |
| 2017/0081489 A1 | 3/2017 | Boyden et al. |
| 2017/0089811 A1 | 3/2017 | Chen et al. |

FOREIGN PATENT DOCUMENTS

| | | |
|---|---|---|
| JP | 2014005231 | 6/2012 |
| WO | 200008212 A1 | 2/2000 |
| WO | 2010048605 A1 | 4/2010 |
| WO | 2012142664 A1 | 10/2012 |
| WO | 2014025392 A1 | 2/2014 |
| WO | 2014152984 A1 | 9/2014 |
| WO | 2015127183 A2 | 8/2015 |
| WO | 2017027367 A1 | 2/2017 |
| WO | 2017027368 A1 | 2/2017 |
| WO | 2017079406 A1 | 5/2017 |

OTHER PUBLICATIONS

Freifeld et al, Expansion microscopy of zebrafish for neuroscience and developmental biology studies, 2017, PNAS, E10799-E10808, Post art (Year: 2017).*

Chen et al, Nanoscale imaging of RNRNA with expansion microscopy, 2016, Nature Methods, 2016, 13, 679-684, Post Art. (Year: 2016).*

Chen, F., et al., "Expansion Microscopy," Science, vol. 347, No. 6221, p. 543, Jan. 2015.

Chen, F., et al., "Nanoscale Imaging of RNA with Expansion Microscopy," HHS Public Access Author Manuscript, vol. 13(8): pp. 679-684 (Aug. 2016).

Chen F., et al., "Expansion microscopy", Science 347(6221); pp. 543-548 (2015).

Femino, A., et al., "Visualization of Single RNA Transcripts in Situ," Science, vol. 280; pp. 585-590 (1998).

Levsky, J., et al., "Fluorescence in situ hybridization: past, present and future," Journal of Cell Science, 116, 2833-2838 (2003).

Raj, A., et al., Imaging individual mRNA molecules using multiple singly labeled probes. Nat. Methods 5(10: pp. 887-889 (2008).

Choi, H., et al., "Programmable in situ amplification for multiplexed imaging of mRNA expression," Nature Biotechnology, 28(11): pp. 1208-1212 (2010).

Choi, H., et al., "Next-Generation in Situ Hybridization Chain Reaction: Higher Gain, Lower Cost, Greater Durability," ACS Nano 8(5): pp. 4284-4294 (2014).

Cajigas, I. et al. "The local transcriptome in the synaptic neuropil revealed by deep sequencing and high-resolution imaging," Neuron 74, pp. 453-466 (2012).

Wang, F., et al., "RNAscope: A novel in situ RNA analysis platform for formalin-fixed, paraffin-embedded tissues," Journal of Molecular Diagnostics, vol. 14(1): pp. 22-29 (2012).

Tillberg, P., et al., "Protein-Retention Expansion Microscopy of Cells and Tissues Labeled Using Standard Fluorescent Proteins and Antibodies," Nature Biotechnology vol. 34(9): pp. 987-995 (2016).

Chozinski, T., et al., "Expansion microscopy with conventional antibodies and fluorescent proteins,". Nature Methods, vol. 13(6): pp. 485-491 (2016).

Engreitz, J., et al. "The Xist lncRNA exploits three-dimensional genome architecture to spread across the X chromosome," Science 341,1237973 (2013).

Panning, B., et al., "X chromosome Inactivation is Mediated by by Xist RNA stabilization," Cell. vol. 90, 907-16 (1997).

Plath, K., et al., "Xist RNA and the mechanism of X chromosome inactivation," Annu. Rev. Genet. 36, 233-78 (2002).

Mito, M., et al., "Simultaneous multicolor detection of RNA and proteins using super-resolution microscopy," Methods (2015). doi:10.1016/j.ymeth.2015.11.007.

Clemson, C., et al., "An architectural role for a nuclear noncoding RNA: NEAT1 RNA is essential for the structure of paraspeckles," Molecular Cell, 33, 717-26 (2009).

Lieberman-Aiden, E., et al., "Comprehensive mapping of long-range interactions reveals folding principles of the human genome," Science 326, pp. 289-293 (2009).

Lubeck, E., et al., "Single-cell systems biology by super-resolution imaging and combinatorial labeling," Nature Methods, vol. 9, 743-8 (2012).

Lubeck, E., et al., "Single-cell in situ RNA profiling by sequential hybridization," Nature Methods, vol. 11(4): pp. 360-361 (2014).

Chen, K., et al., "Spatially resolved, highly multiplexed RNA profiling in single cells," Science. vol. 348(6233), aaa6090-aaa6090 (2015).

Beliveau, B., et al. "Versatile design and synthesis platform for visualizing genomes with Oligopaint FISH probes," PNAS, vol. 109(52): pfa. 21301-21306 (2012).

Feng, G., et al., "Imaging neuronal subsets in transgenic mice expressing multiple spectral variants of GFP," Neuron 28. pp. 41-51 (2000).

Lein, E., et al. "Genome-wide atlas of gene expression in the adult mouse brain," Nature, vol. 445, 168-76 (2007).

Huisken, J., et al., "Optical Sectioning Deep Inside Live Embryos by Selective Plane Illumination Microscopy," Science. vol. 305, 1007-1009 (2004).

Batish, M., et al., "Neuronal mRNAs Travel Singly into Dendrites," PNAS, vol. 109(12): pp. 4645-4650 (2012).

Cabili, M., et al., "Localization and abundance analysis of human lncRNAs at single-cell and single-molecule resolution," Genome Biology, vol. 16(20) (2015).

Zhang, D., et al., "Dynamic DNA nanotechnology using strand-displacement reactions," Nature Chemistry, vol. 3, pp. 103-113 (2011).

Lee, J., et al., "Highly Multiplexed Subcellular RNA Sequencing in Situ," Science, vol. 343, pp. 1360-1363 (2014).

Ke, R., et al., "In situ sequencing for RNA analysis in preserved tissue and cells," Nature Methods, vol. 10(9): pp. 857-860 (2013).

Shah, S., et al., "Single-molecule RNA detection at depth via hybridization chain reaction and tissue hydrogel embedding and clearing," Development in Review, (2016).

Bruchez, M., et al., "Semiconductor nanocrystals as fluorescent biological labels," Science, vol. 281, pp. 2013-2016 (1998).

Fouz, M., et al., "Bright Fluorescent Nanotags from Bottlebrush Polymers with DNA-Tipped Bristles," ACS Central Science, vol. 1, pp. 431-438 (2015).

Steward, O., et al., Synaptic activation causes the mRNA for the leg Arc to localize selectively near activated postsynaptic sites on dendrites. Neuron, vol. 21, pp. 741-751 (1998).

Buckley, P., et al., "Cytoplasmic Intron Sequence-Retaining Transcripts Can Be Dendritically Targeted via ID Element Retrotransposons," Neuron, vol. 69, pp. 877-884 (2011).

(56) References Cited

OTHER PUBLICATIONS

Steward, O., et al., "Compartmentalized synthesis and degradation of proteins in neurons," Neuron, vol. 40, pp. 347-359 (2003).
Buxbaum, A., et al., Single-Actin mRNA Detection in Neurons Reveals a Mechanism for Regulating Its Translatability, Science, vol. 343, pp. 419-422 (2014).
Jung, H., et al., "Axonal mRNA localization and local protein synthesis in nervous system assembly, maintenance and repair," Nat. Rev. Neurosci., vol. 13(5): pp. 308-324 (2012).
Raj, A., et al., "Detection of individual endogenous RNA transcripts in situ using multiple singly labeled probes," Methods in Enzymology, vol. 472, pp. 365-386, (Elsevier Inc., 2010).
Schindelin J., et al., "Fiji: an open-source platform for biological-image analysis," Nature Methods, vol. 9, pp. 676-682 (2012).
Thevenaz, P., et al., "A pyramid approach to subpixel registration based on intensity," IEEE Trans. Image Process. 7,27-41 (1998).
Office Action dated Apr. 4, 2018 from U.S. Application No. 14/627,310, filed Feb. 20, 2015.
Sniegowski, J. A. et al., "Maturation efficiency, trypsin sensitivity, and optical properties of Arg96, Glu222, and Gly67 variants of green fluorescent protein", Biochem. Biophys. Res. Commun., 332, 2005, 657-63.
Strack, R., "Imaging Bigger is Better for Super-Resolution", Nature Methods, 12(13), Mar. 1, 2015, 169.
Subach, F. V. et al., "Bright monomeric photoactivatable red fluorescent protein for twocolor super-resolution sptPALM of live cells", J. Am. Chem. Soc., 132, 2010, 6481-91.
Subach, O. M. et al., "An Enhanced Monomeric Blue Fluorescent Protein with the High Stability of the Chemical Chromophore", PLoS One, 6, 2011, e28674.
Van Vliet, et al., "The Biomechanics Toolbox: Experimental Approaches for Living Cells and Biomolecules," Acta Materialia, vol. 51, pgs. 5881-5905 (Aug. 2003).
Vedaldi, A. et al., Vlfeat. In Proc. Int. Conf. Multimed. —MM '10 1469 (ACM Press, 2010). doi: 10.1145/1873951.1874249.
Wachter, R. M. et al., "Sensitivity of the yellow variant of green fluorescent protein to halides and nitrate", Curr. Biol., 9, 1999, R628—R629.
Wu, C. C. et al., "A method for the comprehensive proteomic analysis of membrane proteins", Nat. Biotechnol., 21, 2003, 532-8.
Zimmerman, T. A. et al., "Adapting the stretched sample method from tissue profiling to imaging", Proteomics, 8, 2008, 3809-3815.
Al, H. et al., "Exploration of new chromophore structures leads to the identification of improved blue fluorescent proteins", Biochemistry, 46, 2007, 5904-10.
Bates M. et al., "Multicolor super-resolution imaging with photoswitchable fluorescent probes", Science, 317, 2007, 1749-1753.
Bokman, S.H. et al., "Renaturation of Aequorea ree-fluorescent protein", Biochem. Biophys. Res. Commun., 101, 1981, 1372-80.
Bossi, M. et al., "Multicolor far-field fluorescence nanoscopy through isolated detection of distinct molecular species", Nano Lett., 8, 2008, 2463-8.
Buenrostro, J.D. et al., "ATAC-seq: A Method for Assaying Chromatin Accessibility Genome-Wide : ATAC-seq for Assaying Chromatin Accessibility", In: "Current Protocols in Molecular Biology", Willey, New York, NY, Jan. 5, 2015.
Cai, et al., Nat Meth., 10, 2013, 540-547.
Carpenter, A. E. et al., "CellProfiler: image analysis software for identifying and quantifying cell phenotypes", Genome Biol., 7, 2006, R100.
Chen, F. et al., "Supplementary Material for Expansion Microscopy", Science, 347(6221), Jan. 15, 2015, 543-548.
Chu, J. et al., "Non-invasive intravital imaging of cellular differentiation with a bright redexcitable fluorescent protein", Nat. Methods, 11, 2014, 572-8.
Cormack, B. P. et al., "FACS-optimized mutants of the green fluorescent protein (GFP)",Gene, 173, 1996, 33-8.
Cubitt, A. B. et al., "Understanding structure-function relationships in the Aequorea victoria green fluorescent protein", Methods Cell Biol., 58, 1999, 19-30.

Dedecker, P. et al., "Localizer: fast, accurate, open-source, and modular software package for superresolution microscopy", J. Biomed. Opt., 17, 2012, 126008.
Edelstein, A. et al., "Computer control of microscopes using µManager", Curr. Protoc. Mol. Biol. Chapter 14, Unit14.20, 2010.
English, B. P. et al., "A three-camera imaging microscope for high-speed singlemolecule tracking and super-resolution imaging in living cells", in SPIE Nanosci. + Eng. (Mohseni, H., Agahi, M. H. & Razeghi, M.) 955008 (International Society for Optics and Photonics, 2015). doi:10.1117/12.2190246.
Filonov, G. S. et al., "Bright and stable near-infrared fluorescent protein for in vivo imaging", Nat. Biotechnol., 29, 2011, 757-61.
Goedhardt, J. et al., "Structure-guided evolution of cyan fluorescent proteins towards a quantum yield of 93%", Nat. Commun., 3, 2012, 751.
Griesbeck, 0. et al., "Reducing the environmental sensitivity of yellow fluorescent protein. Mechanism and applications", J. Biol. Chem., 276, 2001, 29188-9.
Gurskaya, N. G. et al., "Engineering of a monomeric green-to-red photoactivatable fluorescent protein induced by blue light", Nat. Biotechnol., 24, 2006, 461-5.
Habuchi, S. et al., "mKikGR, a monomeric photoswitchable fluorescent protein", PLoS One, 3, 2008, e3944.
Hackstadt, T., "Steric hindrance of antibody binding to surface proteins of Coxiella burnetti by phase I lipopolysaccharide", Infect Immun, 56, 1998, 802-807.
Heim, R. et al., "Engineering green fluorescent protein for improved brightness, longer wavelengths and fluorescence resonance energy transfer", Curr. Biol., 6, 1996, 178-82.
Heim, R. et al., "Wavelength mutations and posttranslational autoxidation of green fluorescent protein", Proc. Natl. Acad. Sci. U.S.A., 91, 1994, 12501-4.
Huang, B. et al., "Whole-cell 3D Storm reveals interactions between cellular structures with nanometer-scale resolution", Nat. Methods, 5, 2008, 1047-1052.
Hunt, et al., "High temperature antigen retrieval and loss of nuclear morphology: a comparison of microwave\rand autoclave techniques", J. Clin. Pathol. 49, 1996, 767-770.
Jekel, P. A. et al., "Use of endoproteinase Lys-C from Lysobacter enzymogenes in protein sequence analysis", Anal. Biochem., 134, 1983, 347-354.
Jimenez, N. et al., "A Novel Approach for Intracellular 3D Immuno-Labeling for Electron Tomography"Traffic, 13, 2012, 926-933.
Kakimoto, K. et al., "Hypothesis for the mechanism for heat-induced antigen retrieval occurring on fresh frozen sections without formalin-fixation in immunohistochemistry", J Mol Histol., 39, 2008, 389-399.
Kaur, et al., Biochemistry 45, 2006, 7347-7355.
Kroon, D.-J , "B-spline Grid, Image and Point based Registration", Matlab Cent. at <http://www.mathworks.com/matlabcentral/fileexchange/20057-b-spline-grid—image-and-point-based-registration>.
Laemmli, U. K., "Cleavage of structural proteins during the assembly of the head of bacteriophage T4", Nature, 227, 1970, 680-685.
Lam, A. J. et al., "Improving FRET dynamic range with bright green and red fluorescent proteins",Nat. Methods, 9, 2012, 1005-12.
Lee, J. et al., "Highly Multiplexed Subcellular RNA Sequencing in Situ", Duplicate - RefID 308986 Science, vol. 343, 2014, 1360-1363.
Livet, J. et al., "Transgenic strategies for combinatorial expression of fluorescent proteins in the nervous system", Nature, 450, 2007, 56-62.
Lowe, D. G. , "Distinctive Image Features from Scale-Invariant Keypoints", Int. J. Comput. Vis., 60, 2004, 91-110.
Markwardt, M. L. et al., "An improved cerulean fluorescent protein with enhanced brightness and reduced reversible photoswitching", PLoS One, 6, 2011, e17896.
Mckinney, S. A. et al., "A bright and photostable photoconvertible fluorescent protein", Nat. Methods, 6, 2009, 131-3.
Mortensen, K. I. et al., "Optimized localization analysis for singlemolecule tracking and super-resolution microscopy", Nat. Methods, 7, 2010, 377-81.

(56) References Cited

OTHER PUBLICATIONS

Nagai, T. et al., "A variant of yellow fluorescent protein with fast and efficient maturation cell-biological applications", Nat. Biotechnol., 20, 2002, 87-90.

Nagre, R. D. et al., "Thermosaline Resistant Acrylamide-Based Polyelectrolyte as Filtration Control Additive in Aqueous-Based Mud", Petroleum and Coal, vol. 56, No. 3, 2014, 222-230.

Ormo, M. et al., "Crystal structure of the Aequorea victoria green fluorescent protein", Science, 273, 1996, 1392-5.

Randall, K. J. et al., "A dual-label technique for the immunohistochemical demonstration of T-lymphocyte subsets in formalin-fixed, paraffin-embedded rat lymphoid tissue", Toxicol. Pathol., 36, 2008, 795-804.

Rego, E. H. et al., "Nonlinear structured-illumination microscopy with a photoswitchable protein reveals cellular structures at 50-nm resolution", Proc. Natl. Acad. Sci. U.S.A., 109 2012, E135-43.

Reinhart-King, C. A. et al., "Dynamics and Mechanics of EndothelialCell Spreading", Biophysical J. 89(1):, Jul. 1, 2005, 676-689.

Rose, R. et al., "Ocular ascorbate transport and metabolism", A. Comp. Physiol.,100, 1991, 273-85.

Schnell, U. et al., "Immunolabeling artifacts and the need for live-cell imaging", Nat. Methods, 9, 2012, 152-158.

Seneviratne, U. et al., "S-nitrosation of proteins relevant to Alzheimer's disease during early stages of neurodegeneration", Proc. Natl. Acad. Sci. U. S. A. 1521318113-(2016). doi:10.103/pnas.1521318113.

Shaner, N. C. et al., "Improved monomeric red, orange and yellow fluorescent proteins derived from Discosoma sp. red fluorescent protein", Nat. Biotechnol., 22 2004, 1567-72.

Shaner, N. C. et al., "Improving the photostability of bright monomeric orange and red fluorescent proteins", Nat. Methods, 5, 2008, 545-51.

Shcherbakova, D. M., "An orange fluorescent protein with a large Stokes shift for single-excitation multicolor FCCS and FRET imaging", J. Am. Chem. Soc., 134, 2012, 7913-23.

Shcherbo, D. et al., "Far-red fluorescent tags for protein imaging in living tissues", Biochem. J., 418, 2009, 567-74.

\* cited by examiner

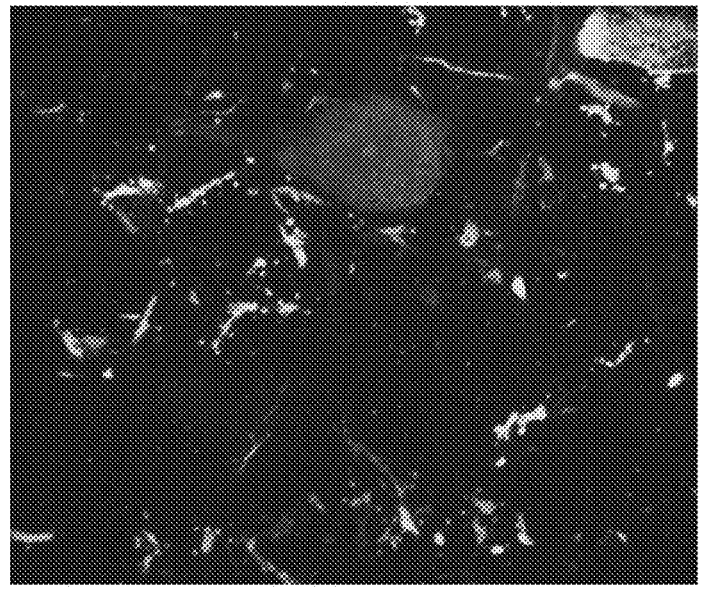
Fig. 3G(i)
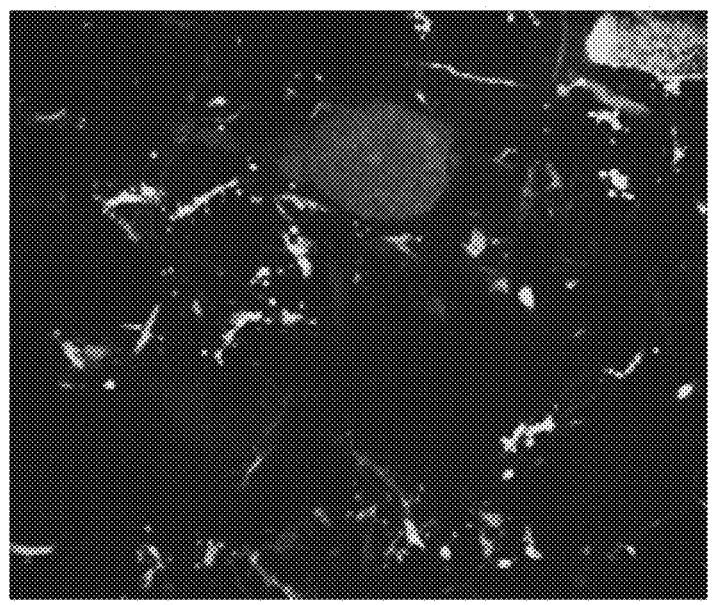
Fig. 3G(ii)

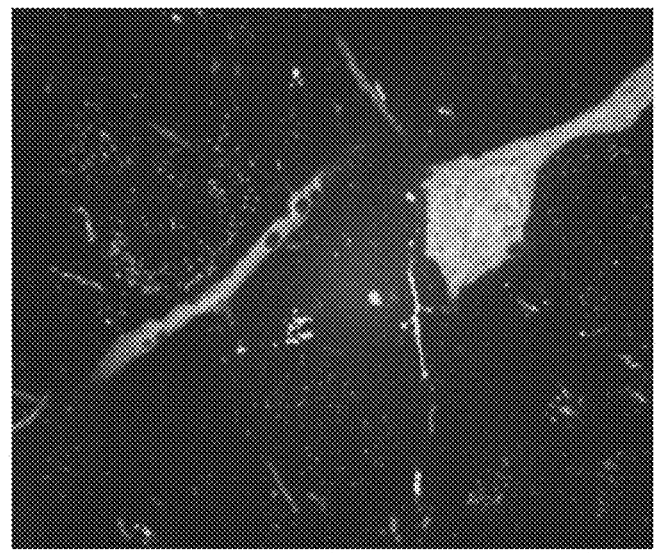
Fig. 3H(i)
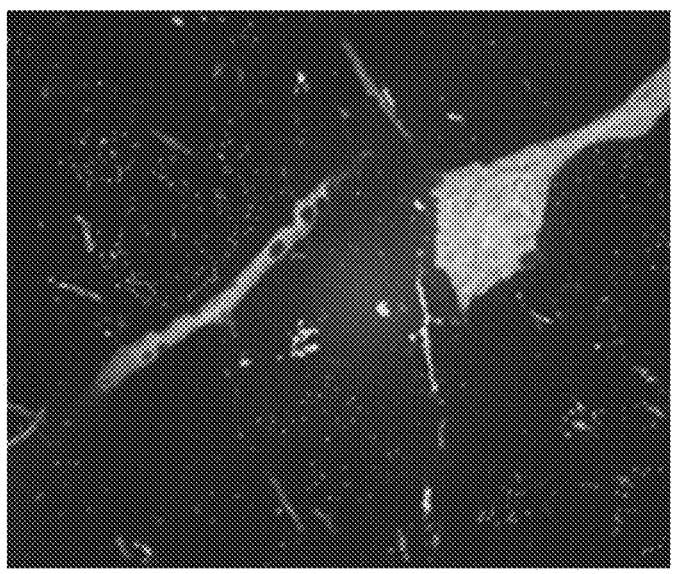
Fig. 3H(ii)

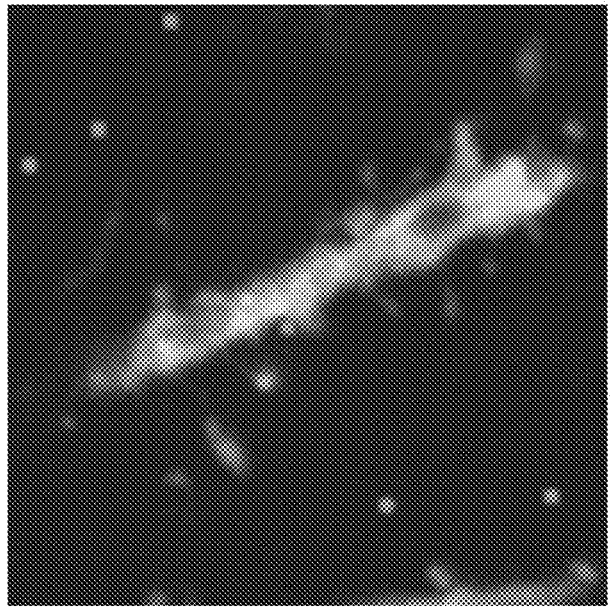
Fig. 3J(i)
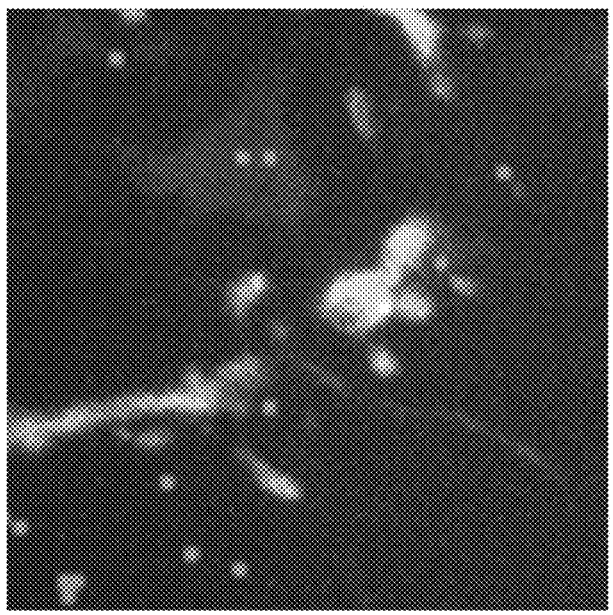
Fig. 3J(ii)

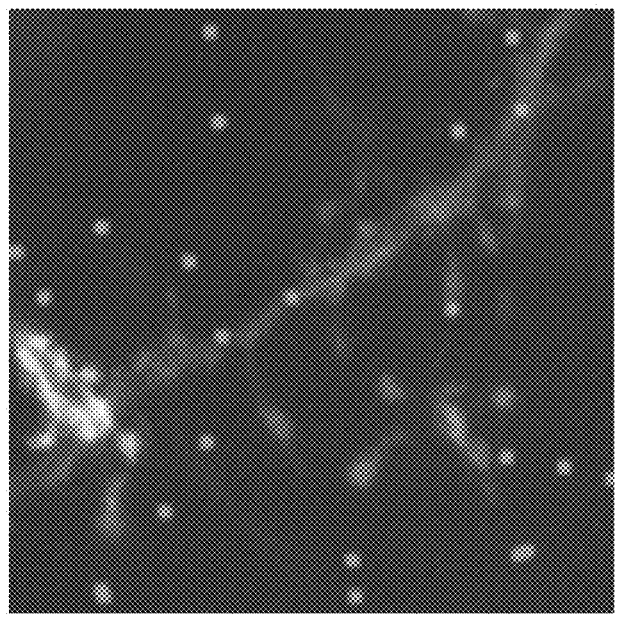
Fig. 3K(i)
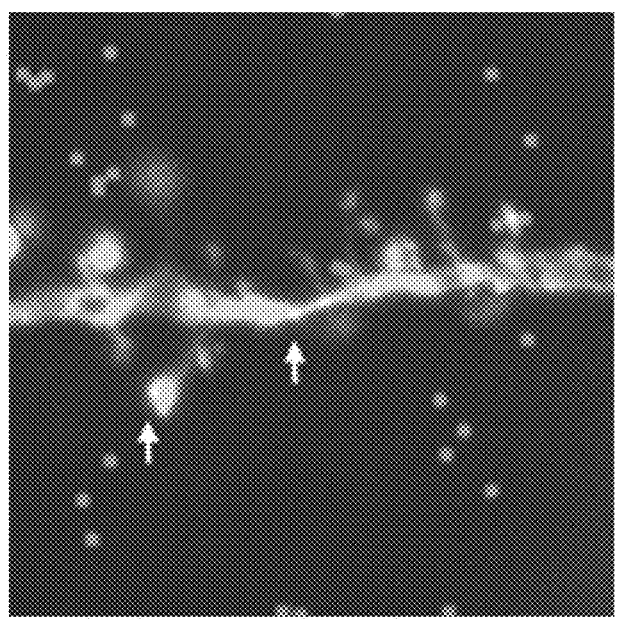
Fig. 3K(ii)

NANOSCALE IMAGING OF PROTEINS AND NUCLEIC ACIDS VIA EXPANSION MICROSCOPY

RELATED APPLICATION

This application claims the benefit of U.S. Provisional Application Ser. No. 62/202,421, filed Aug. 7, 2015, the contents of which are incorporated herein by reference in its entirety.

GOVERNMENT SUPPORT

This invention was made with government support under 5-DPI-NS087724 awarded by NIH, Hertz Foundation, ODGE Lemelson & Viterbi, 5-DPI-N S087724 awarded by NIH and NSF. The government has certain rights in the invention.

BACKGROUND OF THE INVENTION

Nanoscale-resolution imaging of RNA throughout cells, tissues, and organs is key for an understanding of local RNA processing, mapping structural roles of RNA, and defining cell types and states. However, it has remained difficult to image RNA in intact tissues with the nanoscale precision required to pinpoint associations with cellular compartments or proteins important for RNA function.

Expansion microscopy (ExM) enables imaging of thick preserved specimens with ~70 nm lateral resolution. Using ExM the optical diffraction limit is circumvented by physically expanding a biological specimen before imaging, thus bringing sub-diffraction limited structures into the size range viewable by a conventional diffraction-limited microscope. ExM can image biological specimens at the voxel rates of a diffraction limited microscope, but with the voxel sizes of a super-resolution microscope. Expanded samples are transparent, and index-matched to water, as the expanded material is >99% water. The original ExM protocol worked by labeling biomolecules of interest with a gel-anchorable fluorophore. Then, a swellable polyelectrolyte gel was synthesized in the sample, so that it incorporated the labels. Finally, the sample was treated with a nonspecific protease to homogenize its mechanical properties, followed by dialysis in water to mediate uniform physical expansion of the polymer-specimen composite. All of the chemicals required for ExM can be purchased except for the gel-anchorable label, which requires custom synthesis and raises the barrier for researchers to adopt the method. Another drawback of the ExM protocol is that genetically encoded fluorophores cannot be imaged without antibody labeling. Additionally, ExM was unable to retain native proteins in the gel and used custom made reagents not widely available. Thus, it would be desirable to leverage ExM to devise new methods for in situ retention and imaging of nucleic acids and proteins within a sample.

SUMMARY OF THE INVENTION

A small molecule linker is synthesized that enables RNA to be covalently attached to the ExM gel. This method, referred to as ExFISH, enables RNA fluorescent in situ hybridization (FISH), which enables identification of transcripts in situ with single molecule precision. In RNA FISH, a set of fluorescent probes complementary to a target strand of mRNA are delivered[2,3]. Single molecule FISH (smFISH) can be performed with multiple fluorophores delivered to a single mRNA via oligonucleotide probes[4]. In intact tissues, amplification strategies, such as hybridization chain reaction (HCR)[5,6], and branched DNA amplification[7,8], can enable a large number of fluorophores to be targeted to a single mRNA. ExFISH can support smFISH in cell culture, and HCR-amplified FISH in intact mouse brain tissues. ExFISH can reveal nanoscale structures of long non-coding RNAs (lncRNAs), as well as for localizing neural mRNAs to individual dendritic spines. ExFISH will be useful for a diversity of questions relating the structure and location of RNA to biological functions.

BRIEF DESCRIPTION OF THE DRAWINGS

The patent or application file contains at least one drawing executed in color. Copies of this patent or patent application publication with color drawings will be provided to the Office upon request and payment of the necessary fee.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 3A-3K: Nanoscale imaging of RNA in mammalian brain. (3A) Widefield fluorescence image of Thy1-YFP mouse brain. (3B) Post-expansion widefield image of (3A). (3C) Widefield fluorescence showing HCR-ExFISH of YFP mRNA in the sample of (3B). (3D) As in (3C), but for Gad1 mRNA. (3E) Composite of (3B-3D), highlighting distribution of Gad1 versus Thy1-YFP mRNAs. (3F) Confocal image of mouse hippocampal tissue from (e) showing single RNA puncta. Inset, one plane of the boxed region (red, YFP protein; cyan, YFP mRNA; magenta, Gad1 mRNA). (3G(i)) Confocal image and (3G(ii)) processed image of HCR-ExFISH using a missense Dlg4 probe, in Thy1-YFP mouse tissue (green, YFP protein). The raw image (3G(i)) uses alternating probes in two colors (red, Dlg4 missense even; blue, Dlg4 missense odd). The processed image (3G(ii)) shows zero co-localized spots (magenta). (3H, 3I) As in (3G(i) and 3G(ii)), but for HCR-ExFISH targeting Actb in Thy1-YFP mouse brain (green, YFP protein; red, Actb even, and blue, Actb odd in (3H(i)); co-localized spots in magenta (3H(ii))). (3I) Confocal image of hippocampal tissue showing co-localized Dlg4 puncta (magenta) overlaid on YFP (green). (3J(i), 3J(ii)) Two representative examples of dendrites with Dlg4 mRNA localized to spines (arrows). (3K(i), 3K(ii)) As in (3J), but with HCR-ExFISH of Camk2a mRNA showing transcripts in dendritic spines and processes. Scale bars (white, in pre-expansion units; blue scale bars are divided by the expansion factor noted): (3A) 500 µm; (3B-3E) 500 µm (expansion factor 2.9×); (3F) 50 µm (2.9×), inset 10 µm; (3G-3I) 10 µm (3×); (3J, 3K) 2 µm (3×). (3E, 3I) maximum-intensity projection (MIP) 27 µm thick (pre-expanded units); (3G, 3H, 3J, 3K) MIPs ~1.6 µm thick.

DETAILED DESCRIPTION

Figure 1A:
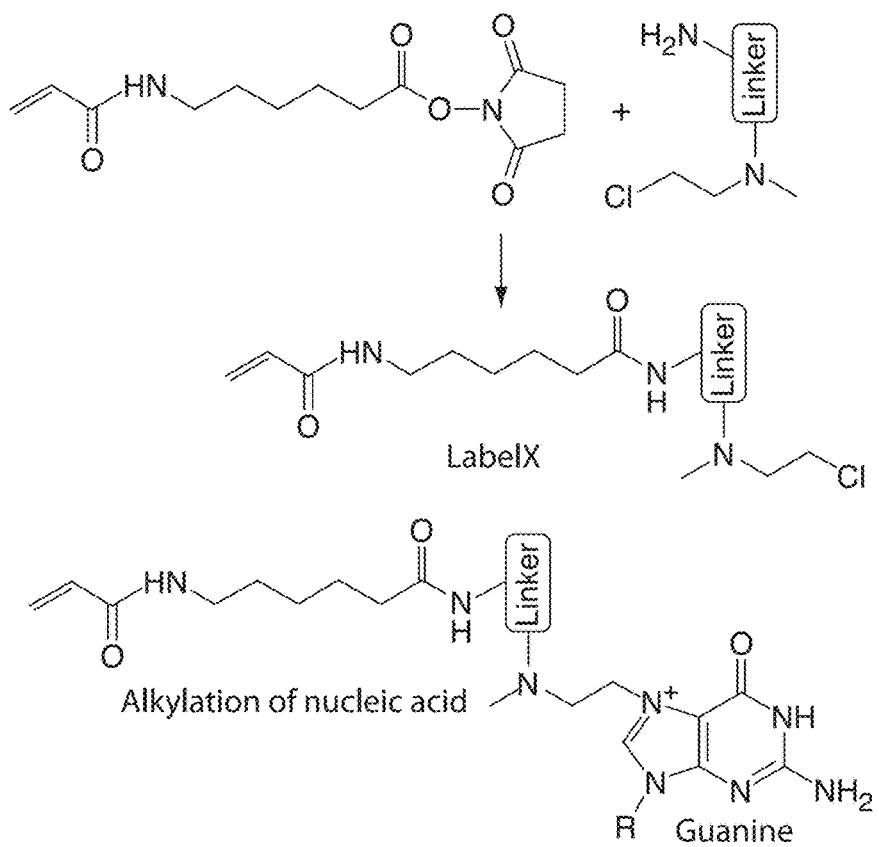
FIG. 1A-1I: Design and validation of ExFISH chemistry. (1A) Acryloyl-X SE (top left) is reacted to LABEL-IT® amine (top right) via NETS-ester chemistry to form LabelX (middle), which serves to make RNA gel-anchorable by alkylating its bases (e.g., the N7 position of guanines) (bottom). (1B) Workflow for ExFISH: biological specimens are treated with LabelX (left), which enables RNA to be anchored to the ExM gel (middle). Anchored RNA can be probed via hybridization (right), after gelation, digestion, and expansion. (1C) smFISH image of ACTB before expansion. Inset shows zoomed-in region, highlighting transcription sites in nucleus. (1D) As in (1C), using ExFISH. (1E) smFISH counts before versus after expansion for seven different transcripts (n=59 cells; each symbol represents one cell). (1F) smFISH image of XIST long non-coding RNA (lncRNA) in the nucleus of a HEK293 cell before expansion (white line denotes nuclear envelope in 1F-1H). (1G) As in (1F), using ExFISH. (1H) smFISH image before expansion (top), and using ExFISH (bottom), of NEAT1 lncRNA in the nucleus of a HeLa cell. Magenta and green indicate probe-sets binding to different parts of the 5' (1-3756 nts) of NEAT1 (see Methods). (1I) Insets showing a NEAT1 cluster (boxed region of (1H)) with smFISH (left) and ExFISH (right). Scale bars (white, in pre-expansion units; blue scale bars are divided by the expansion factor noted))): (1C, 1D) 10 μm (expansion factor, 3.3×), inset 2 μm; (1F, 1G) 2 μm (3.3×), Z scale represented by color coding in pre-expansion units; (1H) 2 μm (3.3×); (1I) 200 nm (3.3×).

The present invention provides for the anchoring of nucleic acids into the swellable gel of Expansion Microscopy (ExM), both for in site genomic and transcriptomic assessment, as well as to enable nucleic acid barcodes to be used to identify essentially arbitrary numbers of molecules. International patent application serial number PCT/US15/16788, which is incorporated herein by reference, teaches that the resolution of conventional microscopy can be increased by physically expanding specimens, a process termed 'expansion microscopy' (ExM). In short, biological specimens are embedded in a swellable gel material, subjected to a treatment to disrupt native biological networks, and then expanded. The advantages to ExM include tissue clearing, resolution improvement, and higher tolerance to sectioning error due to the specimen expansion in the z-axis.

In ExM, fluorophores were anchored directly to the polymer gel, so that proteins could be visualized; however, RNA molecules were not preserved in the gel and are instead lost during the expansion process. Thus, there was no way to probe the transcriptomic information of the sample.

In one embodiment, the invention provides methods that covalently anchor native nucleic acid molecules and antibody barcodes to the expandable gel matrix of expansion microscopy (ExM). Nucleic acids are modified using a small molecule tag, which lets them participate in free radical polymerization during gelling. During the gel formation step, any biomolecules bearing reactive groups are anchored into the gel and isotropically separated as the gel expands.

In one embodiment, the invention provides a nucleic acid reactive reagent that also carries a chemical group that can get incorporated into the gel. After treatment of samples with this reagent, nucleic adds, including DNA and RNA, are covalently labeled with this reagent. Afterwards, during gel formation, labeled nucleic acids are covalently incorporated into the gel. Using such anchored nucleic acids, the information in the nucleic acid can be used as a barcode, e.g. barcoded antibodies can be used for multiplexed in situ staining for ExM, enabling "arbitrary-color" imaging.

By covalently anchoring the nucleic acids, existing technologies for reading out RNA and DNA can be applied to the expanded context. These strategies include single molecule FISH (Imaging individual mRNA molecules using multiple singly labeled probes. Nature Methods, 2008 October; 5(10):877-9), oligo-paint ("Versatile design and synthesis platform for visualizing genomes with Oligopaint FISH probes." PNAS 109.52 (2012): 21301-21306) and many other hybridization based readout strategies. Furthermore, the covalent anchoring allows for sequential hybridization, leading to various multiplexing strategies including serial, spectral, and temporal barcoding schemes. The present invention provides methods for labeling and staining with DNA-barcoded primary antibodies, allowing for an arbitrary number of protein tags to be utilized with ExM, This is a key step towards "infinite color" imaging, since previous the expansion microscopy method only enabled 3-color imaging.

In a further embodiment, the invention provides a method for performing sequential hybridizations against nucleic acids covalently incorporated into an ExM gel. Firstly, buffer condition for hybridizing complementary oligonucleotides bearing fluorophores to the nucleic acids in the ExM gel are provided. Second, the ExM gel is re-embedded in a polyacrylamide gel to minimize distortions resulting from changes in buffer. Third, chemical and enzymatic strategies for removing oligonucleotides hybridized to nucleic acids which are covalently anchored to the gel have been developed, which enables re-staining with the same or different oligonucleotides. Chemical strategies include using formamide and high temperatures to de-hybridize oligonucleotides forming duplexes with nucleic acids in the gel. Enzymatic strategies involve using endonucleases that specifically digest the oligonuetides which are hybridized to nucleic acids while leaving the nucleic acids anchored in the gel intact.

In a further embodiment the invention provides for the multiplexed imaging of proteins and transcripts using Expansion Microscopy. First, a strategy to barcode primary antibodies with oligonucleotides by both covalently and non-covalently associating oligonucleotides with their target antibodies has been developed. While covalent attachment schemes involve reacting to amines and sugar chains found on antibodies, non-covalent attachment schemes use secondary Fab fragments conjugated to oligonucleotide barcodes. Second, a set of conditions for performing immunostaining using these oligonucleotide barcoded primary antibodies has been developed. These conditions include unique buffer compositions for minimizing non-specific binding, as well as temperature ranges for obtaining adequate immunostaining. The oligonucleotides which are reacted to these antibodies possess a chemical group that can be incorporated into the ExM gel to gel formation. Therefore, during gel formation, these oligonucleotides are all anchored into the ExM gel while all proteins are degraded. In addition, a strategy for the multiplexed read out of the oligonucleotides and nucleic acids, including RNA and DNA, in the ExM gel using sequential hybridization has been developed. This approach consists of sequentially hybridizing complementary strands bearing fluorophores to each unique oligonucleotide or nucleic acid, one by one, serially. Finally, the set of capabilities offered by out technique enable exponential barcoding schemes demonstrated recently by a few groups. For instance, this approach allows for barcoding nucleic acids via temporal color barcodes or temporal binary barcodes.

One embodiment of a method for in situ genomic and transcriptomic assessment of target nucleic acids present in a biological sample comprises the steps of:

a) treating the biological sample with a small molecule linker capable of linking to at least one target nucleic acid and to a swellable material;

b) embedding the biological sample wherein the small molecule linker is bound to the at least one target nucleic acid in the biological sample and to the swellable material;

c) subjecting the biological sample to a physical disruption method;

d) swelling the swellable material to form an expanded biological sample;

e) providing at least one oligonucleotide complementary to the at least one target nucleic acid, wherein the at least one oligonucleotide hybridizes to the at least one target nucleic acid; and f) genomically or transcriptomically assessing the expanded biological sample.

In this and other methods, the small molecule linkers are attached to target nucleic acids via a chemical reactive group capable of covalently binding the target nucleic acid. The small molecule linker may be labeled and or the at least one oligonucleotide may be labeled.

In another embodiment, embedding the biological sample in a swellable material may comprise permeating the biological sample with a composition comprising precursors of a swellable polymer and forming a swellable polymer in situ.

In another embodiment, the at least one target nucleic acid is anchored to the swellable material.

In another embodiment, the physical disruption method is an enzymatic digestion.

In another embodiment of the just described method, the target nucleic acids are DNA and/or RNA.

In another embodiment, the expanded biological sample expresses one or more labeled target nucleic acids.

In another embodiment, the expanded sample may be buffered prior to providing at least one oligonucleotide. After buffering, the expanded sample may be re-embedded in a non-swellable material prior to genomically or transcriptically assessing the expanded biological sample. Buffering enables removal of the at least one oligonucleotide through chemical or enzymatic means. For example, formamide and high temperature could be used to chemically remove the at least one oligonucleotide while endonucleases that specifically digest the at least one oligonucleotide could accomplish the same task enzymatically. After buffering, serial or sequential genomic and transcript assessments may be performed on the same expanded sample by repeating the steps of removing the at least one oligonucleotide and providing either the same or different at least one oligonucleotide.

Methods a. ExM-FISH and ExM FISH-HCR

Secondary antibodies were conjugated to DNA oligo barcodes bearing 5' acrydite and 3' amine via the Solulink commercial kit. After primary and secondary antibody staining, samples were gelled, digested, and expanded following ExM procedure. Following expansion, the gelled samples were re-embeded in a 4% polyacrylamide gel by incubating the expanded gel with acrylamide, bis-acrylamide, and radical initiators. To perform in situ hybridization, gelled samples were incubated with fluorescently labeled oligos and excess oligos were subsequently washed out. To perform in situ hybridization with Hybridization Chain Reaction (HCR) signal amplification, gelled samples were incubated with oligo probes bearing a complementary region to the antibody conjugated oligo barcodes and a site for HCR initiation. After washing out excess probes, HCR hairpins were washed in to initiate the amplification.

b. Primary-Fab Antibody Conjugation and Staining

Fab Secondary antibodies were conjugated to DNA oligo barcodes bearing 5' acrydite and 3' amine via the Solulink commercial kit. To conjugate IgG primary antibodies with oligo tagged Fabs. Fabs were incubated with primary antibodies along with fluorescently labeled oligonucleotides complementary to the barcodes. Subsequently, excess fabs and oligos were removed using centrifugal spin filters.

Cultured HeLa cells were fixed with 4% formaldehyde. Subsequently, staining antibody mixture was prepared by mixing appropriate purified primary-fab conjugated in a blocking buffer containing dextran sulfate, normal donkey serum, and rabbit gamma globulin. Finally, fixed cells were incubated with the antibody mixture overnight and any excess was washed off.

ExFISH: Design and Validation of RNA Anchoring Chemistry

Figure 1B:
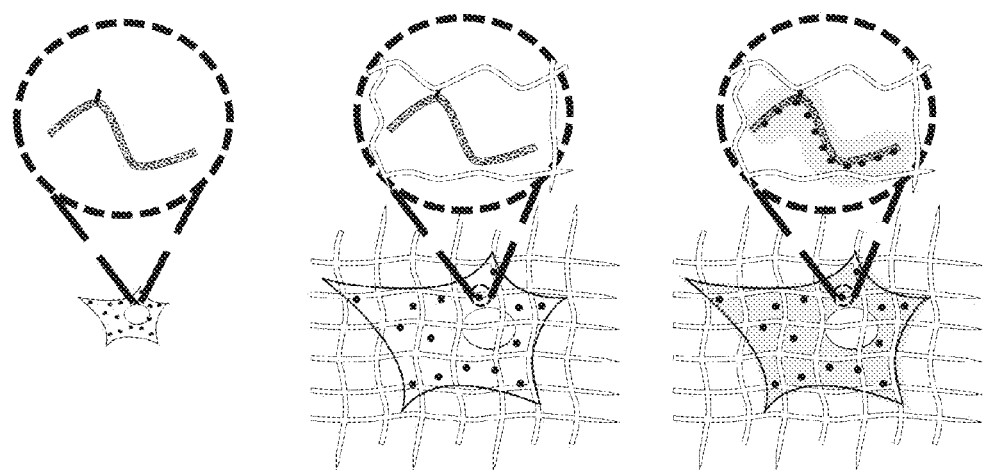
Figure 4A:
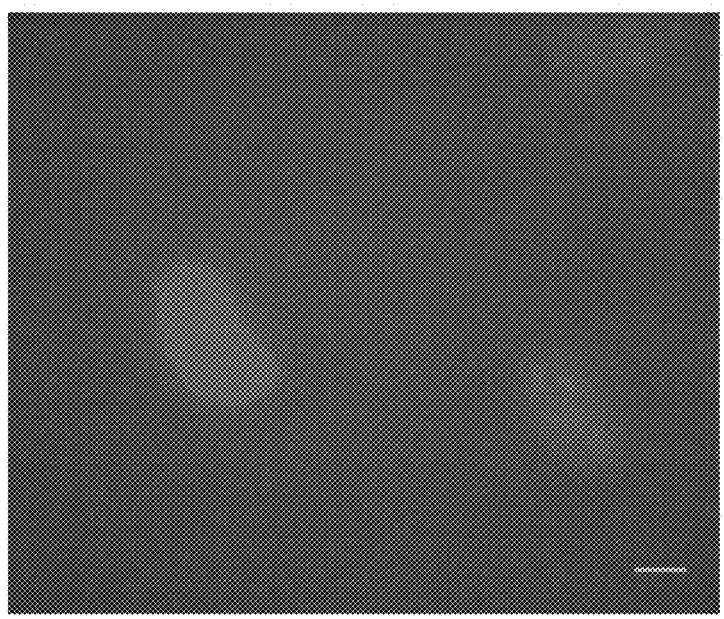
FIG. 4A-4B: (4A) Epi-fluorescence image of single molecule FISH (smFISH) against GAPDH on HeLa cells expanded without LabelX treatment. (4B) Epi-fluorescence image of smFISH performed against GAPDH on expanded HeLa cells treated with LabelX. Images are maximum intensity projections of 3-D stacks. Nuclei stained with DAPI (shown in blue). Scale bars: 20 µm (post-expanded units).
Figure 4B:
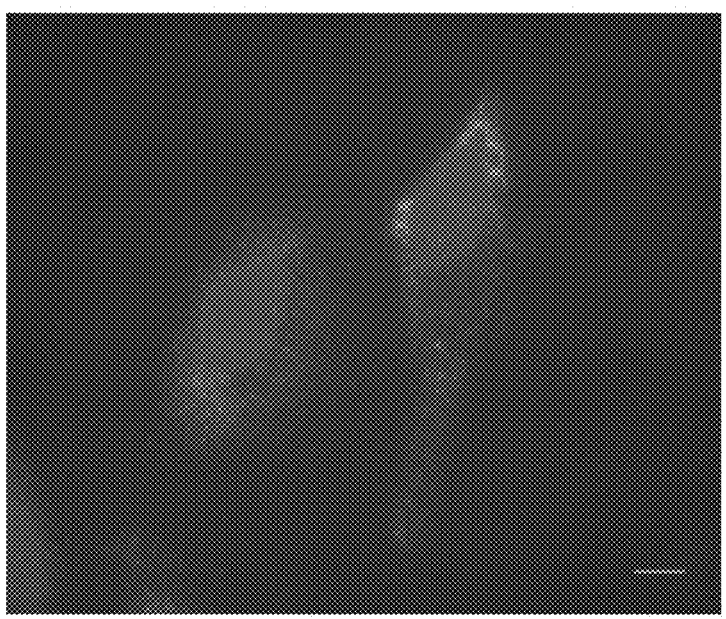
Figure 5A:
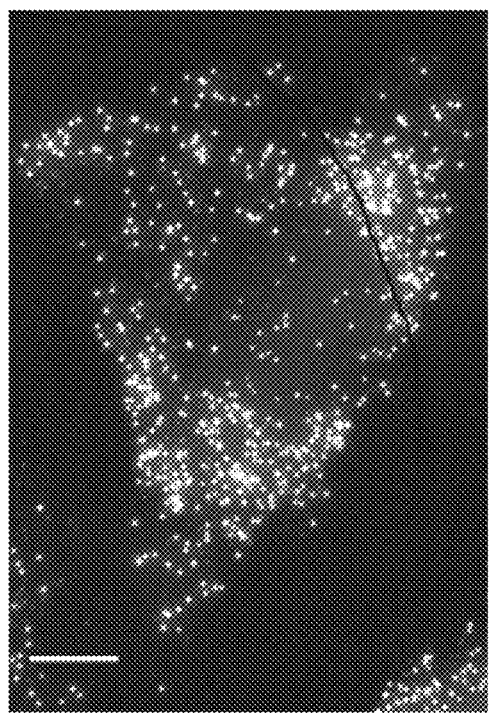
FIG. 5A-5E: To assess the effect of LabelX on fluorescent in situ hybridization, fixed HeLa cells were stained with smFISH probe-sets, followed by DNAse I treatment to remove the staining. The cells were then treated with LabelX and stained again with the same smFISH probe-sets. (5A) UBC staining before LabelX treatment and (5B) UBC staining after probe removal and LabelX treatment. (5C) EEF2 staining before LabelX treatment. (5D) EEF2 staining after probe removal and LabelX treatment. (5E) Comparison of smFISH spots counted for individual cells before LabelX, and after probe removal and application of LabelX. The number of RNA molecules detected in a given cell was quantified using an automated spot counting algorithm (n=7 cells for each bar). Plotted are mean±standard error; no significant difference in spot counts before vs after LabelX (p>0.5 for before vs. after for UBC, p>0.5 for before vs. after for EEF2; t-test, unpaired, two-tailed). Images in 5A-5D are maximum intensity projections of 3-D stacks; scale bars: 10 µm (pre-expansion units).
Figure 5B:
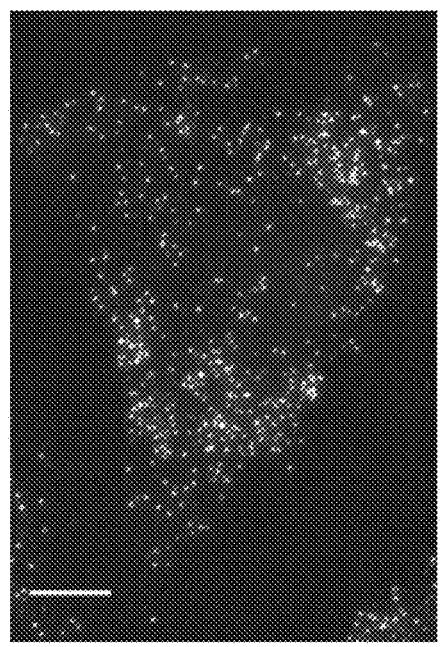
Figure 5C:
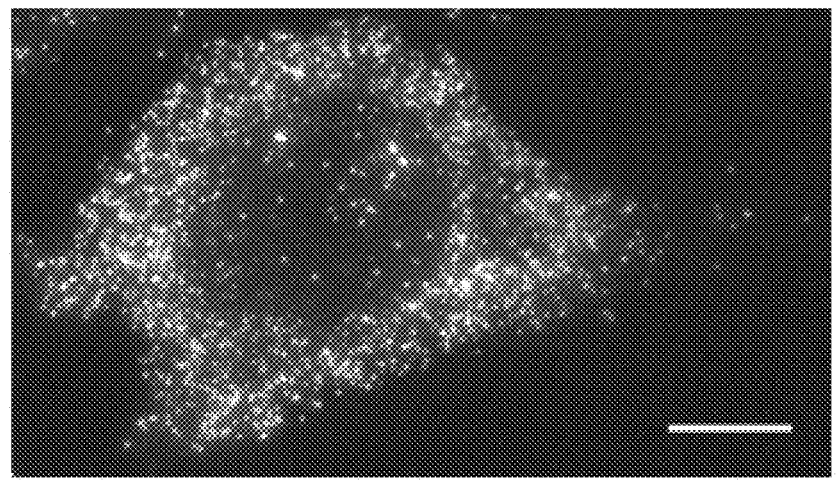
Figure 5D:
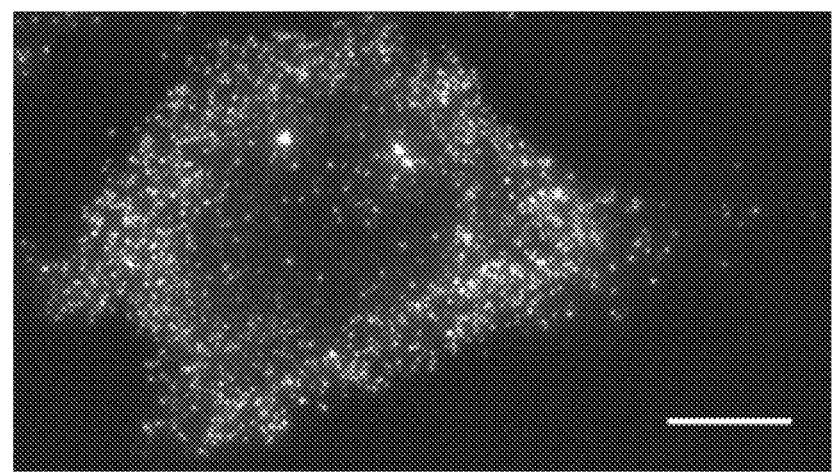
Figure 5E:
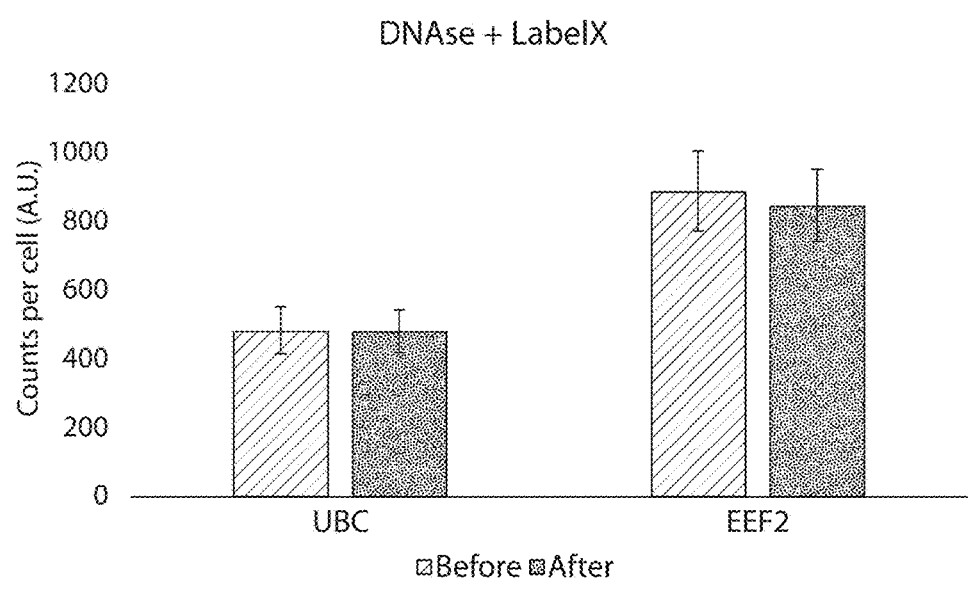
Figures 6A, 6B:
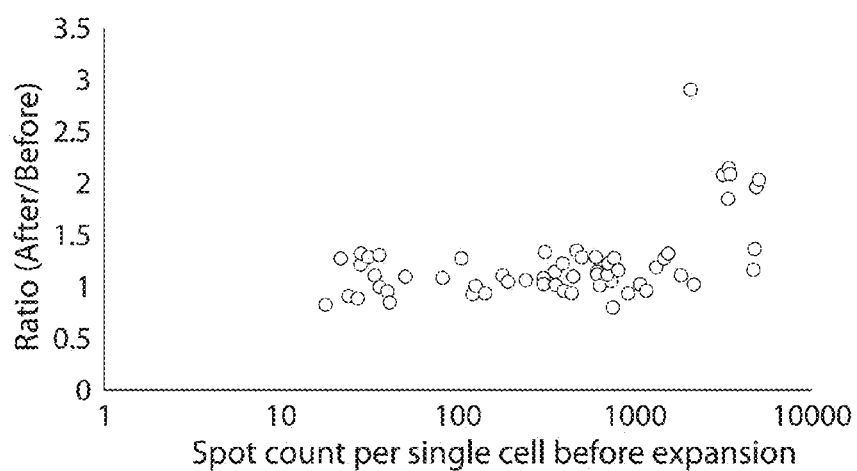
FIG. 6A-6G: Different RNA species spanning 3 orders of magnitude in abundance were detected via single molecule RNA fluorescent in situ hybridization (FISH) in HeLa cells before and after ExM with LabelX treatment (shown in FIG. 1E). (1A) Ratio of FISH spots detected after expansion to spots detected before expansion for single cells. Representative before vs. after ExFISH images shown: (1B,1C) TFRC; (1D,1E) GAPDH; (1F, 1G) ACTB. Scale bars, 10 µm (pre-expanded units) in 1B, 1D, 1F; 1C, 1E, 1G, expanded physical size 21 µm (imaged in PBS).
Figure 6C:
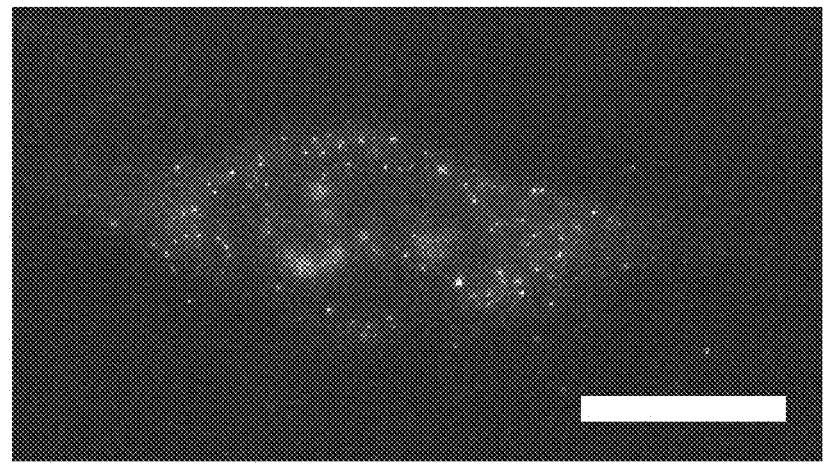
Figure 6D:
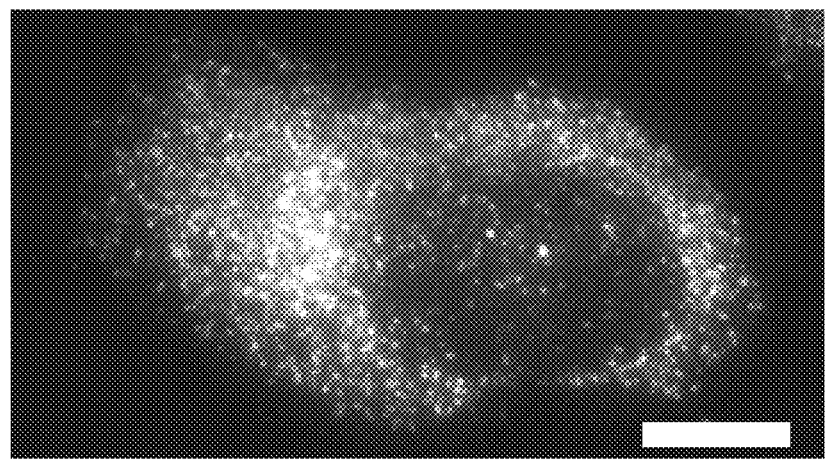
Figure 6E:
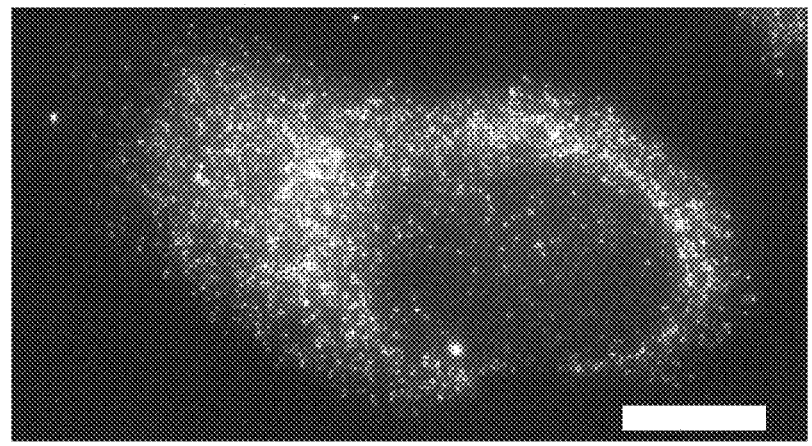
Figure 6F:
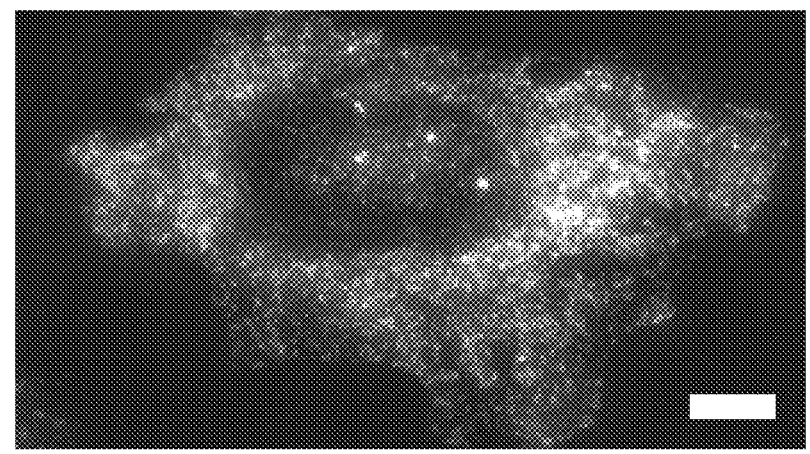
Figure 6G:
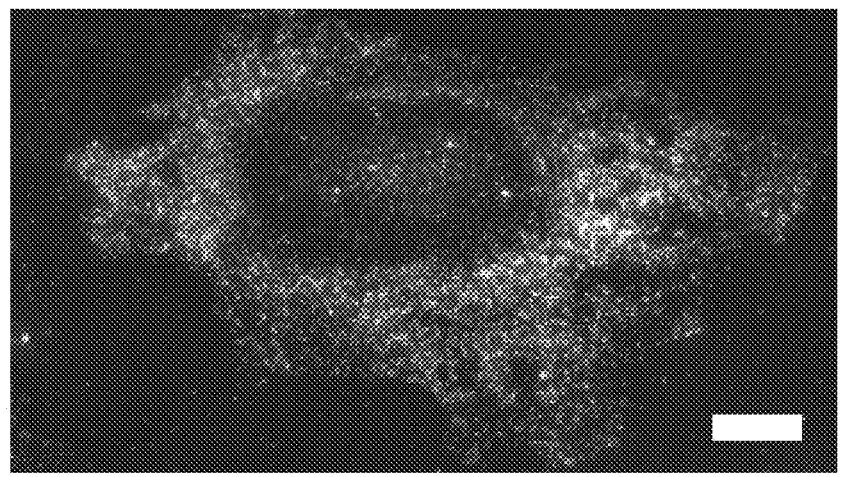

Because of the nature of the reactions occurring during ExM, covalently linking RNAs directly to the ExM gel is necessary. Although transcripts are crosslinked to proteins during fixation, the strong proteolysis of ExM precludes a reliance on proteins for RNA retention (FIGS. 4A, 4B). Thus, covalently securing RNA molecules directly to the ExM gel via a small molecule linker enables the interrogation of these molecules post-expansion. A reagent was synthesized from two building blocks: a molecule containing both an amine as well as an alkylating group that primarily reacts to the N7 of guanine, and a molecule that contains an amine-reactive succinamide ester and a polymerizable acrylamide moiety. Commercially available reagents exist that satisfy each of these two profiles, such as Label-It Amine (MirusBio) and 6-((Acryloyl)amino) hexanoic acid (Acryloyl-X SE, here abbreviated AcX, Life Technologies; all reagents are listed in Table 1). FIG. 1A depicts this molecule, which enables RNA to be covalently functionalized with a free radical polymerizable group, and which will be referred to as LabelX. As shown in FIG. 5E, LabelX does not impede smFISH readout. The original ExM protocol and the use of LabelX allows a procedure wherein a sample could be treated with LabelX to make its RNAs gel-anchorable, followed by gel formation, proteolysis, and osmotic swelling as performed in the original ExM protocol. Once a sample was thus expanded, the RNAs could then be interrogated through FISH (FIG. 1B).

Figure 1C:
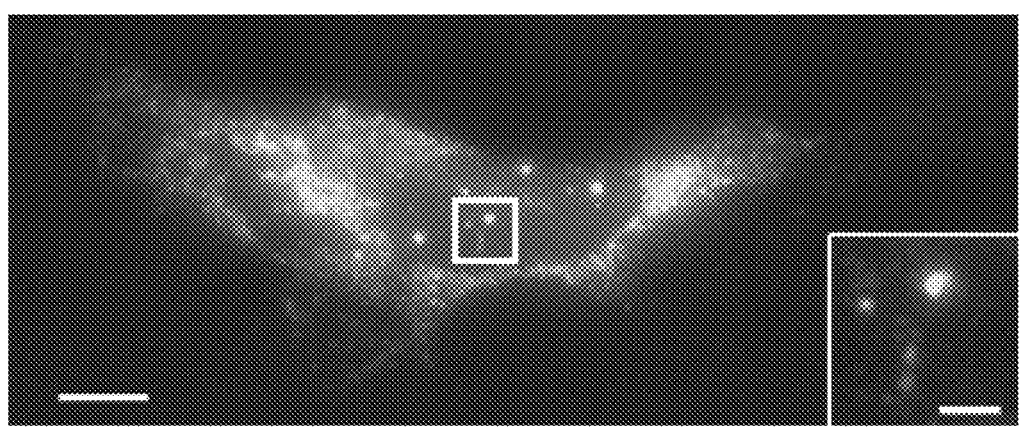
Figure 1D:
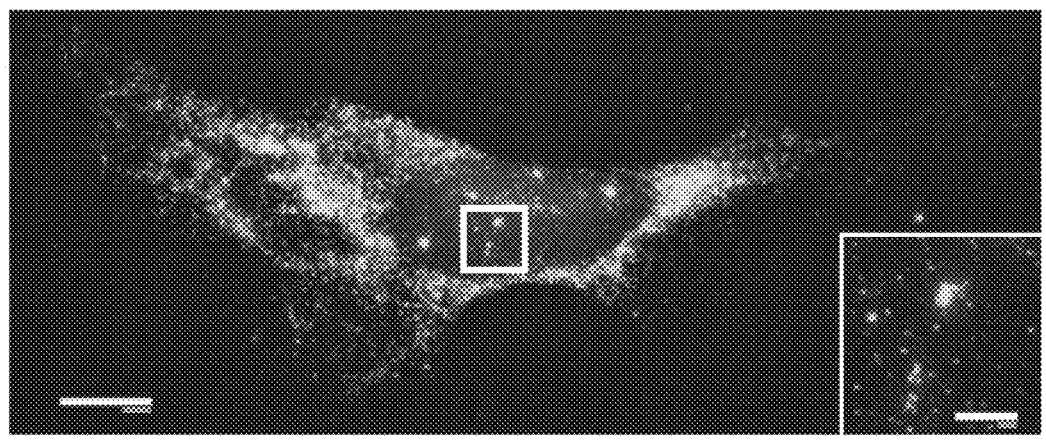
Figure 1E:
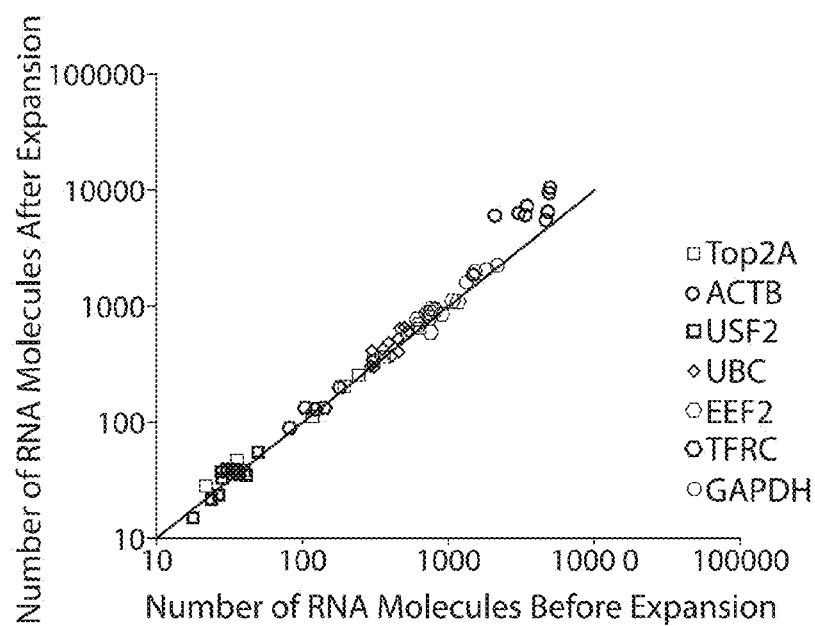
Figure 7A:
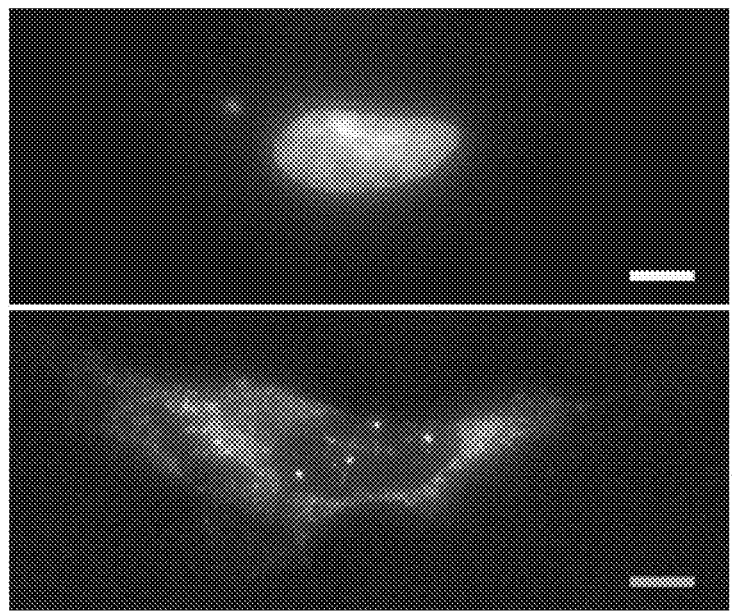
FIG. 7A-7E: (7A) Pre-expansion widefield image of a cultured HeLa cell stained with DAPI to visualize the nucleus (top panel) and smFISH probes against ACTB (bottom panel). (7B) Post-expansion widefield image of the same cell as in (a). (7C) Pre-expansion widefield image of LabelX treated Thy1-YFP brain slice (left panel, YFP protein) stained with DAPI (right panel) (MIP, 4 µm z-depth). (7D) Post-expansion image of the same region as in (c) (MIP, 12 µm). (7E) Ratio of the expansion factor of cell bodies for individual cells to the expansion factor of their respective nuclei. smFISH stain is used to outline the boundaries of the cell bodies of cultured cells while the endogenous YFP protein is used to demarcate the cell bodies of neurons in Thy1-YFP brain slices. Plotted are mean±standard error. The ratio for both cultured cells and brain slices did not significantly deviate from one (p>0.05 for both, 1-sample t-test; n=6, cultured HeLa cells; n=7, cells in 1 brain slice). Scale bars, 10 µm.
Figure 7B:
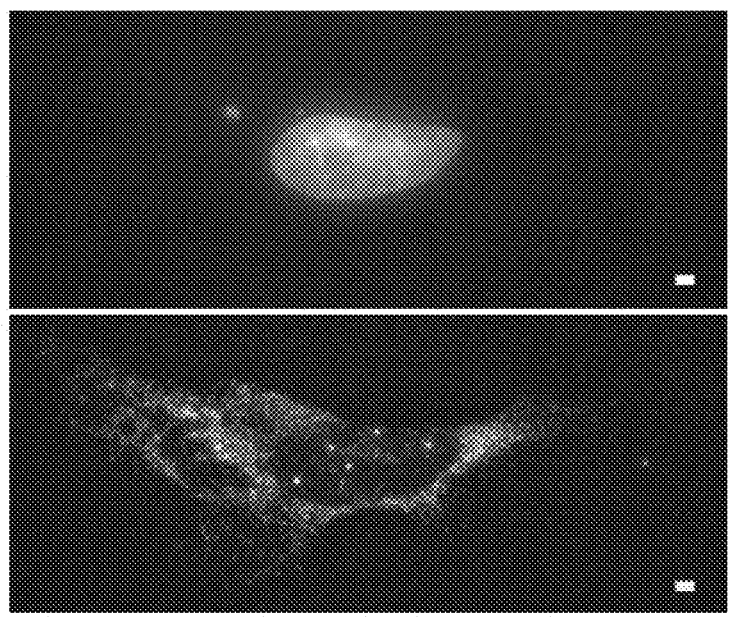
Figure 7C:
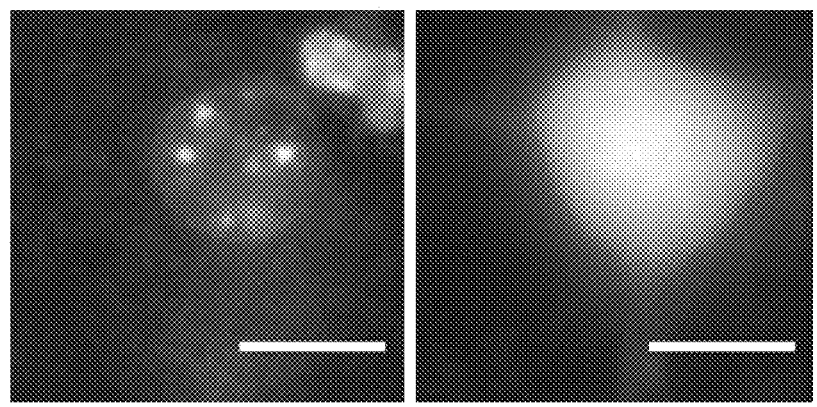
Figure 7D:
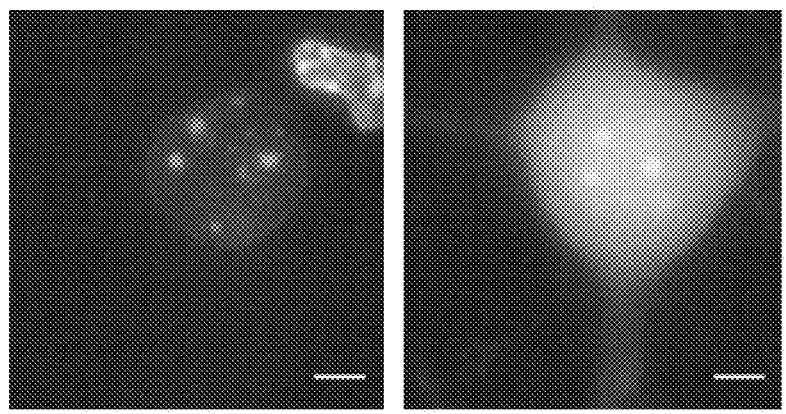
Figure 7E:
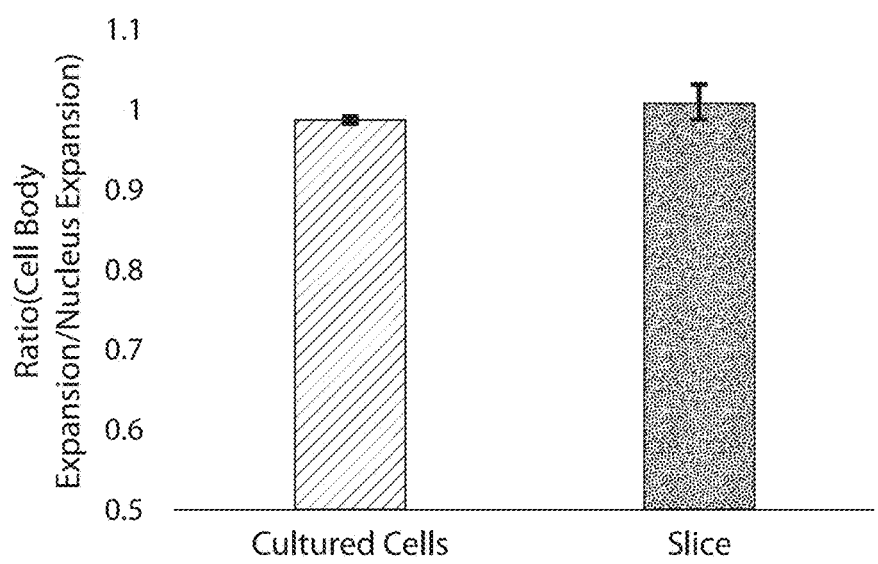
Figure 8A:
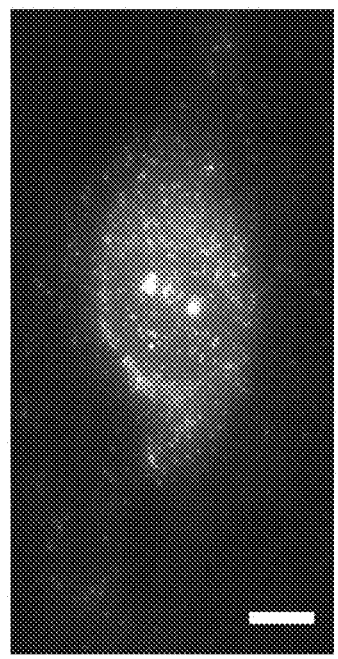
FIG. 8A-8D: (8A) Representative FISH image of TOP2A in a single HeLa cell before expansion (MIP of cell thickness). (8B) ExFISH image of cell in (8A) taken with the same optical parameters. (8C) Merged image of (8A) and (8B) (red and green for before and after expansion respectively); distance measurements between pairs of mRNA spots before (L, red line) and after (L', green line; note that these lines overlap nearly completely) expansion were used to quantify expansion isotropy. (8D) Mean of the absolute value of the measurement error (i.e., |L-L'|) plotted against measurement length (L) for all pairs of mRNA spots (mean±standard deviation, N=4 samples, $6.8 \times 10^5$ measurements). Scale bars: white, 10 µm pre-expansion units; blue, white scale bar divided by expansion factor. Orange line indicates diffraction limit of the microscope used (see methods for details).
Figure 8B:
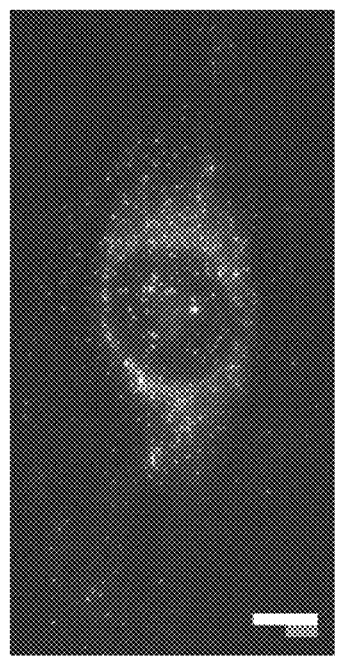
Figure 8C:
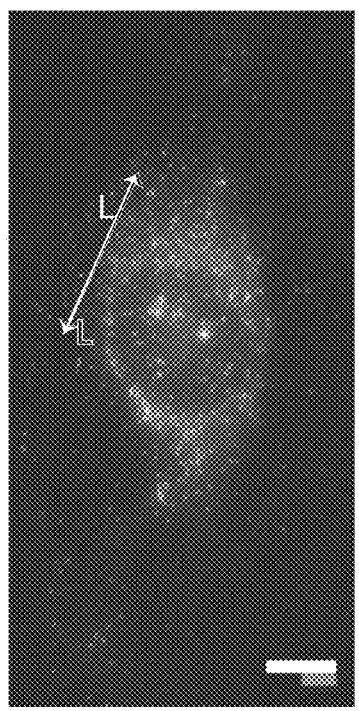
Figure 8D:
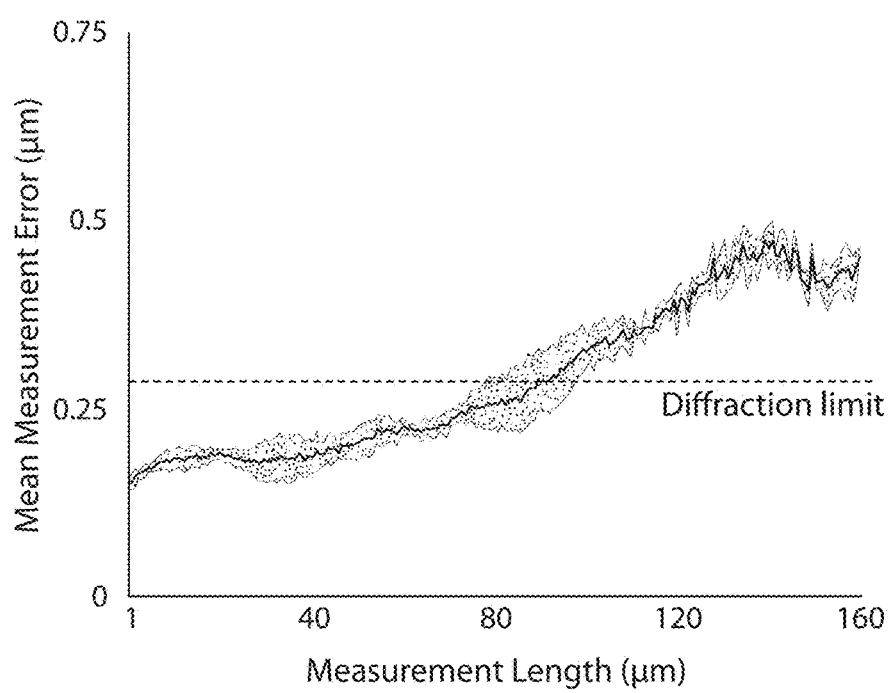
Figure 9A:
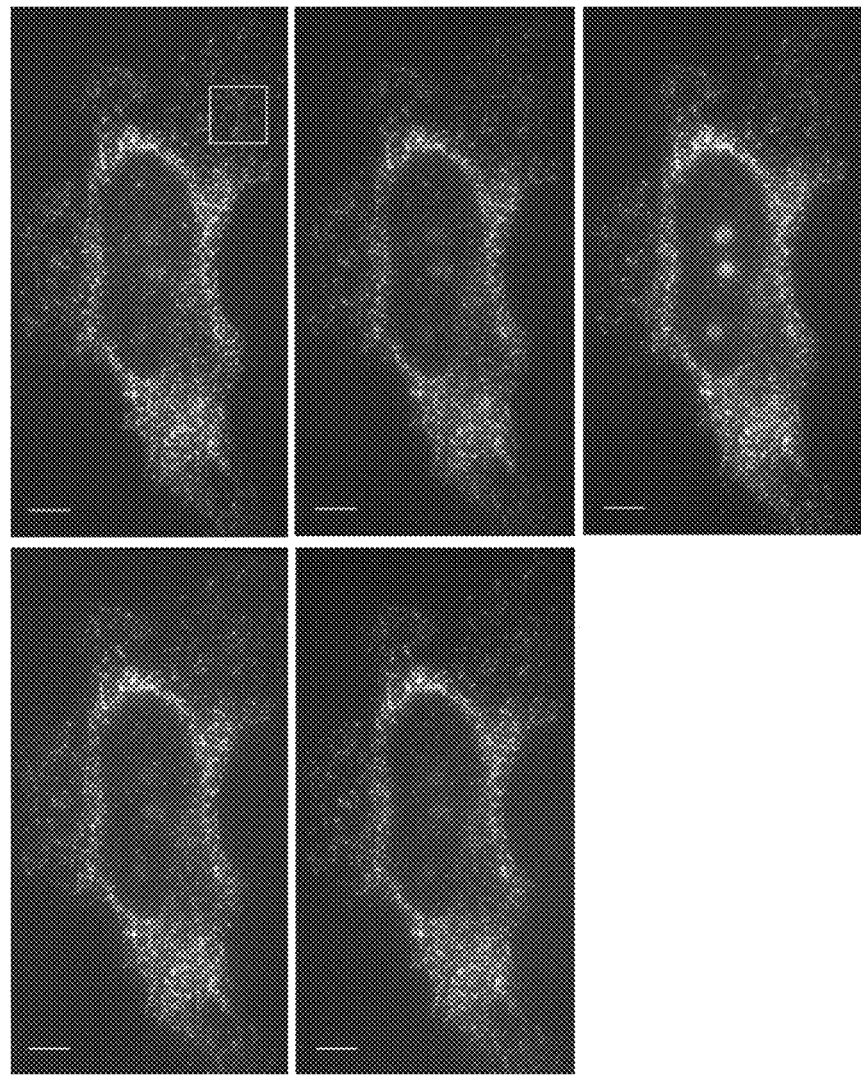
FIG. 9A-9B: (9A) Five consecutive widefield fluorescence images (top to bottom, then left to right) of GAPDH, applied to the cell of FIG. 2a. (9B) Widefield fluorescence images showing ExFISH with serially delivered probes against six RNA targets (right to left, then top to bottom: NEAT1, EEF2, ACTB, UBC, GAPDH, and USF2) in a cultured HeLa cell (raw images of composite shown in FIG. 2E). Scale bars: 20 µm in expanded units.
Figure 9B:
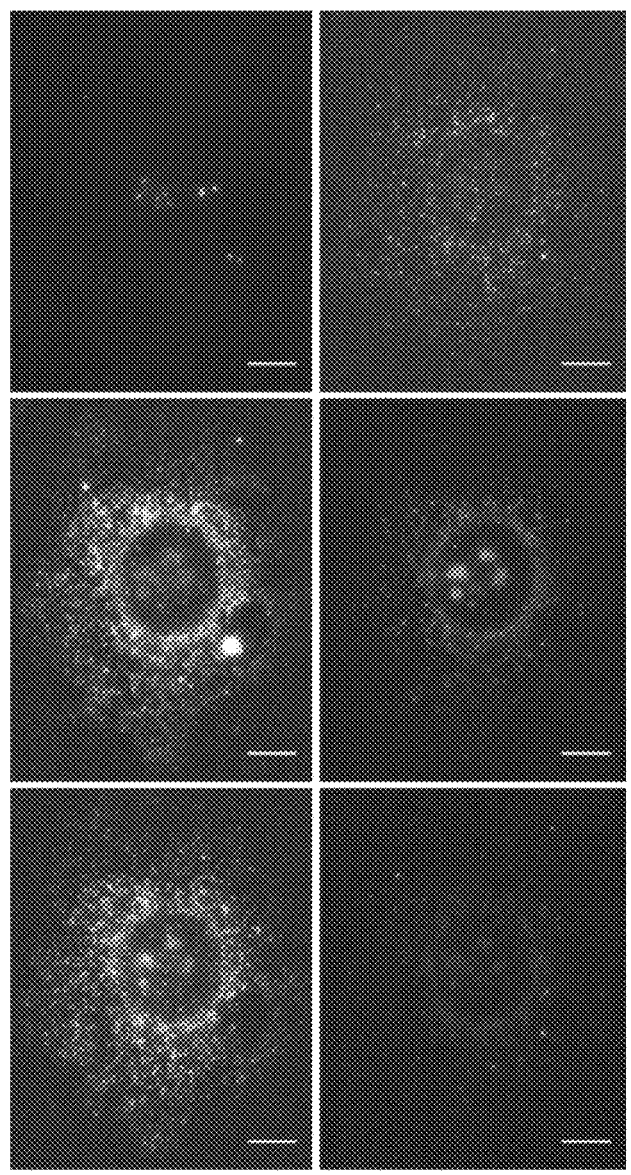

To quantify RNA transcript anchoring yield after expansion, smFISH probes were used, targeting mRNAs of varying copy number (7 targets, with copy number ranging from ~10 to ~10,000 per cell, n=59 cells across all 7 targets). smFISH images, taken with probes delivered before (FIG. 1C) and after (FIG. 1D) expansion, to the same cells, showed no loss of transcript detectability with expansion for both low- and high-copy number transcripts (FIG. 1E). The ratio of transcripts detected was near unity at low transcript counts (e.g., in the 10's), however, more transcripts were detected after expansion for highly expressed mRNAs (e.g., in the 1,000's) (FIGS. 9A, 9B, Table 2). This difference arises from the high density of smFISH spots for these targets in the un-expanded state, with the expansion process de-crowding spots that previously were indistinguishable. For example, for smFISH against ACTB, we were able to resolve individual ACTB mRNA puncta post-expansion even within transcriptional foci in the nucleus (FIG. 1C, versus FIG. 1D), which can be dense with mRNA due to transcriptional bursting. Thus, ExFISH is capable of supporting single molecule RNA readout in the expanded state. Since Label-It also reacts to DNA, the ExFISH process enables uniform expansion of the nucleus (FIGS. 7A-C). The isotropy of ExFISH (FIG. 8) was numerically similar to that observed when protein targets were labeled and expanded in the original ExM protocol'. In recent ExM protocols in which proteins are anchored to the same hydrogel as used in ExFISH, with a similar linker[9,10], the distortion is small (a few percent distortion, in cells and tissues). These earlier results, since they were obtained with similar polymer chemistry, serve to bound the ExFISH distortion. The expansion factor is slightly lower than in our original ExM paper (i.e., ~3.3× versus ~4×, expansion factors can be found in Figure Legends of this manuscript) due to the salt required to support hybridization of probes.

Nanoscale Imaging of lncRNA with ExFISH

Figure 1F:
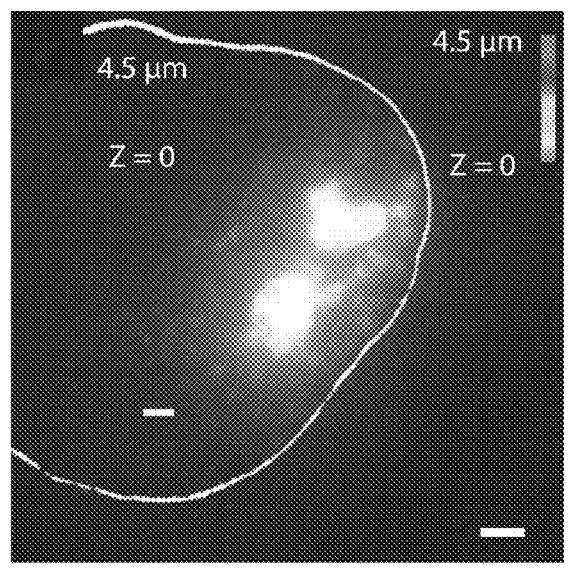
Figure 1G:
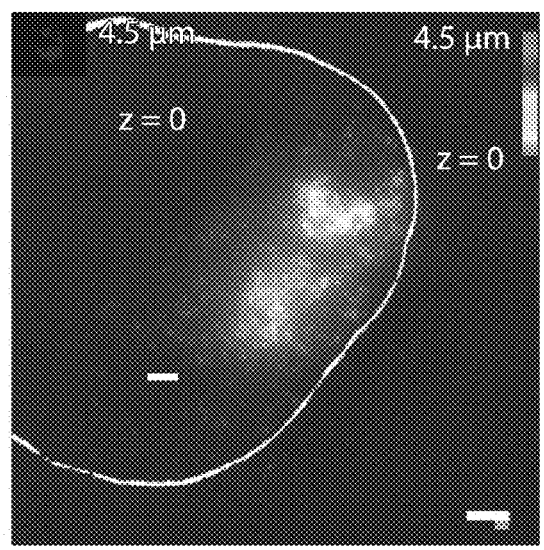
Figure 1H:
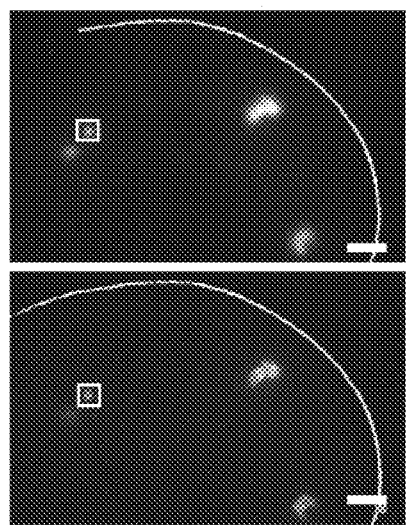
Figure 1I:
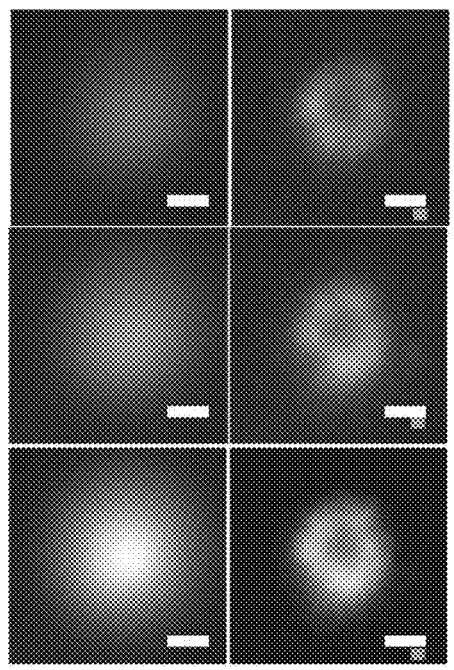

Long non-coding RNAs (lncRNAs) known to serve structural roles in cell biology were imaged. The lncRNA XIST was imaged. Its role in inactivating the X chromosome may depend on initial association with specific chromatin subregions through a process which is still being revealed[11]. The pre-expansion image (FIG. 1F) shows two bright globular fluorescent regions, presumably corresponding to the X chromosomes of HEK cells undergoing inactivation[11-13], but post-expansion, individual puncta were apparent both within the globular regions as well as nearby (FIG. 1G). ExFISH was used additionally to examine the previously described[14] ring-shaped morphology of ensembles of NEAT1 lncRNAs (FIG. 1H), which has been hypothesized to play an important role in gene expression regulation and nuclear mRNA retention[15]. Before expansion, NEAT1 presents in the form of bright, diffraction-limited puncta (FIG. 1H, FIG. 1I), but after expansion, the ring-shaped morphology becomes clear (FIG. 1H, FIG. 1I). Given the complex 3-D structure of the genome[16], mapping lncRNAs may be useful in defining key chromatin regulatory complexes and their spatial configurations.

Super-Resolved, Multiplexed Imaging of RNA with ExFISH

Figure 2A:
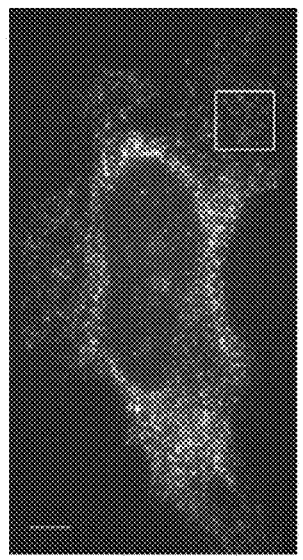
FIG. 2A-2E: Serially hybridized and multiplexed ExFISH. (2A) Widefield fluorescence image of ExFISH targeting GAPDH. (2B) Boxed region of (2A), showing 5 repeated re-stainings following probe removal (see Methods); lower right panel, overlay of the 5 images (with each a different color, red, green, blue, magenta, yellow), showing co-localization. (2C) ExFISH RNA counts for each round, normalized to the round 1 count; plotted is mean±standard error; n=3 regions of (2A). (2D) Signal-to-noise ratio (SNR) of ExFISH across the five rounds of staining of (2A), computed as the mean puncta brightness divided by the standard deviation of the background. (2E) Composite image showing ExFISH with serially delivered probes against six RNA targets in a cultured HeLa cell (raw images in FIG. 9); colors are as follows: NEAT1, blue; EEF2, orange; GAPDH, yellow; ACTB, purple; UBC, green; USF2, light blue. Scale bars (expanded coordinates): (2A) 20 µm; (2B) 10 µm; (2E) 20 µm.
Figure 2B:
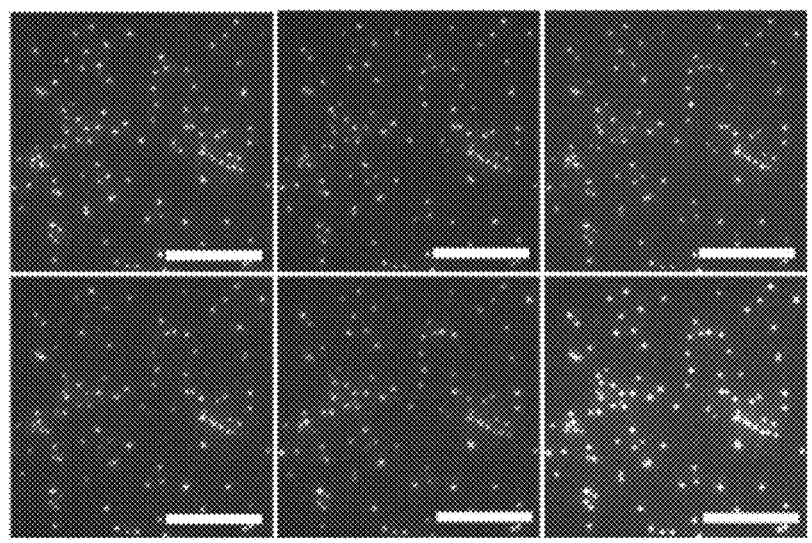
Figure 2C:
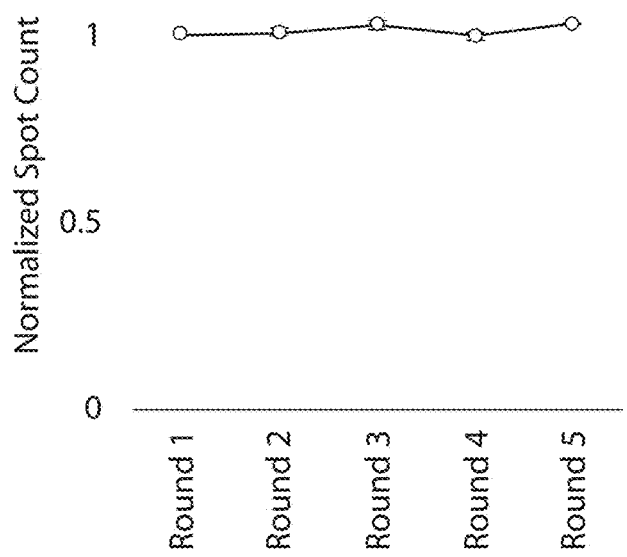
Figure 2D:
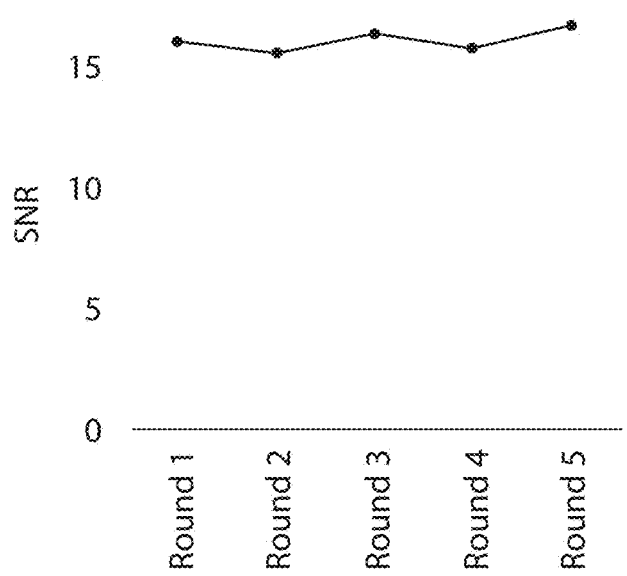
Figure 2E:
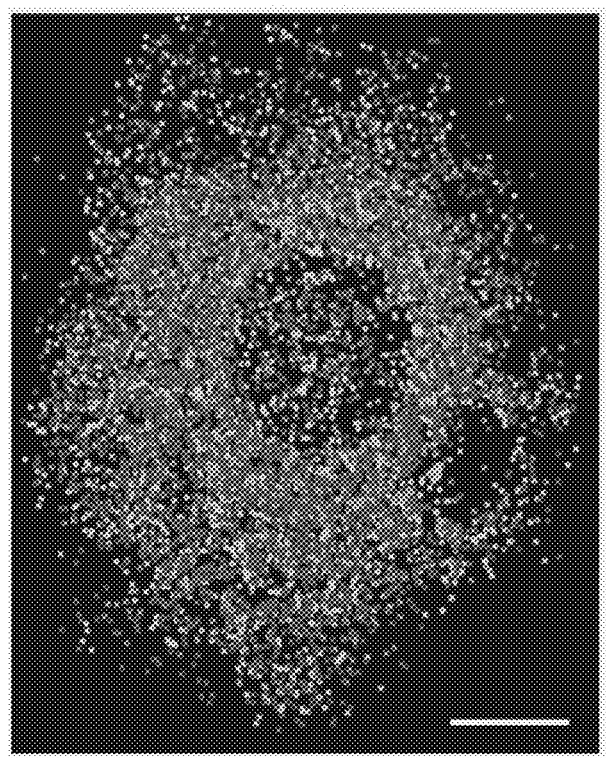

The combination of covalent RNA anchoring to the ExM gel, and the de-crowding of the local environment that results from expansion, could facilitate strategies that have been proposed for multiplexed RNA readout[17-19] based upon sequential hybridization with multiple probe sets. In order to facilitate multiple cycles of FISH, we re-embedded expanded specimens in charge-neutral polyacrylamide. This process allowed expanded gels to be immobilized for multi-round imaging, and additionally stabilized the expanded specimen throughout salt concentration changes in the protocol. Such re-embedded samples exhibited similar expansion factors as non-re-embedded samples (i.e., ~3×), and were robust to multiple wash-stain cycles as assessed by repeated application of the same probe set (FIG. 2A, FIG. 9A, showing 5 rounds of smFISH staining against GAPDH on cultured cells). This stability was observed even under stringent wash conditions designed to minimize cycle-to-cycle crosstalk (e.g., 100% formamide). Across the 5 rounds, there was no distortion of the locations of individual RNA spots from round to round (FIG. 2B), nor variance in detection efficiency or signal-to-noise ratio (FIGS. 2C, 2D). Having validated the cycle-to-cycle consistency, we next demonstrated the capability of multiplexed ExFISH by applying probes for GAPDH, UBC, NEAT1, USF2, ACTB, and EEF2 in series, enabling 6 individual RNAs to be identified and localized in the same cell (FIG. 2E, FIG. 9B). Thus, serial FISH is applicable to samples expanded after securing RNA to the swellable polymer as here described, making it straightforward to apply probe sets computationally designed to yield more information per FISH cycle, e.g. MERFISH[18-20].

3D Nanoscale Imaging of RNA in Mouse Brain Tissue

Figure 3A:
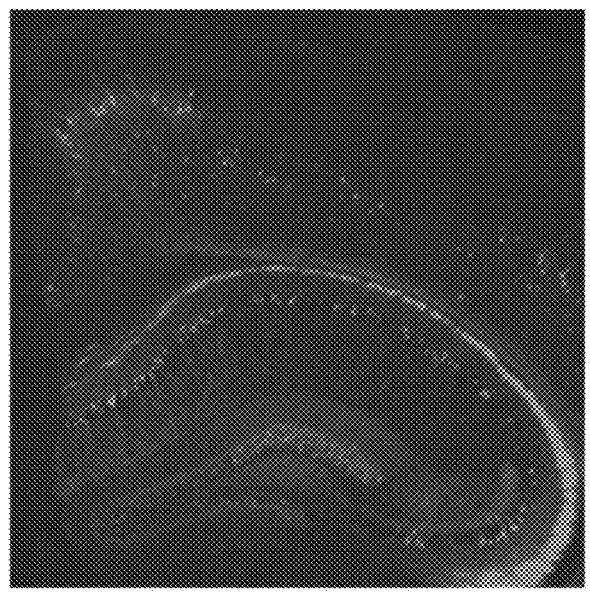
Figure 3B:
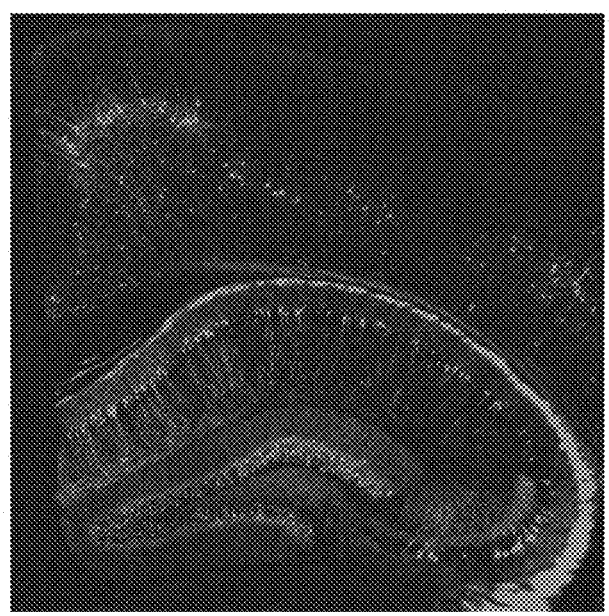
Figure 3C:
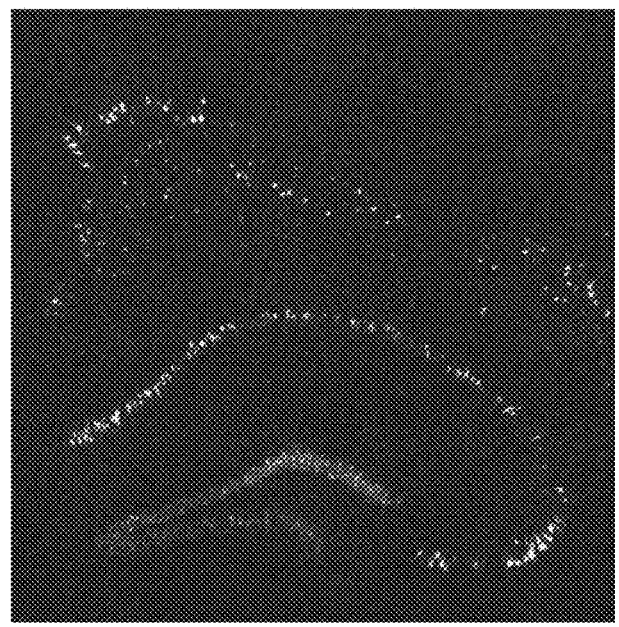
Figure 3D:
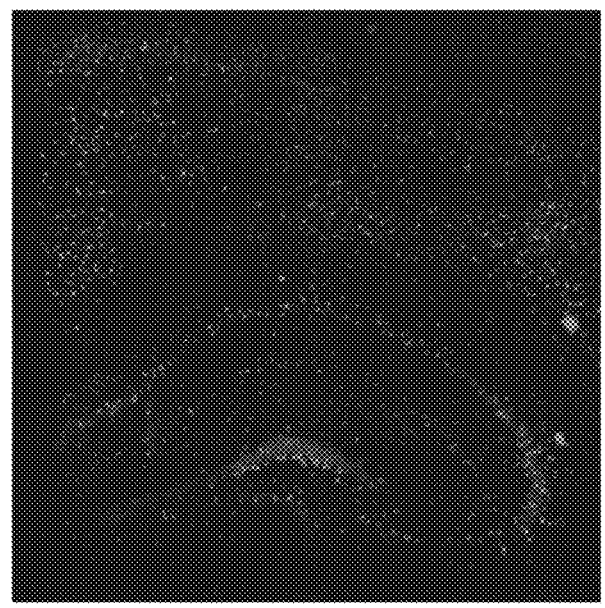
Figure 3E:
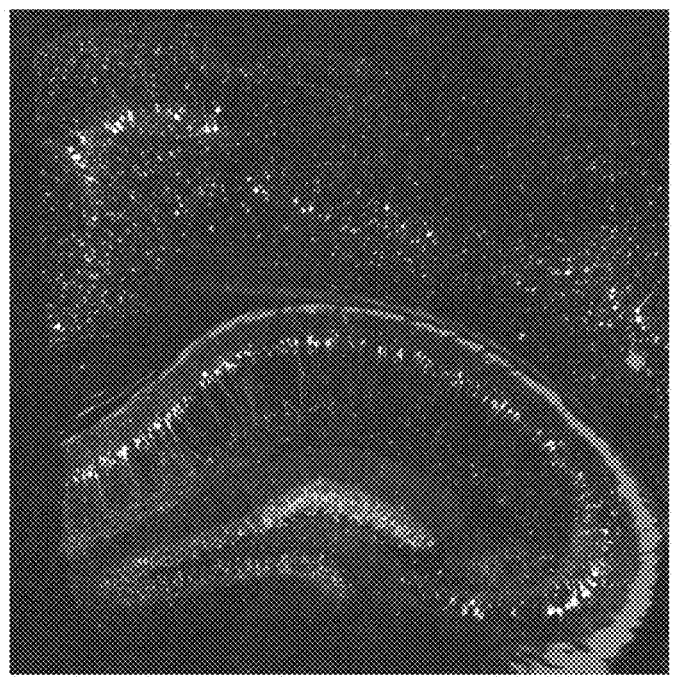
Figure 3F:
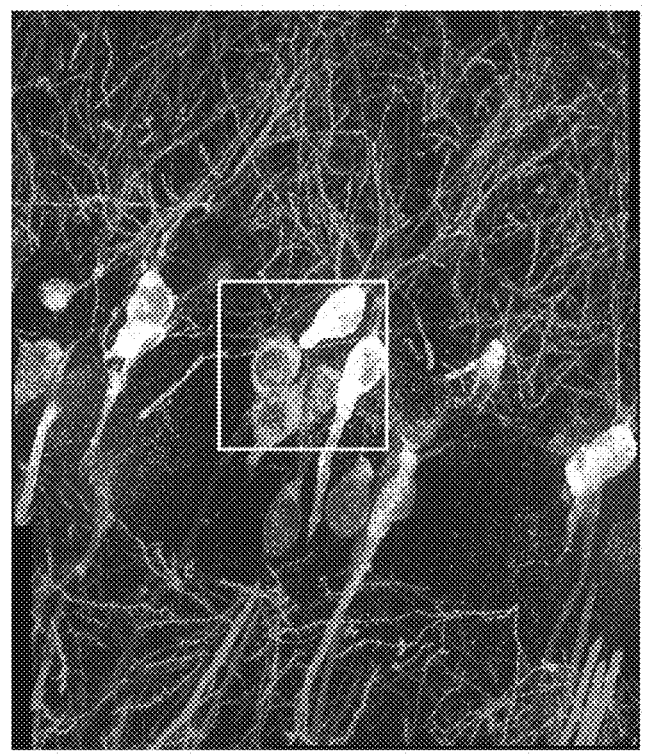
Figure 11A:
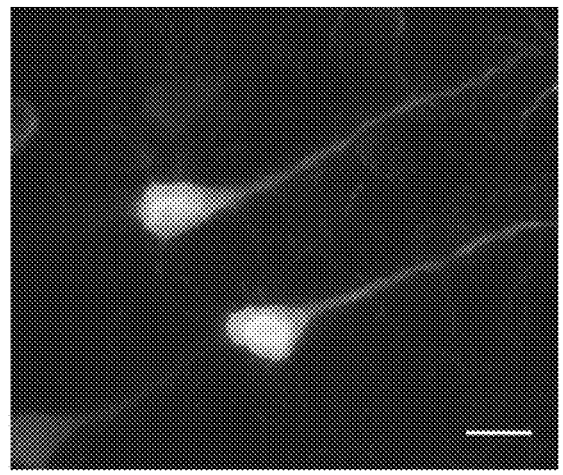
FIG. 11A-11C: (11A) Widefield image of a LabelX treated Thy1-YFP brain slice (YFP protein, green) stained with probes against YFP (red) and Gad1 (magenta) followed by HCR amplification. Probes against YFP transcripts were amplified with the B1 amplifier set (see Methods) while probes against Gad1 transcripts were amplified with the B2 amplifier set (MIP, 59 µm). (11B) Widefield image of LabelX treated Thy1-YFP brain slice (YFP protein, green) treated with the same HCR amplifiers as in (a) (namely B1 (red) and B2 (magenta)) without the addition of probes (MIP, 50 µm). (11C) HCR spots detected per volume of expanded sample. Analysis was performed on samples which were either treated or not treated with FISH probes followed by HCR amplification. An automated spot counting algorithm was used to count HCR spots. The endogenous YFP protein was used to delineate regions used for the analysis. Plotted are mean±standard error. HCR spot counts are significantly different in the presence of probes than without probes ($p<0.05$ for both B1 and B2 amplifier sets, Welch's t-test; n=4 fields of view each). Scale bars: 50 µm.
Figure 11B:
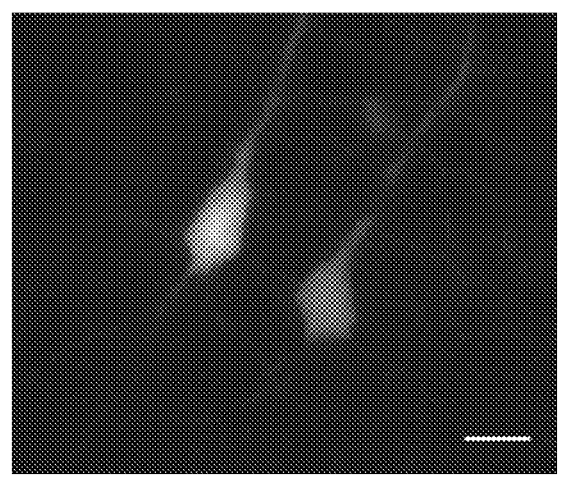
Figure 11C:
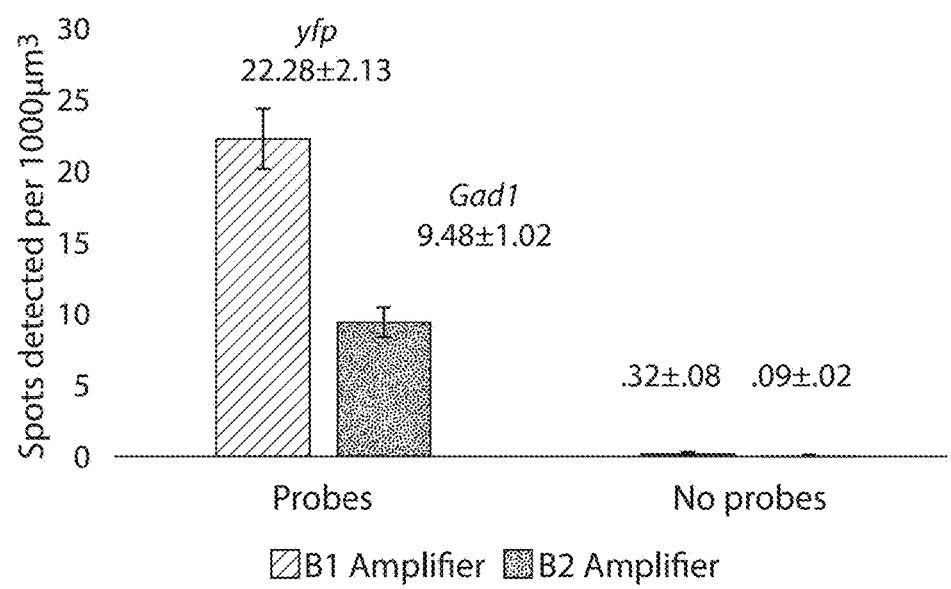
Figure 12A:
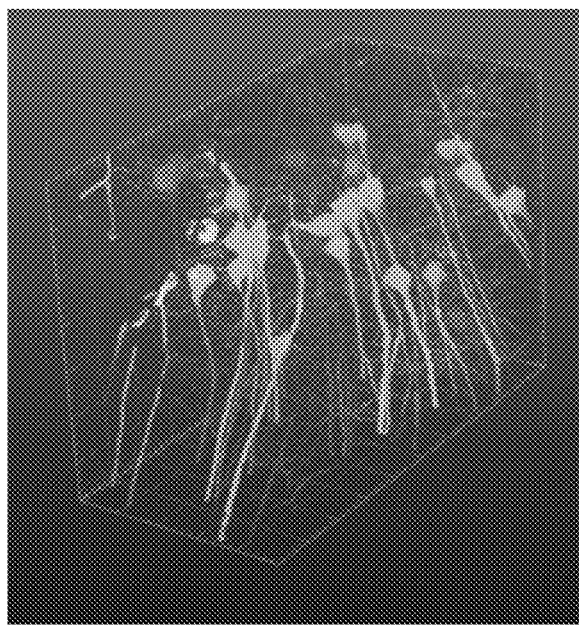
FIG. 12A-12C: (12A) Volume rendering of Thy1-YFP (green) brain tissue acquired by lightsheet microscopy with HCR-ExFISH targeting YFP (red) and Gad1 (blue) mRNA. (12B) A maximum intensity projection (~8 µm in Z) of a small subsection of the volume, showing the high resolution of imaging and single molecule localization of imaging expanded specimens with lightsheet imaging (scale bar: 10 µm, in pre-expansion units, expansion factor, 3×). (12C) Zoom in of the volume rendering in (12A) (scale bar: 20 µm, in pre-expansion units, 3×).
Figure 12B:
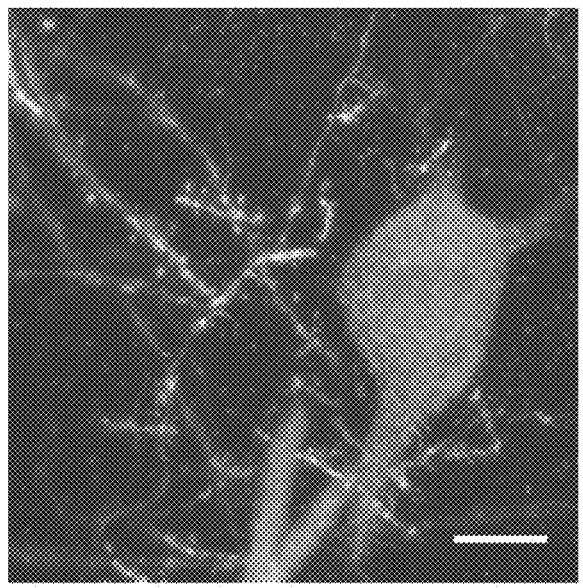
Figure 12C:
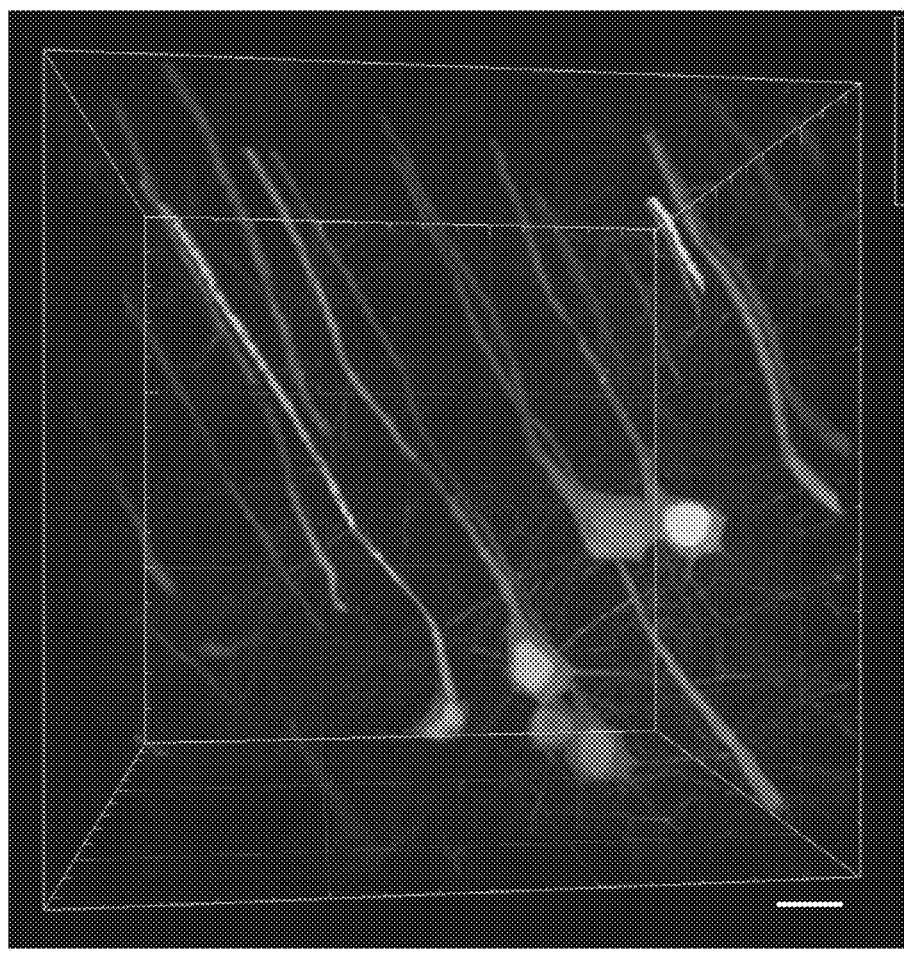

ExM allows for facile super-resolution imaging of thick 3-D specimens such as brain tissue on conventional microscopy hardware[1]. ExFISH was applied to samples of Thy1-YFP mouse brain tissue[21], using the YFP protein to delineate neural morphology (FIGS. 3A, 3B). Endogenous YFP protein was anchored to the polyacrylate gel via AcX using the proExM protocol[9], and RNA anchored via LabelX. Since smFISH yields signals too dim to visualize in intact tissues using confocal imaging, the previously described technique of hybridization chain reaction (HCR)[5] was applied, in particular the next-generation DNA HCR amplifier architecture[6] (schematic in FIG. 10). In samples containing mouse cortical and hippocampal regions, mRNAs for YFP (FIG. 3C) and glutamic acid decarboxylase 1 Gad1 (FIG. 3D) were easily visualized using a widefield microscope, with YFP mRNA well localized to YFP-fluorescing cells (FIG. 3E), and Gad1 mRNA localized to a population of cells with characteristic arrangement throughout specific layers of the cortex and hippocampus[22]. Examining brain specimens at high magnification using a confocal spinning disk microscope revealed that individual transcripts could be distinguished due to the physical magnification of ExM (FIG. 3F, with YFP and Gad1 mRNA highlighted), with even highly overexpressed transcripts (e.g., YFP) cleanly resolved into individual puncta (FIG. 3F). When FISH probes were omitted, minimal background HCR amplification was observed (FIGS. 11A-C). Given that ExM enables super-resolution imaging on diffraction limited microscopes, which can be scaled to very fast imaging speeds[23], we used a commercially available lightsheet microscope on a Thy1-YFP brain slice to enable visualization of multiple transcripts, with single molecule precision, throughout a volume of ~575 µm×575 µm×160 µm thick in just 3 hours (~6×10$^{10}$ voxels in 3 colors; FIGS. 12A-C).

Figure 10:
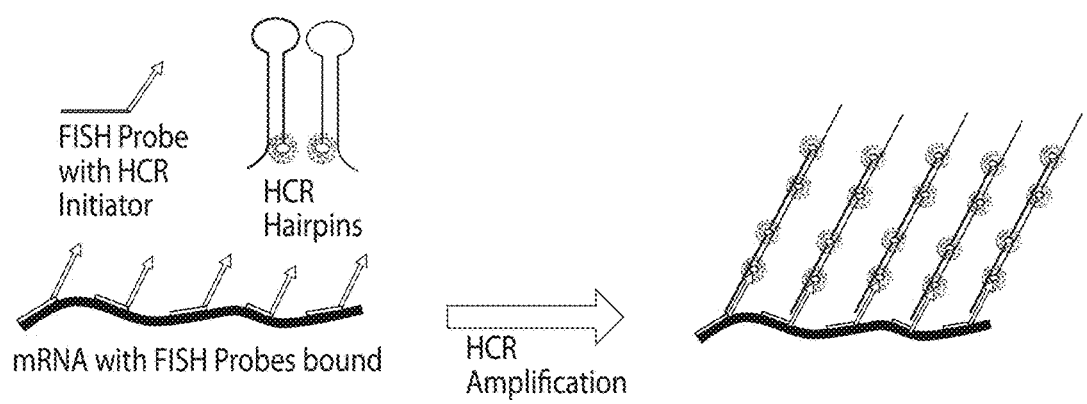
FIG. 10: FISH probes bearing HCR initiators are hybridized to a target mRNA. During amplification, metastable DNA hairpins bearing fluorophores assemble into polymer chains onto the initiators, thus amplifying signal downstream of the FISH probe hybridization event.
Figure 13A:
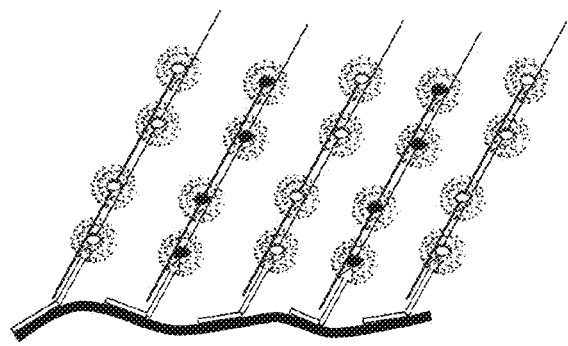
FIG. 13A-13G: (13A) Schematic showing two color amplification of the same target. A transcript of interest is targeted by probes against alternating parts of the sequence, and bearing two different HCR initiators, allowing for amplification in two colors. (13B) Confocal image showing FISH staining with HCR amplification against the Camk2a transcript in two colors (red and blue; YFP fluorescence shown in green). (13C) The result of an automated two-color spot co-localization analysis performed on the data set shown in (13B). Each purple spot represents a positive co-localization identified by the algorithm and overlaid on the confocal image of YFP. (13D, 13E) Zoom in of dendrites showing two color FISH staining with HCR amplification against Camk2a transcripts. (13F, 13G) As in (13D, 13E) but against Dlg4 transcripts. Top row shows the raw two color staining data corresponding to the bottom row showing co-localized spots identified by the automated algorithm. Scale bars: (13B, 13C) 10 µm (3×); (13D-13G) 2 µm (3×). (13B-13G) are MIP of ~1.6 µm thickness in unexpanded coordinates.
Figure 13B:
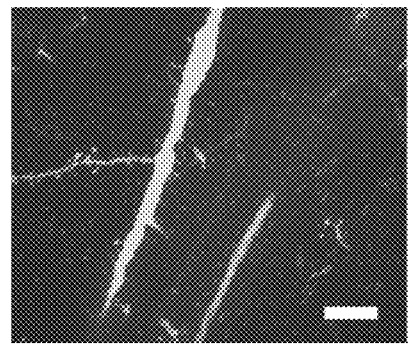
Figure 13C:
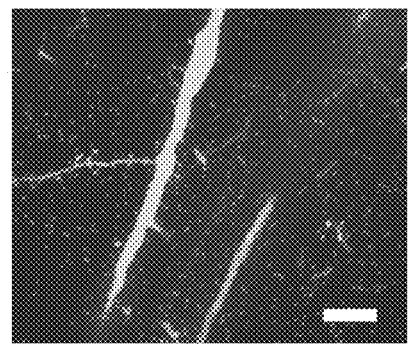
Figure 13D:
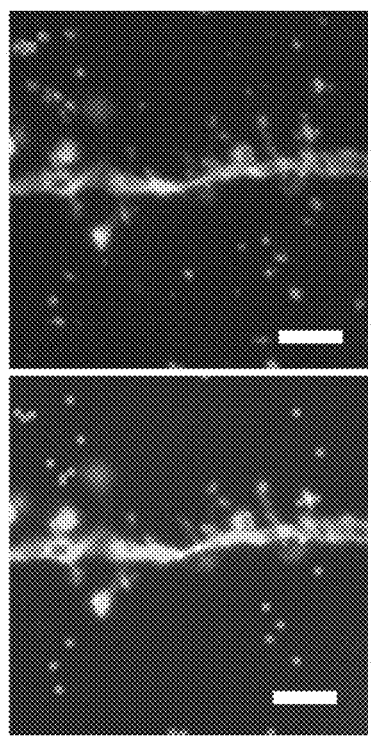
Figure 13E:
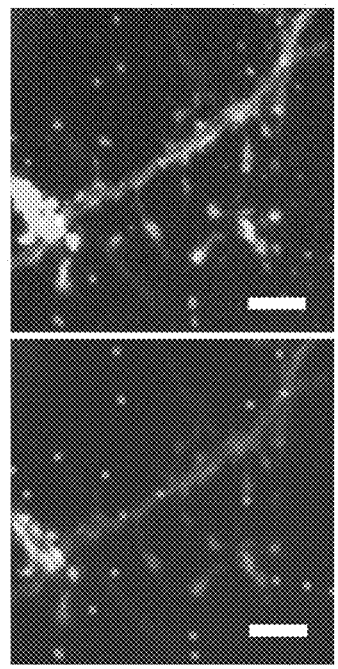
Figure 13F:
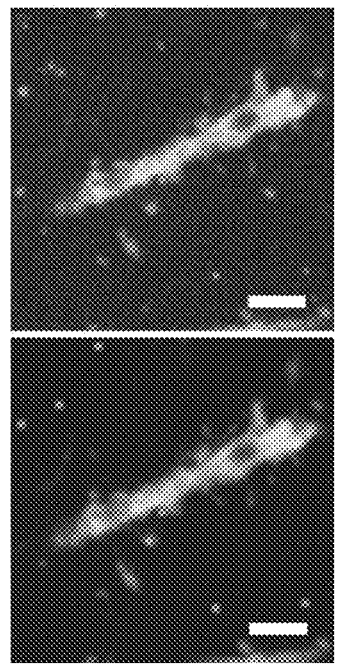
Figure 13G:
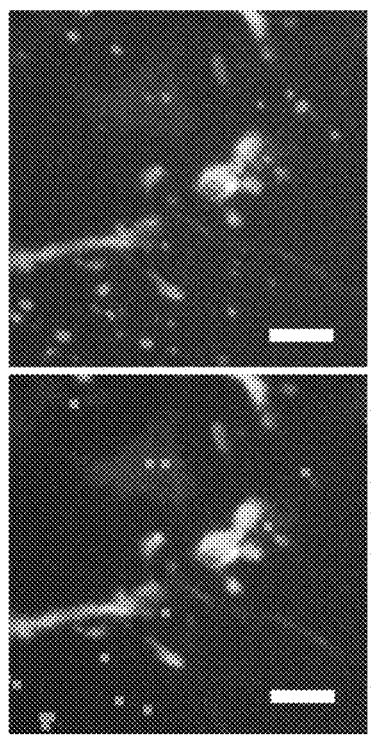

HCR amplifies a target binding event into a bright fluorescent signal (FIG. 10). A stringent method for assessing detection accuracy is to label individual RNAs with different probe sets bearing different colors[24,25], which shows that 50-80% of mRNAs thus targeted will be doubly labeled, when assessed in cell culture; a 50% co-localization is interpreted as $\sqrt{0.5}$~70% detection efficiency (assuming probe independence); this is a lower bound as it excludes false positives. In order to assess the false positive and negative rates for single molecule visualization in expanded tissues, pairs of probe sets targeting the same transcript with different initiators were delivered. This scheme results in amplified fluorescent signals of two different colors from the same target (FIGS. 13A-B), giving a measure of the hybridization efficiency. Delivering probe sets against a nonexistent transcript also gives a measure of false positive rate. A probe set was delivered against a missense probe (Dlg4 reversed, FIG. 3G(i-ii)) as well as a nonexistent transcript (mCherry, Table 3), using Thy1-YFP mouse brain samples, and found a low but nonzero spatial density of dim, yet amplified, puncta (1 per 61 µm$^3$ in unexpanded coordinates, Dlg4 reversed; 1 per 48 µm$^3$, mCherry). Essentially zero of these puncta exhibited co-localization (0/1,209 spots, Dlg4 reversed; 4/1,540 spots mCherry). In contrast, when a transcript was present (Actb), a large fraction of the puncta exhibited co-localization (an average of 58% of probes in one color co-localized with other color, 15,866/27,504 spots, FIG. 3H(i-ii), Table 3), indicative of a 75% detection efficiency, comparable to the non-amplified single molecule studies described above.

Figure 3I:
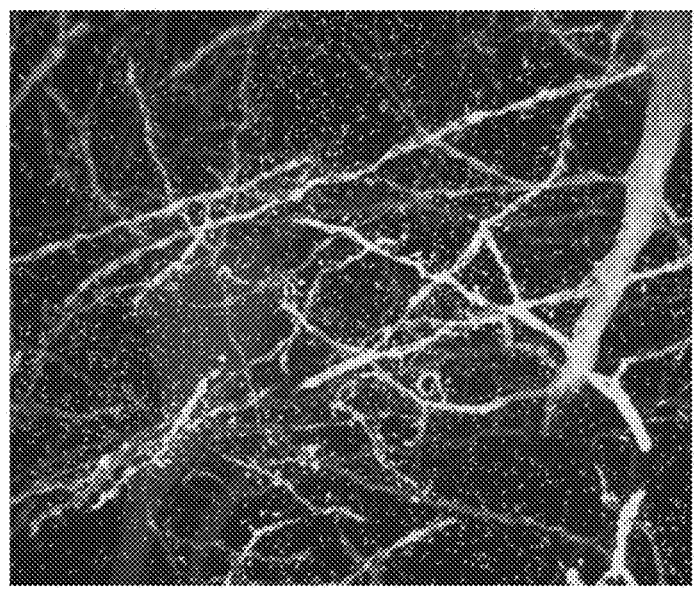
Figure 14A:
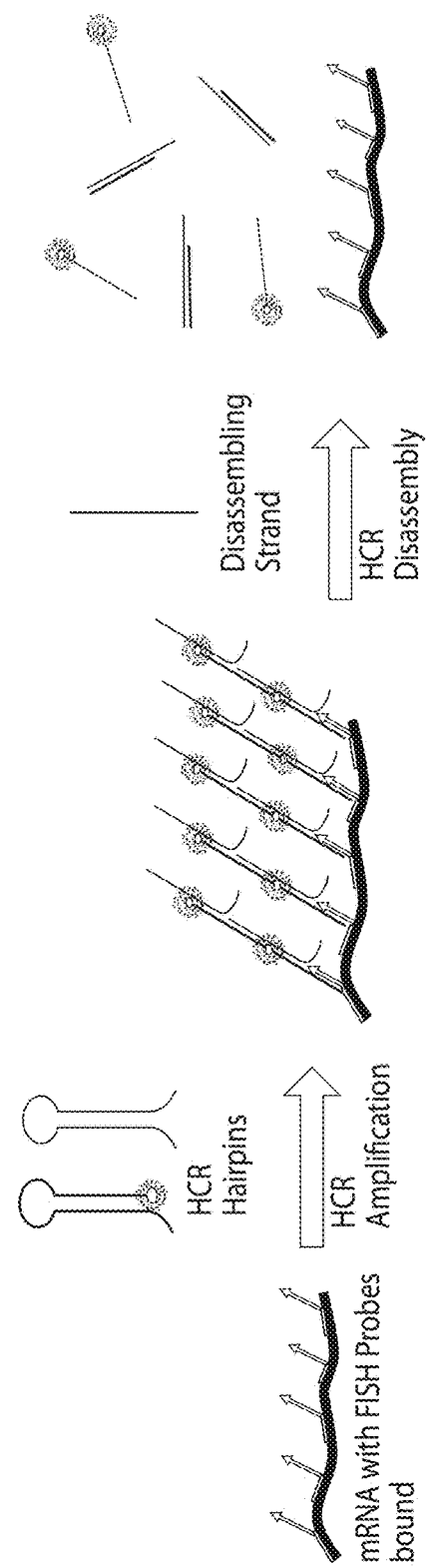
FIG. 14A-14B: (14A) Schematic for HCR amplification and reversal. HCR amplification is initiated with custom-made HCR hairpins bearing toe-holds for toe-hold mediated strand displacement. After amplification, the addition of a disassembling strand initiates the disassembly of the HCR polymers via strand displacement. (14B) ExFISH-treated Thy1-YFP brain slice (YFP in blue) is shown stained with YFP FISH probes bearing HCR initiators and amplified with custom made HCR hairpins bearing toe-holds for strand displacement (green dots). The different panels show the state of HCR reversal at different times after the addition of strands to initiate the disassembly of the HCR polymers. Scale bars: 20 µm (in post-expansion units).
Figure 14B:
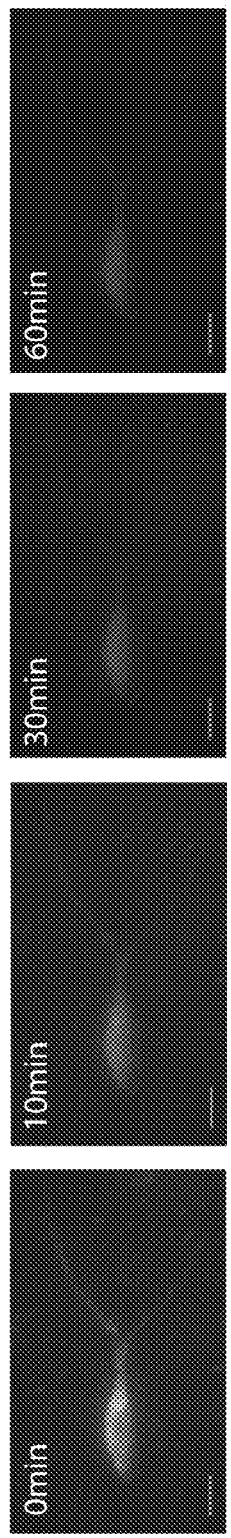

Two-color HCR ExFISH was used against mRNAs to image their position within cellular compartments such as dendritic spines, which require nanoscale resolution for accurate identification or segmentation. The Dlg4 mRNA was probed, which encodes the prominent postsynaptic scaffolding protein PSD-95, and which is known to be dendritically enriched[7]. A degree of co-localization (53%, 5,174/9,795 spots) was obtained, suggesting a high detection efficiency, 73% (FIG. 3I). The mRNA was also probed for Camk2a, finding a detection efficiency of 78% (co-localization, 61%, 8,799/14,440 spots, FIGS. 13D-E). Puncta which were co-localized were focused on, thus suppressing false positive errors, and giving a lower-bound on transcript detection (FIG. 13). Focusing on individual dendrites in these expanded samples revealed that individual Dlg4 (FIG. 3J(i-ii)) and Camk2a (FIG. 3K(i-ii)) mRNAs could indeed be detected in a sparse subset of dendritic spines as well as fine dendritic processes. To facilitate multiplexed HCR readout, we developed modified HCR hairpins that can be disassembled using toe-hold mediated strand displacement[26] (FIGS. 14A-B). These modified HCR amplifiers enable multiple cycles of HCR by disassembling the HCR polymer between subsequent cycles. Given that neurons can have tens of thousands of synapses, and mRNAs can be low copy number, the ability to map mRNAs at synapses throughout neuronal arbors may be useful for a diversity of questions in neuroscience ranging from plasticity to development to degeneration.

Discussion

A novel reagent, easily synthesized from commercial precursors, that enables RNA to be covalently anchored for expansion microscopy is presented. The resulting procedure, ExFISH, enables RNAs to be probed through single-molecule FISH labeling as well as hybridization chain reaction (HCR) amplification. RNA retention before versus after expansion was validated, finding excellent yield, and de-crowding of RNAs for more accurate RNA counts and localization. This enabled visualization, with nanoscale precision and single molecule resolution, RNA structures such as XIST and NEAT1, long non-coding RNAs whose emergent structure has direct implications for their biological roles. The anchoring was robust enough to support serial smFISH, including repeated washing and probe hybridization steps, and multiplexed readout of RNA identity and location, implying that using probes designed according to specific coding strategies[17-19] would support combinatorial multiplexing, in which each additional cycle yields exponentially more transcript information. The covalent anchoring of RNA to the ExM gel may also support enzymatic reactions to be performed in expanded samples—such as reverse transcription, rolling circle amplification (RCA), fluorescent in situ sequencing (FISSEQ)[27], and other strategies for transcriptomic readout or SNP detection[28], within intact samples.

ExM, being a physical form of magnification, enables nanoscale resolution even on conventional diffraction limited microscopes. Expanding samples makes them transparent and homogeneous in index of refraction, in part because of the volumetric dilution, and in part because of washout of non-anchored components[1]. Thus, strategies combining ExM with fast diffraction limited methods like lightsheet microscopy[23] may result in "best of both worlds" performance metrics: the voxel sizes of classical super-resolution methods, but the voxel acquisition rates of increasingly fast diffraction limited microscopes[1]. The de-crowding of RNAs enables another key advantage: reducing the effective size of the self-assembled amplification product of HCR, which were applied here, following the protocols of refs.[5,6], to enable nanoscale resolution visualization of RNA in intact tissues (a paper conducted in parallel has also recently performed single molecule HCR FISH[29]). An HCR amplicon of size 500 nm in the post-expanded sample would, because of the greater distance between RNAs, have an effective size of 500/3.5=~150 nm. The lower packing density of amplicons facilitates the imaging of more transcripts per experiment[19] with nanoscale precision. Other methods of achieving brighter signals may be possible. For example, brighter fluorophores such as quantum dots[30] or bottlebrush fluorophores[31] could obviate the need for signal amplification, in principle. The expanded state may enable better delivery of these and other bulky fluorophores into samples. Other amplification strategies may be possible as well, including enzymatic (e.g., RCA[28], tyramide amplification[22], HRP amplification) as well as nonenzymatic (e.g., branched DNA) methods, although reaction efficiency and diffusion of reagents into the sample must be considered.

ExFISH may find many uses in neuroscience and other biological fields. In the brain, for example, RNA is known to be trafficked to specific synapses as a function of local synaptic activity[32] and intron content[33], and locally translated[7,34,35], and the presence and translation of axonal RNAs remains under investigation[36]. It is anticipated that, coupled to straightforward multiplexed coding schemes, this method can be used for transcriptomic profiling of neuronal cell-types in situ, as well as for the super-resolved characterization of neuronal connectivity and synaptic organization in intact brain circuits, key for an integrative understanding of the mechanisms of neural circuit function and dysfunction. More broadly, visualizing RNAs within cells, and their relationship with RNA processing and trafficking machinery, may reveal new insights throughout biology and medicine.

Method Information

TABLE 1

List of reagents and suppliers

| Chemical Supplies | Chemical Name | Supplier | Part Number |
|---|---|---|---|
| ExM Gel or Preparation | Sodium Acrylate (purity note:*) | Sigma | 408220 |
| | Acrylamide | Sigma | A9099 |
| | N,N'-Methylenebisacrylamide | Sigma | M7279 |
| | Ammonium Persulfate | Sigma | A3678 |
| | N,N,N',N'-Tetramethylethylenediamine | Sigma | T7024 |
| | VA-044 | Wako | 27776-21-2 |
| | 4-Hydroxy-TEMPO | Sigma | 176141 |
| Hybridization Buffer | Dextran Sulfate | Sigma | D8906-50g |
| | SSC | Thermo Fisher | AM9765 |
| | Formamide | Thermo Fisher | AM9342 |
| Fixation and Permeabilization | Paraformaldehyde | Electron Microscopy | 15710 |
| | Tissue-prep Buffered 10% Formalin | Electron Microscopy | 15742-10 |
| | Triton X-100 | Sigma | 93426 |
| | Ethyl Alcohol | Sigma | E7023 |
| | Glycine | Sigma | 50046 |
| | 10x PBS | Thermo Fisher | AM9624 |
| Protein Digestion | Proteinase K | New England Biolabs | P8107S |
| | Ethylenediaminetetraacetic acid | Sigma | EDS |
| | Sodium Chloride | Sigma | S9888 |
| | Tris-HCl | Life | AM9855 |
| HCR Amplification | Amplification Buffer | Molecular Instruments | N/A |
| | Tween 20 | Sigma | P1379 |
| LabelX Preparation | LABEL-IT ® Amine Acryloyl-X, SE | Mirus Bio Thermo Fisher | MIR 3900 A20770 |
| LabelX Treatment | MOPS | Sigma | M9381-25G |
| Reembeded Gels | DNAse I | Sigma | 4716728001 |
| Bind-silane | Bind-Silane | Sigma | GE17-1330-01 |

*check for yellow color upon resuspension: that indicates poor quality; solution should be clear (see http://expansionmicroscopy.org)

TABLE 2

| Decades (Transcript Abundance) | Mean (Ratio of # spots detected in individual cells after ExM, to # spots detected before ExM) | Standard Deviation | Sample size (n) | p-Value |
|---|---|---|---|---|
| 10 s | 1.082 | 0.177 | 14 | 0.107 |
| 100 s | 1.105 | 0.138 | 29 | $3.24 \times 10^{-4}$ |
| 1000 s | 1.596 | 0.562 | 16 | $7.09 \times 10^{-4}$ |

TABLE 3

| Tar | Total Spot Count (Averaged Across | Co- | Co- | Hybridization | Volume analyzed ($\mu m^3$ in | Density (Co-localized Puncta per |
|---|---|---|---|---|---|---|
| ActB | 27504 | | 15866 | | 0.577 | |
| | | 0.76 | | 236749 | 0.067 | |
| Dlg4 | 9795 | | 5174 | | 0.528 | |
| | | 0.727 | | 236749 | 0.022 | |
| Camk2a | 14440 | | 8799 | | 0.609 | |

| Accession | Probe Sequence | Initiator Type |
|---|---|---|
| YFP B1 1 | gAggAgggCAgCAAACgggAAgAgTCTTCCTTTACgTAATctcgcccttgct caccat (SEQ ID NO.: 1) | B1 |
| YFP B1 2 | gAggAgggCAgCAAACgggAAgAgTCTTCCTTTACgTAATcaccaccccggt gaacag (SEQ ID NO.: 2) | B1 |
| YFP B1 3 | gAggAgggCAgCAAACgggAAgAgTCTTCCTTTACgTAATccagctcgacc aggatg (SEQ ID NO.: 3) | B1 |
| YFP B1 4 | gAggAgggCAgCAAACgggAAgAgTCTTCCTTTACgTAATtgtggccgttta cgtcgc (SEQ ID NO.: 4) | B1 |
| YFP B1 5 | gAggAgggCAgCAAACgggAAgAgTCTTCCTTTACgTAATctcgccggacac gctgaa (SEQ ID NO.: 5) | B1 |
| YFP B1 6 | gAggAgggCAgCAAACgggAAgAgTCTTCCTTTACgTAATtaggtggcatcg ccctcg (SEQ ID NO.: 6) | B1 |
| YFP B1 7 | gAggAgggCAgCAAACgggAAgAgTCTTCCTTTACgTAATacttcagggtca gcttgc (SEQ ID NO.: 7) | B1 |
| YFP B1 8 | gAggAgggCAgCAAACgggAAgAgTCTTCCTTTACgTAATcttgccggtggt gcagat (SEQ ID NO.: 8) | B1 |
| YFP B1 9 | gAggAgggCAgCAAACgggAAgAgTCTTCCTTTACgTAATgtgggccagggc acgggc (SEQ ID NO.: 9) | B1 |
| YFP B1 10 | gAggAgggCAgCAAACgggAAgAgTCTTCCTTTACgTAATagccgaaggtgg tcacga (SEQ ID NO.: 10) | B1 |
| YFP B1 11 | gAggAgggCAgCAAACgggAAgAgTCTTCCTTTACgTAATggcgaagcactg caggcc (SEQ ID NO.: 11) | B1 |
| YFP B1 12 | gAggAgggCAgCAAACgggAAgAgTCTTCCTTTACgTAATttcatgtggtcg gggtag (SEQ ID NO.: 12) | B1 |
| YFP B1 13 | gAggAgggCAgCAAACgggAAgAgTCTTCCTTTACgTAATacttgaagaagt cgtgct (SEQ ID NO.: 13) | B1 |

-continued

| | | |
|---|---|---|
| YFP B1 14 | gAggAgggCAgCAAACgggAAgAgTCTTCCTTTACgTAATgtagccttcggg catggc (SEQ ID NO.: 14) | B1 |
| YFP B1 15 | gAggAgggCAgCAAACgggAAgAgTCTTCCTTTACgTAATaagatggtgcgc tcctgg (SEQ ID NO.: 15) | B1 |
| YFP B1 16 | gAggAgggCAgCAAACgggAAgAgTCTTCCTTTACgTAATagttgccgtcgt ccttga (SEQ ID NO.: 16) | B1 |
| YFP B1 17 | gAggAgggCAgCAAACgggAAgAgTCTTCCTTTACgTAATcacctcggcgcg ggtctt (SEQ ID NO.: 17) | B1 |
| YFP B1 18 | gAggAgggCAgCAAACgggAAgAgTCTTCCTTTACgTAATagggtgtcgccc tcgaac (SEQ ID NO.: 18) | B1 |
| YFP B1 19 | gAggAgggCAgCAAACgggAAgAgTCTTCCTTTACgTAATtcagctcgatgc ggttca (SEQ ID NO.: 19) | B1 |
| YFP B1 20 | gAggAgggCAgCAAACgggAAgAgTCTTCCTTTACgTAATctccttgaagtc gatgcc (SEQ ID NO.: 20) | B1 |
| YFP B1 21 | gAggAgggCAgCAAACgggAAgAgTCTTCCTTTACgTAATtgccccaggatg ttgccg (SEQ ID NO.: 21) | B1 |
| YFP B1 22 | gAggAgggCAgCAAACgggAAgAgTCTTCCTTTACgTAATtgtagttgtact ccagct (SEQ ID NO.: 22) | B1 |
| YFP B1 23 | gAggAgggCAgCAAACgggAAgAgTCTTCCTTTACgTAATgatatagacgtt gtggct (SEQ ID NO.: 23) | B1 |
| YFP B1 24 | gAggAgggCAgCAAACgggAAgAgTCTTCCTTTACgTAATttcttctgcttg tcggcc (SEQ ID NO.: 24) | B1 |
| YFP B1 25 | gAggAgggCAgCAAACgggAAgAgTCTTCCTTTACgTAATtgaagttcacct tgatgc (SEQ ID NO.: 25) | B1 |
| YFP B1 26 | gAggAgggCAgCAAACgggAAgAgTCTTCCTTTACgTAATctcgatgttgtg gcggat (SEQ ID NO.: 26) | B1 |
| YFP B1 27 | gAggAgggCAgCAAACgggAAgAgTCTTCCTTTACgTAATgcgagctgcacg ctgccg (SEQ ID NO.: 27) | B1 |
| YFP B1 28 | gAggAgggCAgCAAACgggAAgAgTCTTCCTTTACgTAATtgttctgctggt agtggt (SEQ ID NO.: 28) | B1 |
| YFP B1 29 | gAggAgggCAgCAAACgggAAgAgTCTTCCTTTACgTAATggggccgtcgcc gatggg (SEQ ID NO.: 29) | B1 |
| YFP B1 30 | gAggAgggCAgCAAACgggAAgAgTCTTCCTTTACgTAATtggttgtcgggc agcagc (SEQ ID NO.: 30) | B1 |
| YFP B1 31 | gAggAgggCAgCAAACgggAAgAgTCTTCCTTTACgTAATcggactggtagc tcaggt (SEQ ID NO.: 31) | B1 |
| YFP B1 32 | gAggAgggCAgCAAACgggAAgAgTCTTCCTTTACgTAATgttggggtcttt gctcag (SEQ ID NO.: 32) | B1 |
| YFP B1 33 | gAggAgggCAgCAAACgggAAgAgTCTTCCTTTACgTAATaccatgtgatcg cgcttc (SEQ ID NO.: 33) | B1 |
| YFP B1 34 | gAggAgggCAgCAAACgggAAgAgTCTTCCTTTACgTAATcggtcacgaact ccagca (SEQ ID NO.: 34) | B1 |
| YFP B1 35 | gAggAgggCAgCAAACgggAAgAgTCTTCCTTTACgTAATgccgagagtgat cccggc (SEQ ID NO.: 35) | B1 |
| YFP B1 36 | gAggAgggCAgCAAACgggAAgAgTCTTCCTTTACgTAATtacttgtacagc tcgtcc (SEQ ID NO.: 36) | B1 |
| Gad1 21 | TTGAAAAATCGAGGGTGACCTGAAAgCTCAgTCCATCCTCgTAAATCCTCAT CAATCATC (SEQ ID NO.: 37) | B2 |
| Gad1 22 | CCAATGATATCCAAACCAGTAGAAgCATTCTTTCTTgAggAgggCAgCAAAC gggAAgAg (SEQ ID NO.: 38) | B1 |
| Gad1 23 | GATGTCAGCCATTCACCAGCTAAAAgCTCAgTCCATCCTCgTAAATCCTCAT CAATCATC (SEQ ID NO.: 39) | B2 |
| Gad1 24 | TCATATGTGAACATATTGGTATAAgCATTCTTTCTTgAggAgggCAgCAAAC gggAAgAg (SEQ ID NO.: 40) | B1 |
| Gad1 25 | ATGAGAACAAACACGGGTGCAAAAgCTCAgTCCATCCTCgTAAATCCTCAT CAATCATC (SEQ ID NO.: 41) | B2 |
| Gad1 26 | TCTCTCATCTTCTTAAGAGTAAAAgCATTCTTTCTTgAggAgggCAgCAAAC gggAAgAg (SEQ ID NO.: 42) | B1 |
| Gad1 27 | TCTTTATTTGACCATCCAACGAAAAgCTCAgTCCATCCTCgTAAATCCTCAT CAATCATC (SEQ ID NO.: 43) | B2 |
| Gad1 28 | GCTCCCCCAGGAGAAAATATCCAAgCATTCTTTCTTgAggAgggCAgCAAAC gggAAgAg (SEQ ID NO.: 44) | B1 |
| Gad1 29 | ATGATGCTGTACATATTGGATAAAAgCTCAgTCCATCCTCgTAAATCCTCAT CAATCATC (SEQ ID NO.: 45) | B2 |
| Gad1 30 | ACTTCTGGGAAGTACTTGTAACAAgCATTCTTTCTTgAggAgggCAgCAAAC gggAAgAg (SEQ ID NO.: 46) | B1 |
| Gad1 31 | ACAGCCGCCATGCCTTTTGTCTAAAgCTCAgTCCATCCTCgTAAATCCTCAT CAATCATC (SEQ ID NO.: 47) | B2 |
| Gad1 32 | TGTTCTGAGGTGAAGAGGACCAAgCATTCTTTCTTgAggAgggCAgCAAAC gggAAgAg (SEQ ID NO.: 48) | B1 |
| Gad1 33 | GCTTTCTTTATGGAATAGTGACAAAgCTCAgTCCATCCTCgTAAATCCTCAT CAATCATC (SEQ ID NO.: 49) | B2 |
| Gad1 34 | TTGTCGGTTCCAAAGCCAAGCGAAgCATTCTTTCTTgAggAgggCAgCAAAC gggAAgAg (SEQ ID NO.: 50) | B1 |
| Gad1 35 | TCATTGCACTTTATCAAAATCAAAgCTCAgTCCATCCTCgTAAATCCTCAT CAATCATC (SEQ ID NO.: 51) | B2 |
| Gad1 36 | TCTAAATCAGCCGGAATTATCTAAgCATTCTTTCTTgAggAgggCAgCAAAC gggAAgAg (SEQ ID NO.: 52) | B1 |

| | | |
|---|---|---|
| Gad1 37 | TGTTTGGCATCAAGAATTTTTGAAAgCTCAgTCCATCCTCgTAAATCCTCAT CAATCATC (SEQ ID NO.: 53) | B2 |
| Gad1 38 | GCATTGACATAAAGGGGAACATAAgCATTCTTTCTTgAggAgggCAgCAAAC gggAAgAg (SEQ ID NO.: 54) | B1 |
| Gad1 39 | CCGTAAACAGTCGTGCCTGCGGAAAgCTCAgTCCATCCTCgTAAATCCTCAT CAATCATC (SEQ ID NO.: 55) | B2 |
| Gad1 40 | TCCGCAATTTCCTGGATTGGATAAgCATTCTTTCTTgAggAgggCAgCAAAC gggAAgAg (SEQ ID NO.: 56) | B1 |
| Gad1 41 | CAAAGGTTGTATTTCTCACATAAAAgCTCAgTCCATCCTCgTAAATCCTCAT CAATCATC (SEQ ID NO.: 57) | B2 |
| Gad1 42 | CCACCACCCCAGGCAGCATCCAAAgCATTCTTTCTTgAggAgggCAgCAAAC gggAAgAg (SEQ ID NO.: 58) | B1 |
| Gad1 43 | CGGTGCTTCCGGGACATGAGCAAAAgCTCAgTCCATCCTCgTAAATCCTCAT CAATCATC (SEQ ID NO.: 59) | B2 |
| Gad1 44 | TTGGCCCTTTCTATGCCGCTGAAAgCATTCTTTCTTgAggAgggCAgCAAAC gggAAgAg (SEQ ID NO.: 60) | B1 |
| Gad1 45 | TTGTGAGGGTTCCAGGTGACTGAAAgCTCAgTCCATCCTCgTAAATCCTCAT CAATCATC (SEQ ID NO.: 61) | B2 |
| Gad1 46 | GCAGAGCACTGGAGCAGCACGCAAgCATTCTTTCTTgAggAgggCAgCAAAC gggAAgAg (SEQ ID NO.: 62) | B1 |
| Gad1 47 | ATACCCTTTTCCTTGACCAGAAAAgCTCAgTCCATCCTCgTAAATCCTCAT CAATCATC (SEQ ID NO.: 63) | B2 |
| Gad1 48 | CCTGCACACATCTGGTTGCATCAAgCATTCTTTCTTgAggAgggCAgCAAAC gggAAgAg (SEQ ID NO.: 64) | B1 |
| ActB B2 2 | CCTCgTAAATCCTCATCAATCATCCAgTAAACCgCCAAggaatacagcccgg ggagcatc (SEQ ID NO.: 65) | B2 |
| ActB B2 4 | CCTCgTAAATCCTCATCAATCATCCAgTAAACCgCCAAcacccacataggag tccttctg (SEQ ID NO.: 66) | B2 |
| ActB B2 6 | CCTCgTAAATCCTCATCAATCATCCAgTAAACCgCCAAcaatggggtacttc agggtcag (SEQ ID NO.: 67) | B2 |
| ActB B2 8 | CCTCgTAAATCCTCATCAATCATCCAgTAAACCgCCAAggtgccagatcttc tccatgtc (SEQ ID NO.: 68) | B2 |
| ActB B2 10 | CCTCgTAAATCCTCATCAATCATCCAgTAAACCgCCAAtcatcttttcacgg ttggcctt (SEQ ID NO.: 69) | B2 |
| ActB B2 12 | CCTCgTAAATCCTCATCAATCATCCAgTAAACCgCCAAtggctacgtacatg gctgggt (SEQ ID NO.: 70) | B2 |
| ActB B2 14 | CCTCgTAAATCCTCATCAATCATCCAgTAAACCgCCAAcaatgcctgtggta cgaccaga (SEQ ID NO.: 71) | B2 |
| ActB B2 16 | CCTCgTAAATCCTCATCAATCATCCAgTAAACCgCCAAcctcgtagatgggc acagtgtg (SEQ ID NO.: 72) | B2 |
| ActB B2 18 | CCTCgTAAATCCTCATCAATCATCCAgTAAACCgCCAAatcttcatgaggta gtctgtca (SEQ ID NO.: 73) | B2 |
| ActB B2 20 | CCTCgTAAATCCTCATCAATCATCCAgTAAACCgCCAAatttccctctcagc tgtggtgg (SEQ ID NO.: 74) | B2 |
| ActB B2 22 | CCTCgTAAATCCTCATCAATCATCCAgTAAACCgCCAAtcgaagtctagagc aacatagc (SEQ ID NO.: 75) | B2 |
| ActB B2 24 | CCTCgTAAATCCTCATCAATCATCCAgTAAACCgCCAAtagctcttctccag ggaggaag (SEQ ID NO.: 76) | B2 |
| ActB B2 26 | CCTCgTAAATCCTCATCAATCATCCAgTAAACCgCCAAggaaccgctcgtt gccaatag (SEQ ID NO.: 77) | B2 |
| ActB B2 28 | CCTCgTAAATCCTCATCAATCATCCAgTAAACCgCCAAcaggattccatacc caagaagg (SEQ ID NO.: 78) | B2 |
| ActB B2 30 | CCTCgTAAATCCTCATCAATCATCCAgTAAACCgCCAAtcaacgtcacactt catgatgg (SEQ ID NO.: 79) | B2 |
| ActB B2 32 | CCTCgTAAATCCTCATCAATCATCCAgTAAACCgCCAAgtggtaccaccaga cagcactg (SEQ ID NO.: 80) | B2 |
| ActB B2 34 | CCTCgTAAATCCTCATCAATCATCCAgTAAACCgCCAAagagcagtaatctc cttctgca (SEQ ID NO.: 81) | B2 |
| ActB B2 36 | CCTCgTAAATCCTCATCAATCATCCAgTAAACCgCCAAttgcgctcaggag agcaatga (SEQ ID NO.: 82) | B2 |
| ActB B2 38 | CCTCgTAAATCCTCATCAATCATCCAgTAAACCgCCAAaaggtggacagtga ggccagga (SEQ ID NO.: 83) | B2 |
| ActB B2 40 | CCTCgTAAATCCTCATCAATCATCCAgTAAACCgCCAAgaggggccggactc atcgtact (SEQ ID NO.: 84) | B2 |
| Act Short HCR 1 | gAggAgggCAgCAAACgggAAgAgTCTTCCTTTACgTTgcgcagcgatatcg tcatccat (SEQ ID NO.: 85) | B1 |
| Act Short HCR 3 | gAggAgggCAgCAAACgggAAgAgTCTTCCTTTACgTTccattcccaccatc acaccctg (SEQ ID NO.: 86) | B1 |
| Act Short HCR 5 | gAggAgggCAgCAAACgggAAgAgTCTTCCTTTACgTTacctctcttgctc tgggcctc (SEQ ID NO.: 87) | B1 |
| Act Short HCR 7 | gAggAgggCAgCAAACgggAAgAgTCTTCCTTTACgTTcccagttggtaaca atgccatg (SEQ ID NO.: 88) | B1 |
| Act Short HCR 9 | gAggAgggCAgCAAACgggAAgAgTCTTCCTTTACgTTcacgcagctcattg tagaaggt (SEQ ID NO.: 89) | B1 |
| Act Short HCR 11 | gAggAgggCAgCAAACgggAAgAgTCTTCCTTTACgTTgaaggtctcaaac atgatctg (SEQ ID NO.: 90) | B1 |

| | | |
|---|---|---|
| Act Short HCR 13 | gAggAgggCAgCAAACgggAAgAgTCTTCCTTTACgTTcatacagggacagc acagcctg (SEQ ID NO.: 91) | B1 |
| Act Short HCR 15 | gAggAgggCAgCAAACgggAAgAgTCTTCCTTTACgTTtgaccccgtctccg gagtccat (SEQ ID NO.: 92) | B1 |
| Act Short HCR 17 | gAggAgggCAgCAAACgggAAgAgTCTTCCTTTACgTTggatggcgtgaggg agagcata (SEQ ID NO.: 93) | B1 |
| Act Short HCR 19 | gAggAgggCAgCAAACgggAAgAgTCTTCCTTTACgTTaagctgtagccacg ctcggtca (SEQ ID NO.: 94) | B1 |
| Act Short HCR 21 | gAggAgggCAgCAAACgggAAgAgTCTTCCTTTACgTTagcttctctttgat gtcacgca (SEQ ID NO.: 95) | B1 |
| Act Short HCR 23 | gAggAgggCAgCAAACgggAAgAgTCTTCCTTTACgTTgatgcggcagtggc catctcct (SEQ ID NO.: 96) | B1 |
| Act Short HCR 25 | gAggAgggCAgCAAACgggAAgAgTCTTCCTTTACgTTatgacctggccgtc aggcagct (SEQ ID NO.: 97) | B1 |
| Act Short HCR 27 | gAggAgggCAgCAAACgggAAgAgTCTTCCTTTACgTTggctggaaaagagc ctcagggc (SEQ ID NO.: 98) | B1 |
| Act Short HCR 29 | gAggAgggCAgCAAACgggAAgAgTCTTCCTTTACgTTttgaatgtagtttc atggatgc (SEQ ID NO.: 99) | B1 |
| Act Short HCR 31 | gAggAgggCAgCAAACgggAAgAgTCTTCCTTTACgTTtggcatagaggtc tttacgga (SEQ ID NO.: 100) | B1 |
| Act Short HCR 33 | gAggAgggCAgCAAACgggAAgAgTCTTCCTTTACgTTctgtcagcaatgcc tgggtaca (SEQ ID NO.: 101) | B1 |
| Act Short HCR 35 | gAggAgggCAgCAAACgggAAgAgTCTTCCTTTACgTTtgatcttcatggt gctaggag (SEQ ID NO.: 102) | B1 |
| Act Short HCR 37 | gAggAgggCAgCAAACgggAAgAgTCTTCCTTTACgTTgagccaccgatcca cacagagt (SEQ ID NO.: 103) | B1 |
| Act Short HCR 39 | gAggAgggCAgCAAACgggAAgAgTCTTCCTTTACgTTgcttgctgatcca catctgct (SEQ ID NO.: 104) | B1 |
| Act Short HCR 41 | gAggAgggCAgCAAACgggAAgAgTCTTCCTTTACgTTagaagcacttgcg gtgcacga (SEQ ID NO.: 105) | B1 |
| Act Short HCR 41 | gAggAgggCAgCAAACgggAAgAgTCTTCCTTTACgTTagaagcacttgcg gtgcacga (SEQ ID NO.: 106) | B1 |
| DLG4 B1 2 | GGGCTGTGTTCCAGAGGGGCGAAgCATTCTTTCTTgAggAgggCAgCAAAC gggAAgAg (SEQ ID NO.: 107) | B1 |
| DLG4 B1 4 | GTGTCCGTGTTGACAATCACAGAAgCATTCTTTCTTgAggAgggCAgCAAAC gggAAgAg (SEQ ID NO.: 108) | B1 |
| DLG4 B1 6 | TCCTCATACTCCATCTCCCCCTAAgCATTCTTTCTTgAggAgggCAgCAAAC gggAAgAg (SEQ ID NO.: 109) | B1 |
| DLG4 B1 8 | GTGCCACCTGCGATGCTGAAGCAAgCATTCTTTCTTgAggAgggCAgCAAAC gggAAgAg (SEQ ID NO.: 110) | B1 |
| DLG4 B1 10 | GGAATGATCTTGGTGATAAAGAAAgCATTCTTTCTTgAggAgggCAgCAAAC gggAAgAg (SEQ ID NO.: 111) | B1 |
| DLG4 B1 12 | AACAGGATGCTGTCGTTGACCCAAgCATTCTTTCTTgAggAgggCAgCAAAC gggAAgAg (SEQ ID NO.: 112) | B1 |
| DLG4 B1 14 | AGGGCCTCCACTGCAGCTGAATAAgCATTCTTTCTTgAggAgggCAgCAAAC gggAAgAg (SEQ ID NO.: 113) | B1 |
| DLG4 B1 16 | GCTGGGGTTTCCGGCGCATGAAAgCATTCTTTCTTgAggAgggCAgCAAAC gggAAgAg (SEQ ID NO.: 114) | B1 |
| DLG4 B1 18 | CTGAAGCCAAGTCCTTTAGGCCAAgCATTCTTTCTTgAggAgggCAgCAAAC gggAAgAg (SEQ ID NO.: 115) | B1 |
| DLG4 B1 20 | ACGTAGATGCTATTATCTCCAGAAgCATTCTTTCTTgAggAgggCAgCAAAC gggAAgAg (SEQ ID NO.: 116) | B1 |
| DLG4 B1 22 | CCGATCTGCAACCTGCCATCCTAAgCATTCTTTCTTgAggAgggCAgCAAAC gggAAgAg (SEQ ID NO.: 117) | B1 |
| DLG4 B1 24 | TCCTCATGCATGACATCCTCTAAAgCATTCTTTCTTgAggAgggCAgCAAAC gggAAgAg (SEQ ID NO.: 118) | B1 |
| DLG4 B1 26 | TTGGCCACCTTTAGGTACACAAAAgCATTCTTTCTTgAggAgggCAgCAAAC gggAAgAg (SEQ ID NO.: 119) | B1 |
| DLG4 B1 28 | GAGGTTGTGATGTCTGGGGGAGAAgCATTCTTTCTTgAggAgggCAgCAAAC gggAAgAg (SEQ ID NO.: 120) | B1 |
| DLG4 B1 30 | TCGGTGCCCAAGTAGCTGCTATAAgCATTCTTTCTTgAggAgggCAgCAAAC gggAAgAg (SEQ ID NO.: 121) | B1 |
| DLG4 B2 1 | TCTTCATCTTGGTAGCGGTATTAAAgCTCAgTCCATCCTCgTAAATCCTCAT CAATCATC (SEQ ID NO.: 122) | B2 |
| DLG4 B2 3 | GGAGAATTGGCCTGGTTGGGGAAAAgCTCAgTCCATCCTCgTAAATCCTCAT CAATCATC (SEQ ID NO.: 123) | B2 |
| DLG4 B2 5 | GTTCCGTTCACATATCCTGGGGAAAgCTCAgTCCATCCTCgTAAATCCTCAT CAATCATC (SEQ ID NO.: 124) | B2 |
| DLG4 B2 7 | AGACCTGAGTTACCCCTTTCCAAAAgCTCAgTCCATCCTCgTAAATCCTCAT CAATCATC (SEQ ID NO.: 125) | B2 |
| DLG4 B2 9 | GATGGGTCGTCACCGATGTGAAAgCTCAgTCCATCCTCgTAAATCCTCAT CAATCATC (SEQ ID NO.: 126) | B2 |
| DLG4 B2 11 | AGGCGGCCATCCTGGGCTGCAGAAgCTCAgTCCATCCTCgTAAATCCTCAT CAATCATC (SEQ ID NO.: 127) | B2 |
| DLG4 B2 13 | GTCACCTCCCGGACATCCACTTAAgCTCAgTCCATCCTCgTAAATCCTCAT CAATCATC (SEQ ID NO.: 128) | B2 |

| | | |
|---|---|---|
| DLG4 B2 15 | TAGAGGCGAACGATGGAACCCGAAAgCTCAgTCCATCCTCgTAAATCCTCAT CAATCATC (SEQ ID NO.: 129) | B2 |
| DLG4 B2 17 | TTGATAAGCTTGATCTCTATGAAAAgCTCAgTCCATCCTCgTAAATCCTCAT CAATCATC (SEQ ID NO.: 130) | B2 |
| DLG4 B2 19 | ATGTGCTGGTTCCCAACGCCCCAAAgCTCAgTCCATCCTCgTAAATCCTCAT CAATCATC (SEQ ID NO.: 131) | B2 |
| DLG4 B2 21 | TGGGCAGCGCCTCCTTCGATGAAAAgCTCAgTCCATCCTCgTAAATCCTCAT CAATCATC (SEQ ID NO.: 132) | B2 |
| DLG4 B2 23 | CCCACACTGTTGACCGCCAGGAAAAgCTCAgTCCATCCTCgTAAATCCTCAT CAATCATC (SEQ ID NO.: 133) | B2 |
| DLG4 B2 25 | TCATATGTGTTCTTCAGGGCTGAAAgCTCAgTCCATCCTCgTAAATCCTCAT CAATCATC (SEQ ID NO.: 134) | B2 |
| DLG4 B2 27 | TAGCTGTCACTCAGGTAGGCATAAAgCTCAgTCCATCCTCgTAAATCCTCAT CAATCATC (SEQ ID NO.: 135) | B2 |
| DLG4 B2 29 | CTGATCTCATTGTCCAGGTGCTAAAgCTCAgTCCATCCTCgTAAATCCTCAT CAATCATC (SEQ ID NO.: 136) | B2 |
| Camk2a iso2 1 | gAggAgggCAgCAAACgggAAgAgTCTTCCTTTACgAACGGGTGCAGGTGAT GGTAGCCA (SEQ ID NO.: 137) | B1 |
| Camk2a iso2 2 | CCTCgTAAATCCTCATCAATCATCCAgTAAACCgCCAATCCTCAAAGAGCTG GTACTCTT (SEQ ID NO.: 138) | B2 |
| Camk2a iso2 3 | gAggAgggCAgCAAACgggAAgAgTCTTCCTTTACgAAACAGAGAAGGCTCC CTTTCCCA (SEQ ID NO.: 139) | B1 |
| Camk2a iso2 4 | CCTCgTAAATCCTCATCAATCATCCAgTAAACCgCCAACCAGCCAGCACCTT CACACACC (SEQ ID NO.: 140) | B2 |
| Camk2a iso2 5 | gAggAgggCAgCAAACgggAAgAgTCTTCCTTTACgAAATAATCTTGGCAGC ATACTCCT (SEQ ID NO.: 141) | B1 |
| Camk2a iso2 6 | CCTCgTAAATCCTCATCAATCATCCAgTAAACCgCCAATGATCTCTGGCTGA AAGCTTCT (SEQ ID NO.: 142) | B2 |
| Camk2a iso2 7 | gAggAgggCAgCAAACgggAAgAgTCTTCCTTTACgAACGGGCCTCACGCTC CAGCTTCT (SEQ ID NO.: 143) | B1 |
| Camk2a iso2 8 | CCTCgTAAATCCTCATCAATCATCCAgTAAACCgCCAAATATTGGGGTGCTT CAACAAGC (SEQ ID NO.: 144) | B2 |
| Camk2a iso2 9 | gAggAgggCAgCAAACgggAAgAgTCTTCCTTTACgAAGAGATGCTGTCATG GAGTCGGA (SEQ ID NO.: 145) | B1 |
| Camk2a iso2 10 | CCTCgTAAATCCTCATCAATCATCCAgTAAACCgCCAATCGAAGATAAGGTA GTGGTGCC (SEQ ID NO.: 146) | B2 |
| Camk2a iso2 11 | gAggAgggCAgCAAACgggAAgAgTCTTCCTTTACgAAAACAGTTCCCCACC AGTAACCA (SEQ ID NO.: 147) | B1 |
| Camk2a iso2 12 | CCTCgTAAATCCTCATCAATCATCCAgTAAACCgCCAACTGTAATACTCCCG GGCCACAA (SEQ ID NO.: 148) | B2 |
| Camk2a iso2 13 | gAggAgggCAgCAAACgggAAgAgTCTTCCTTTACgAAATACAGTGGCTGGC ATCAGCTT (SEQ ID NO.: 149) | B1 |
| Camk2a iso2 14 | CCTCgTAAATCCTCATCAATCATCCAgTAAACCgCCAACAGTGTAGCACAGC CTCCAAGA (SEQ ID NO.: 150) | B2 |
| Camk2a iso2 15 | gAggAgggCAgCAAACgggAAgAgTCTTCCTTTACgAACGATGCACCACCCC CATCTGGT (SEQ ID NO.: 151) | B1 |
| Camk2a iso2 16 | CCTCgTAAATCCTCATCAATCATCCAgTAAACCgCCAAGCCAGCAACAGATT CTCAGGCT (SEQ ID NO.: 152) | B2 |
| Camk2a iso2 17 | gAggAgggCAgCAAACgggAAgAgTCTTCCTTTACgAAACAGCAGCGCCCTT GAGCTTCG (SEQ ID NO.: 153) | B1 |
| Camk2a iso2 18 | CCTCgTAAATCCTCATCAATCATCCAgTAAACCgCCAATCTATGGCCAGGCC AAAGTCTG (SEQ ID NO.: 154) | B2 |
| Camk2a iso2 19 | gAggAgggCAgCAAACgggAAgAgTCTTCCTTTACgAACATGCCTGCTGCTC CCCCTCCA (SEQ ID NO.: 155) | B1 |
| Camk2a iso2 20 | CCTCgTAAATCCTCATCAATCATCCAgTAAACCgCCAAAGGTATCCAGGTGT CCCTGCGA (SEQ ID NO.: 156) | B2 |
| Camk2a iso2 21 | gAggAgggCAgCAAACgggAAgAgTCTTCCTTTACgAATCCTTCCTCAGCAC TTCTGGGG (SEQ ID NO.: 157) | B1 |
| Camk2a iso2 22 | CCTCgTAAATCCTCATCAATCATCCAgTAAACCgCCAAGCCACAGGTCCAC GGGCTTCC (SEQ ID NO.: 158) | B2 |
| Camk2a iso2 23 | gAggAgggCAgCAAACgggAAgAgTCTTCCTTTACgAAAAGATATACAGGAT GACGCCAC (SEQ ID NO.: 159) | B1 |
| Camk2a iso2 24 | CCTCgTAAATCCTCATCAATCATCCAgTAAACCgCCAATCATCCCAGAACGG GGGATACC (SEQ ID NO.: 160) | B2 |
| Camk2a iso2 25 | gAggAgggCAgCAAACgggAAgAgTCTTCCTTTACgAATGCTGGTACAGGCG ATGCTGGT (SEQ ID NO.: 161) | B1 |
| Camk2a iso2 26 | CCTCgTAAATCCTCATCAATCATCCAgTAAACCgCCAAGATGGGAAATCATA GGCACCAG (SEQ ID NO.: 162) | B2 |
| Camk2a iso2 27 | gAggAgggCAgCAAACgggAAgAgTCTTCCTTTACgAAGGGTGACGGTGTC CCATTCTG (SEQ ID NO.: 163) | B1 |
| Camk2a iso2 28 | CCTCgTAAATCCTCATCAATCATCCAgTAAACCgCCAAAGCATCTTATTGAT CAGATCCT (SEQ ID NO.: 164) | B2 |
| Camk2a iso2 29 | gAggAgggCAgCAAACgggAAgAgTCTTCCTTTACgAAATGCGTTTGGACGG GTTGATGG (SEQ ID NO.: 165) | B1 |
| Camk2a iso2 30 | CCTCgTAAATCCTCATCAATCATCCAgTAAACCgCCAACATGGGTGCTTGAG AGCCTCAG (SEQ ID NO.: 166) | B2 |
| Camk2a iso2 31 | gAggAgggCAgCAAACgggAAgAgTCTTCCTTTACgAAGCCACGGTGGAGCG GTGCGAGA (SEQ ID NO.: 167) | B1 |

| | | |
|---|---|---|
| Camk2a iso2 32 | CCTCgTAAATCCTCATCAATCATCCAgTAAACCgCCAATCCACGGTCTCCTG TCTGTGCA (SEQ ID NO.: 168) | B2 |
| Camk2a iso2 33 | gAggAgggCAgCAAACgggAAgAgTCTTCCTTTACgAACTGGCATTGAACTT CTTCAGGC (SEQ ID NO.: 169) | B1 |
| Camk2a iso2 34 | CCTCgTAAATCCTCATCAATCATCCAgTAAACCgCCAAGTGGTGAGGATGGC TCCCTTCA (SEQ ID NO.: 170) | B2 |
| Camk2a iso2 35 | gAggAgggCAgCAAACgggAAgAgTCTTCCTTTACgAAGAGAAGTTCCTGGT GGCCAGCA (SEQ ID NO.: 171) | B1 |
| Camk2a iso2 36 | CCTCgTAAATCCTCATCAATCATCCAgTAAACCgCCAATTCTTCTTGTTTCC TCCGCTCT (SEQ ID NO.: 172) | B2 |
| Camk2a iso2 37 | gAggAgggCAgCAAACgggAAgAgTCTTCCTTTACgAATCAGAAGATTCCTT CACACCAT (SEQ ID NO.: 173) | B1 |
| Camk2a iso2 38 | CCTCgTAAATCCTCATCAATCATCCAgTAAACCgCCAATCTTCGTCCTCAAT GGTGGTGT (SEQ ID NO.: 174) | B2 |
| Camk2a iso2 39 | gAggAgggCAgCAAACgggAAgAgTCTTCCTTTACgAAATTTCCTGTTTGCG CACTTTGG (SEQ ID NO.: 175) | B1 |
| Camk2a iso2 40 | CCTCgTAAATCCTCATCAATCATCCAgTAAACCgCCAAGCTTCGATCAGCTG CTCTGTCA (SEQ ID NO.: 176) | B2 |
| Camk2a iso2 41 | gAggAgggCAgCAAACgggAAgAgTCTTCCTTTACgAAGACTCAAAGTCTCC ATTGCTTA (SEQ ID NO.: 177) | B1 |
| Camk2a iso2 42 | CCTCgTAAATCCTCATCAATCATCCAgTAAACCgCCAAGTCATTCCAGGGTC GCACATCT (SEQ ID NO.: 178) | B2 |
| Camk2a iso2 43 | gAggAgggCAgCAAACgggAAgAgTCTTCCTTTACgAACCCAGGGCCTCTGG TTCAAAGG (SEQ ID NO.: 179) | B1 |
| Camk2a iso2 44 | CCTCgTAAATCCTCATCAATCATCCAgTAAACCgCCAACGATGAAAGTCCAG GCCCTCCA (SEQ ID NO.: 180) | B2 |
| Camk2a iso2 45 | gAggAgggCAgCAAACgggAAgAgTCTTCCTTTACgAAGACCACAGGTTTTC AAAATAGA (SEQ ID NO.: 181) | B1 |
| Camk2a iso2 46 | CCTCgTAAATCCTCATCAATCATCCAgTAAACCgCCAAATGGTGGTGTGCAC GGGCTTGC (SEQ ID NO.: 182) | B2 |
| Camk2a iso2 47 | gAggAgggCAgCAAACgggAAgAgTCTTCCTTTACgAAATCAGGTGGATGTG AGGGTTCA (SEQ ID NO.: 183) | B1 |
| Camk2a iso2 48 | CCTCgTAAATCCTCATCAATCATCCAgTAAACCgCCAAATATAGGCGATGCA GGCTGACT (SEQ ID NO.: 184) | B2 |
| mCherry 2C 1 | cttcttcacctttgaaaccatAAgCATTCTTTCTTgAggAgggCAgCAAAC gggAAgAg (SEQ ID NO.: 185) | B1 |
| mCherry 2C 3 | ccatatgaactttaaatctcatAAgCATTCTTTCTTgAggAgggCAgCAAAC gggAAgAg (SEQ ID NO.: 186) | B1 |
| mCherry 2C 5 | cttcaccttcaccttcaatttcAAgCATTCTTTCTTgAggAgggCAgCAAAC gggAAgAg (SEQ ID NO.: 187) | B1 |
| mCherry 2C 7 | caccctttagtaactttcaatttaAAgCATTCTTTCTTgAggAgggCAgCAAAC gggAAgAg (SEQ ID NO.: 188) | B1 |
| mCherry 2C 9 | catacataaattgtggtgacaaAAgCATTCTTTCTTgAggAgggCAgCAAAC gggAAgAg (SEQ ID NO.: 189) | B1 |
| mCherry 2C 11 | ttaaataatctggaatatcagcAAgCATTCTTTCTTgAggAgggCAgCAAAC gggAAgAg (SEQ ID NO.: 190) | B1 |
| mCherry 2C 13 | tcaaaattcataactctttcccAAgCATTCTTTCTTgAggAgggCAgCAAAC gggAAgAg (SEQ ID NO.: 191) | B1 |
| mCherry 2C 15 | ctctcaatttaactttataaatAAgCATTCTTTCTTgAggAgggCAgCAAAC gggAAgAg (SEQ ID NO.: 192) | B1 |
| mCherry 2C 17 | ccatagttttttttgcataacAAgCATTCTTTCTTgAggAgggCAgCAAAC gggAAgAg (SEQ ID NO.: 193) | B1 |
| mCherry 2C 19 | tcaatctttgtttaatttcaccAAgCATTCTTTCTTgAggAgggCAgCAAAC gggAAgAg (SEQ ID NO.: 194) | B1 |
| mCherry 2C 21 | taatattaacattataagcaccAAgCATTCTTTCTTgAggAgggCAgCAAAC gggAAgAg (SEQ ID NO.: 195) | B1 |
| mCherry 2C 23 | tttcatattgttcaacaatagtAAgCATTCTTTCTTgAggAgggCAgCAAAC gggAAgAg (SEQ ID NO.: 196) | B1 |
| mCherry 2C 2 | attctttaataatagccatattAAAgCTCAgTCCATCCTCgTAAATCCTCAT CAATCATC (SEQ ID NO.: 197) | B2 |
| mCherry 2C 4 | attcatgaccattaactgaaccAAAgCTCAgTCCATCCTCgTAAATCCTCAT CAATCATC (SEQ ID NO.: 198) | B2 |
| mCherry 2C 6 | cagtttgagtaccttcatatggAAAgCTCAgTCCATCCTCgTAAATCCTCAT CAATCATC (SEQ ID NO.: 199) | B2 |
| mCherry 2C 8 | tatcccaagcaaatggtaatggAAAgCTCAgTCCATCCTCgTAAATCCTCAT CAATCATC (SEQ ID NO.: 200) | B2 |
| mCherry 2C 10 | gatgtttaacataagcttttgaAAAgCTCAgTCCATCCTCgTAAATCCTCAT CAATCATC (SEQ ID NO.: 201) | B2 |
| mCherry 2C 12 | ttaaaaccttctggaaatgacaAAAgCTCAgTCCATCCTCgTAAATCCTCAT CAATCATC (SEQ ID NO.: 202) | B2 |
| mCherry 2C 14 | gagtaacagtaacaacaccaccAAAgCTCAgTCCATCCTCgTAAATCCTCAT CAATCATC (SEQ ID NO.: 203) | B2 |
| mCherry 2C 16 | gaccatctgatggaaaattagtAAAgCTCAgTCCATCCTCgTAAATCCTCAT CAATCATC (SEQ ID NO.: 204) | B2 |
| mCherry 2C 18 | ttctttctgatgaagcttcccaAAAgCTCAgTCCATCCTCgTAAATCCTCAT CAATCATC (SEQ ID NO.: 205) | B2 |
| mCherry 2C 20 | gtaattgaactggtttttttagcAAAgCTCAgTCCATCCTCgTAAATCCTCAT CAATCATC (SEQ ID NO.: 206) | B2 |

-continued

| | | |
|---|---|---|
| mCherry 2C 22 | tcattatgtgaagtaatatccaAAAgCTCAgTCCATCCTCgTAAATCCTCAT CAATCATC (SEQ ID NO.: 207) | B2 |
| mCherry 2C 24 | atttatataattcatccataccAAAgCTCAgTCCATCCTCgTAAATCCTCAT CAATCATC (SEQ ID NO.: 208) | B2 |
| DLG4 ShHCR mis 1 | AATACCGCTACCAAGATGAAGAAAAgCTCAgTCCATCCTCgTAAATCCTCAT CAATCATC (SEQ ID NO.: 209) | B2 |
| DLG4 ShHCR mis 3 | TCCCCAACCAGGCCAATTCTCCAAAgCTCAgTCCATCCTCgTAAATCCTCAT CAATCATC (SEQ ID NO.: 210) | B2 |
| DLG4 ShHCR mis 5 | CCCCAGGATATGTGAACGGAACAAAgCTCAgTCCATCCTCgTAAATCCTCAT CAATCATC (SEQ ID NO.: 211) | B2 |
| DLG4 ShHCR mis 7 | TGGAAAGGGGTAACTCAGGTCTAAAgCTCAgTCCATCCTCgTAAATCCTCAT CAATCATC (SEQ ID NO.: 212) | B2 |
| DLG4 ShHCR mis 9 | CACACATCGGTGACGACCCATCAAAgCTCAgTCCATCCTCgTAAATCCTCAT CAATCATC (SEQ ID NO.: 213) | B2 |
| DLG4 ShHCR mis 11 | CTGCAGCCCAGGATGGCCGCCTAAAgCTCAgTCCATCCTCgTAAATCCTCAT CAATCATC (SEQ ID NO.: 214) | B2 |
| DLG4 ShHCR mis 13 | AAGTGGATGTCCGGGAGGTGACAAAgCTCAgTCCATCCTCgTAAATCCTCAT CAATCATC (SEQ ID NO.: 215) | B2 |
| DLG4 ShHCR mis 15 | CGGGTTCCATCGTTCGCCTCTAAAAgCTCAgTCCATCCTCgTAAATCCTCAT CAATCATC (SEQ ID NO.: 216) | B2 |
| DLG4 ShHCR mis 17 | TCATAGAGATCAAGCTTATCAAAAAgCTCAgTCCATCCTCgTAAATCCTCAT CAATCATC (SEQ ID NO.: 217) | B2 |
| DLG4 ShHCR mis 19 | GGGGCGTTGGGAACCAGCACATAAAgCTCAgTCCATCCTCgTAAATCCTCAT CAATCATC (SEQ ID NO.: 218) | B2 |
| DLG4 ShHCR mis 21 | TCATCGAAGGAGGCGCTGCCCAAAAgCTCAgTCCATCCTCgTAAATCCTCAT CAATCATC (SEQ ID NO.: 219) | B2 |
| DLG4 ShHCR mis 23 | TCCTGGCGGTCAACAGTGTGGGAAAgCTCAgTCCATCCTCgTAAATCCTCAT CAATCATC (SEQ ID NO.: 220) | B2 |
| DLG4 ShHCR mis 25 | CAGCCCTGAAGAACACATATGAAAAgCTCAgTCCATCCTCgTAAATCCTCAT CAATCATC (SEQ ID NO.: 221) | B2 |
| DLG4 ShHCR mis 27 | ATGCCTACCTGAGTGACAGCTAAAAgCTCAgTCCATCCTCgTAAATCCTCAT CAATCATC (SEQ ID NO.: 222) | B2 |
| DLG4 ShHCR mis 29 | AGCACCTGGACAATGAGATCAGAAAgCTCAgTCCATCCTCgTAAATCCTCAT CAATCATC (SEQ ID NO.: 223) | B2 |
| DLG4 ShHCR mis 2 | CGCCCCTCTGGAACACAGCCCAAgCATTCTTTCTTgAggAgggCAgCAAAC gggAAgAg (SEQ ID NO.: 224) | B1 |
| DLG4 ShHCR mis 4 | CTGTGATTGTCAACACGGACACAAgCATTCTTTCTTgAggAgggCAgCAAAC gggAAgAg (SEQ ID NO.: 225) | B1 |
| DLG4 ShHCR mis 6 | AGGGGAGATGGAGTATGAGGAAAgCATTCTTTCTTgAggAgggCAgCAAAC gggAAgAg (SEQ ID NO.: 226) | B1 |
| DLG4 ShHCR mis 8 | GCTTCAGCATCGCAGGTGGCACAAgCATTCTTTCTTgAggAgggCAgCAAAC gggAAgAg (SEQ ID NO.: 227) | B1 |
| DLG4 ShHCR mis 10 | TCTTTATCACCAAGATCATTCCAAgCATTCTTTCTTgAggAgggCAgCAAAC gggAAgAg (SEQ ID NO.: 228) | B1 |
| DLG4 ShHCR mis 12 | GGGTCAACGACAGCATCCTGTTAAgCATTCTTTCTTgAggAgggCAgCAAAC gggAAgAg (SEQ ID NO.: 229) | B1 |
| DLG4 ShHCR mis 14 | ATTCAGCTGCAGTGGAGGCCCTAAgCATTCTTTCTTgAggAgggCAgCAAAC gggAAgAg (SEQ ID NO.: 230) | B1 |
| DLG4 ShHCR mis 16 | TCATGCGCCGGAAACCCCCAGCAAgCATTCTTTCTTgAggAgggCAgCAAAC gggAAgAg (SEQ ID NO.: 231) | B1 |
| DLG4 ShHCR mis 18 | GGCCTAAAGGACTTGGCTTCAGAAgCATTCTTTCTTgAggAgggCAgCAAAC gggAAgAg (SEQ ID NO.: 232) | B1 |
| DLG4 ShHCR mis 20 | CTGGAGATAATAGCATCTACGTAAgCATTCTTTCTTgAggAgggCAgCAAAC gggAAgAg (SEQ ID NO.: 233) | B1 |
| DLG4 ShHCR mis 22 | AGGATGGCAGGTTGCAGATCGGAAgCATTCTTTCTTgAggAgggCAgCAAAC gggAAgAg (SEQ ID NO.: 234) | B1 |
| DLG4 ShHCR mis 24 | TAGAGGATGTCATGCATGAGGAAAgCATTCTTTCTTgAggAgggCAgCAAAC gggAAgAg (SEQ ID NO.: 235) | B1 |
| DLG4 ShHCR mis 26 | TTGTGTACCTAAAGGTGGCCAAAAgCATTCTTTCTTgAggAgggCAgCAAAC gggAAgAg (SEQ ID NO.: 236) | B1 |
| DLG4 ShHCR mis 28 | CTCCCCCAGACATCACAACCTCAAgCATTCTTTCTTgAggAgggCAgCAAAC gggAAgAg (SEQ ID NO.: 237) | B1 |
| DLG4 ShHCR mis 30 | ATAGCAGCTACTTGGGCACCGAAAgCATTCTTTCTTgAggAgggCAgCAAAC gggAAgAg (SEQ ID NO.: 238) | B1 | smFISH

| Probe Name | Oligonucleotide Sequence | Sequence Name |
|---|---|---|
| UBC | atggtcttaccagtcagagt (SEQ ID NO.: 239) | hUBC_1 |
| | gacattctcgatggtgtcac (SEQ ID NO.: 240) | hUBC_2 |
| | gggatgccttccttatcttg (SEQ ID NO.: 241) | hUBC_3 |
| | atcttccagctgttttccag (SEQ ID NO.: 242) | hUBC_4 |
| | cagtgagtgtcttcacgaag (SEQ ID NO.: 243) | hUBC_5 |
| | tcctggatctttgctttgac (SEQ ID NO.: 244) | hUBC_6 |
| | cagggtagactcttctctgga (SEQ ID NO.: 245) | hUBC_7 |
| | cttcacgaagatctgcatcc (SEQ ID NO.: 246) | hUBC_8 |
| | tcttggatctttgccttgac (SEQ ID NO.: 247) | hUBC_9 |

-continued

| | | | |
|---|---|---|---|
| | cagtgagtgtcttcacgaag | (SEQ ID NO.: 248) | hUBC_10 |
| | tgacgttctcgatagtgtca | (SEQ ID NO.: 249) | hUBC_11 |
| | tccttgtcttggatctttgc | (SEQ ID NO.: 250) | hUBC_12 |
| | cagggtagactctttctgga | (SEQ ID NO.: 251) | hUBC_13 |
| | cttcacgaagatctgcatcc | (SEQ ID NO.: 252) | hUBC_14 |
| | agagtgatggtcttaccagt | (SEQ ID NO.: 253) | hUBC_15 |
| | tcttggatctttgccttgac | (SEQ ID NO.: 254) | hUBC_16 |
| | cttcacgaagatctgcatcc | (SEQ ID NO.: 255) | hUBC_17 |
| | agagtgatggtcttaccagt | (SEQ ID NO.: 256) | hUBC_18 |
| | tcttggatctttgccttgac | (SEQ ID NO.: 257) | hUBC_19 |
| | tgtttcccagcaaagatcaa | (SEQ ID NO.: 258) | hUBC_20 |
| | cttcacgaagatctgcatcc | (SEQ ID NO.: 259) | hUBC_21 |
| | agagtgatggtcttaccagt | (SEQ ID NO.: 260) | hUBC_22 |
| | tcttggatctttgccttgac | (SEQ ID NO.: 261) | hUBC_23 |
| | tgtttcccagcaaagatcaa | (SEQ ID NO.: 262) | hUBC_24 |
| | cttcacgaagatctgcatcc | (SEQ ID NO.: 263) | hUBC_25 |
| | agagtgatggtcttaccagt | (SEQ ID NO.: 264) | hUBC_26 |
| | tcttggatctttgccttgac | (SEQ ID NO.: 265) | hUBC_27 |
| | tgtttcccagcaaagatcaa | (SEQ ID NO.: 266) | hUBC_28 |
| | gacattctcgatggtgtcac | (SEQ ID NO.: 267) | hUBC_29 |
| | gggatgccttccttatcttg | (SEQ ID NO.: 268) | hUBC_30 |
| | tgtttcccagcaaagatcaa | (SEQ ID NO.: 269) | hUBC_31 |
| | agagtggactctttctggat | (SEQ ID NO.: 270) | hUBC_32 |
| EEF2 | atctggtctaccgtgaagtt | (SEQ ID NO.: 271) | hEEF2_1 |
| | ttggccttcttgtccatgat | (SEQ ID NO.: 272) | hEEF2_2 |
| | gtatcagtgaagcgtgtctc | (SEQ ID NO.: 273) | hEEF2_3 |
| | ttgacttgatggtgatgcaa | (SEQ ID NO.: 274) | hEEF2_4 |
| | ctcgtagaagagggagatgg | (SEQ ID NO.: 275) | hEEF2_5 |
| | tccttgctctgcttgatgaa | (SEQ ID NO.: 276) | hEEF2_6 |
| | gggagtcaatgaggttgatg | (SEQ ID NO.: 277) | hEEF2_7 |
| | cggtccatcttgttcatcat | (SEQ ID NO.: 278) | hEEF2_8 |
| | gtggagatgatgacgttcac | (SEQ ID NO.: 279) | hEEF2_9 |
| | gtaccgaggacaggatcgat | (SEQ ID NO.: 280) | hEEF2_10 |
| | caaactgcttcagggtgaag | (SEQ ID NO.: 281) | hEEF2_11 |
| | aacttggccacatacatctc | (SEQ ID NO.: 282) | hEEF2_12 |
| | atgtcctctactttcttggc | (SEQ ID NO.: 283) | hEEF2_13 |
| | ttcatgatcgcatcaaacac | (SEQ ID NO.: 284) | hEEF2_14 |
| | gtccagtttgatgtccagtt | (SEQ ID NO.: 285) | hEEF2_15 |
| | gatggtgatcatctgcaaca | (SEQ ID NO.: 286) | hEEF2_16 |
| | tttggggtcacagcttttaa | (SEQ ID NO.: 287) | hEEF2_17 |
| | gtagaaccgacctttgtcgg | (SEQ ID NO.: 288) | hEEF2_18 |
| | ccatgatcctgaccttcagg | (SEQ ID NO.: 289) | hEEF2_19 |
| | ttcttcccaggggtatagtt | (SEQ ID NO.: 290) | hEEF2_20 |
| | tctggattggcttcaggtag | (SEQ ID NO.: 291) | hEEF2_21 |
| | ggcccatcatcaagattgtt | (SEQ ID NO.: 292) | hEEF2_22 |
| | gtcttcaccaggaactggtc | (SEQ ID NO.: 293) | hEEF2_23 |
| | ctgacgctgaacttcatcac | (SEQ ID NO.: 294) | hEEF2_24 |
| | atgatatgctctcccgactc | (SEQ ID NO.: 295) | hEEF2_25 |
| | gactcttcactgaccgtctc | (SEQ ID NO.: 296) | hEEF2_26 |
| | cttcatgtacagccggttgt | (SEQ ID NO.: 297) | hEEF2_27 |
| | tcgcctttatcgatgtcctc | (SEQ ID NO.: 298) | hEEF2_28 |
| | tgatgtcggtgaggatgttg | (SEQ ID NO.: 299) | hEEF2_29 |
| | cactgtccttgatctcgttg | (SEQ ID NO.: 300) | hEEF2_30 |
| | gtcagcacactggcatagag | (SEQ ID NO.: 301) | hEEF2_31 |
| | atctccacaaggtagatggg | (SEQ ID NO.: 302) | hEEF2_32 |
| USF2 | ggatccagacccgggtccag | (SEQ ID NO.: 303) | usf2_withUT R_1 |
| | tactggatgttgtggtcgcc | (SEQ ID NO.: 304) | usf2_withUT R_2 |
| | catttgtctctgtgcggaac | (SEQ ID NO.: 305) | usf2_withUT R_3 |
| | attttggatcacagcctgtc | (SEQ ID NO.: 306) | usf2_withUT R_4 |
| | gactgccaccattgctgaag | (SEQ ID NO.: 307) | usf2_withUT R_5 |
| | ctgggaaataggcaaatcgt | (SEQ ID NO.: 308) | usf2_withUT R_6 |
| | gacacagccgtagtatctcc | (SEQ ID NO.: 309) | usf2_withUT R_7 |
| | gtctgaagcacatcctgggg | (SEQ ID NO.: 310) | usf2_withUT R_8 |
| | ggcgatcgtcctctgtgttc | (SEQ ID NO.: 311) | usf2_withUT R_9 |
| | tggttccatcaattttggga | (SEQ ID NO.: 312) | usf2_withUT R_10 |
| | ttctcctctcatctcggggt | (SEQ ID NO.: 313) | usf2_withUT R_11 |
| | ctccacttcgttgtgctggg | (SEQ ID NO.: 314) | usf2_withUT R_12 |
| | cagttgttgatcttgtccct | (SEQ ID NO.: 315) | usf2_withUT R_13 |
| | gattttcgaaagctggacga | (SEQ ID NO.: 316) | usf2_withUT R_14 |
| | gttgtctgcgttacagtctg | (SEQ ID NO.: 317) | usf2_withUT R_15 |
| | ggccttggacaggatccctc | (SEQ ID NO.: 318) | usf2_withUT R_16 |
| | cgcaactcccgggatgtaatc | (SEQ ID NO.: 319) | usf2_withUT R_17 |
| | ctgcatgcgctggttggtct | (SEQ ID NO.: 320) | usf2_withUT R_18 |
| | gctcggcctctttgaaggtc | (SEQ ID NO.: 321) | usf2_withUT R_19 |
| | agctcgttgtccatctgcag | (SEQ ID NO.: 322) | usf2_withUT R_20 |
| | caccatctccaggttgtgct | (SEQ ID NO.: 323) | usf2_withUT R_21 |
| | tgtatccacagaaatgcatt | (SEQ ID NO.: 324) | usf2_withUT R_22 |

| | | |
|---|---|---|
| | ggaggataccgtttccaagt (SEQ ID NO.: 325) | usf2_withUT_R_23 |
| | gtgagaccactagaagtgcc (SEQ ID NO.: 326) | usf2_withUT_R_24 |
| | cataggtccaggccccgggt (SEQ ID NO.: 327) | usf2_withUT_R_25 |
| | cagggacccagaaacaagag (SEQ ID NO.: 328) | usf2_withUT_R_26 |
| | gggccagtttattgcagtta (SEQ ID NO.: 329) | usf2_withUT_R_27 |
| TOP2A | ctgggcggagcaaaatatgt (SEQ ID NO.: 330) | hTOP2A_CD_S_1 |
| | tcttcatcgtaaacccacat (SEQ ID NO.: 331) | hTOP2A_CD_S_2 |
| | ccggatcaattgtgactcta (SEQ ID NO.: 332) | hTOP2A_CD_S_3 |
| | cctttccattattccatat (SEQ ID NO.: 333) | hTOP2A_CD_S_4 |
| | agaagttaggagctgtccaa (SEQ ID NO.: 334) | hTOP2A_CD_S_5 |
| | ccagcaatatcatatgctct (SEQ ID NO.: 335) | hTOP2A_CD_S_6 |
| | ttactggcagtttatttcca (SEQ ID NO.: 336) | hTOP2A_CD_S_7 |
| | tgttgatccaaagctcttgg (SEQ ID NO.: 337) | hTOP2A_CD_S_8 |
| | aactggacttgggccttaaa (SEQ ID NO.: 338) | hTOP2A_CD_S_9 |
| | atcattggcatcatcgagtt (SEQ ID NO.: 339) | hTOP2A_CD_S_10 |
| | gtcaggataagcgtacactc (SEQ ID NO.: 340) | hTOP2A_CD_S_11 |
| | ggaaaaccccatatttgtct (SEQ ID NO.: 341) | hTOP2A_CD_S_12 |
| | tttcttgtactgaagaccca (SEQ ID NO.: 342) | hTOP2A_CD_S_13 |
| | ttggtcctgatctgtcataa (SEQ ID NO.: 343) | hTOP2A_CD_S_14 |
| | ctccagaaaacgatgtcgca (SEQ ID NO.: 344) | hTOP2A_CD_S_15 |
| | gttaaccattcctttcgatc (SEQ ID NO.: 345) | hTOP2A_CD_S_16 |
| | agctaattgggcaaccttta (SEQ ID NO.: 346) | hTOP2A_CD_S_17 |
| | atgtatcgtggactagcaga (SEQ ID NO.: 347) | hTOP2A_CD_S_18 |
| | acgctggttgtcatcatata (SEQ ID NO.: 348) | hTOP2A_CD_S_19 |
| | ttcttctccatccatcaaac (SEQ ID NO.: 349) | hTOP2A_CD_S_20 |
| | cccttgaagttcttgtaact (SEQ ID NO.: 350) | hTOP2A_CD_S_21 |
| | tatgagaggaggtgtcttct (SEQ ID NO.: 351) | hTOP2A_CD_S_22 |
| | tgtatggtattccctatagt (SEQ ID NO.: 352) | hTOP2A_CD_S_23 |
| | tcagtttagcagattcagca (SEQ ID NO.: 353) | hTOP2A_CD_S_24 |
| | cttcacaggatccgaatcat (SEQ ID NO.: 354) | hTOP2A_CD_S_25 |
| | gtggaatgactctttgacca (SEQ ID NO.: 355) | hTOP2A_CD_S_26 |
| | tgctcctatctgattctgaa (SEQ ID NO.: 356) | hTOP2A_CD_S_27 |
| | agtggaggtggaagactgac (SEQ ID NO.: 357) | hTOP2A_CD_S_28 |
| | aattcaaagctggatcccctt (SEQ ID NO.: 358) | hTOP2A_CD_S_29 |
| | caggatcaggcttttgagag (SEQ ID NO.: 359) | hTOP2A_CD_S_30 |
| | cttggatttcttgcttgtga (SEQ ID NO.: 360) | hTOP2A_CD_S_31 |
| | tatggaagtcatcactctcc (SEQ ID NO.: 361) | hTOP2A_CD_S_32 |
| NEAT1 | gacctagtctccttgccaag (SEQ ID NO.: 362) | NEAT1_1 |
| | ggatatttccatgcagcct (SEQ ID NO.: 363) | NEAT1_2 |
| | acaagttgaagattagccct (SEQ ID NO.: 364) | NEAT1_3 |
| | ccttggtctggaaaaaaagg (SEQ ID NO.: 365) | NEAT1_4 |
| | cgagctaagttcagttccac (SEQ ID NO.: 366) | NEAT1_5 |
| | ggccgagcgaaaattacata (SEQ ID NO.: 367) | NEAT1_6 |
| | cctgtcaaacatgctaggtg (SEQ ID NO.: 368) | NEAT1_7 |
| | actgccacctggaaaataaa (SEQ ID NO.: 369) | NEAT1_8 |
| | gtgagctcacaagaagagtt (SEQ ID NO.: 370) | NEAT1_9 |
| | accagatgaccaggtaatgt (SEQ ID NO.: 371) | NEAT1_10 |
| | cggtccatgaagcatttttg (SEQ ID NO.: 372) | NEAT1_11 |
| | tcgccatgaggaacactata (SEQ ID NO.: 373) | NEAT1_12 |
| | aatctgcaggcatcaattga (SEQ ID NO.: 374) | NEAT1_13 |
| | cctggaaacagaacattgga (SEQ ID NO.: 375) | NEAT1_14 |
| | gcatctgctgtggactttttt (SEQ ID NO.: 376) | NEAT1_15 |
| | ggctctggaacaagcattta (SEQ ID NO.: 377) | NEAT1_16 |
| | tgcagcatctgaaaacctttt (SEQ ID NO.: 378) | NEAT1_17 |
| | accggaggctcaatttagaa (SEQ ID NO.: 379) | NEAT1_18 |
| | caaggttccaagcacaaaac (SEQ ID NO.: 380) | NEAT1_19 |
| | acagcttagggatcttcttg (SEQ ID NO.: 381) | NEAT1_20 |
| | tggcatcaacgttaaaatgt (SEQ ID NO.: 382) | NEAT1_21 |
| | tctacaaggcatcaatctgc (SEQ ID NO.: 383) | NEAT1_22 |
| | aagaacttctccgagaaacg (SEQ ID NO.: 384) | NEAT1_23 |
| | gccccaagttatttcatcag (SEQ ID NO.: 385) | NEAT1_24 |
| | gcgtttagcacaacacaatg (SEQ ID NO.: 386) | NEAT1_25 |
| | ggaatgaccaacttgtaccc (SEQ ID NO.: 387) | NEAT1_26 |
| | caatgcccaaactagacctg (SEQ ID NO.: 388) | NEAT1_27 |
| | tcctagtaatctgcaatgca (SEQ ID NO.: 389) | NEAT1_28 |
| | agcaagaacaaaagagcact (SEQ ID NO.: 390) | NEAT1_29 |
| | ggtcctcttactagaatgcc (SEQ ID NO.: 391) | NEAT1_30 |
| | ctgtgtcacctgttttcagt (SEQ ID NO.: 392) | NEAT1_31 |
| | cctttggttctcggaaaact (SEQ ID NO.: 393) | NEAT1_32 |
| | agctggtaaagacatttccc (SEQ ID NO.: 394) | NEAT1_33 |
| | ctctgaaacaggctgtcttg (SEQ ID NO.: 395) | NEAT1_34 |
| | gcccatctttcaagtgacta (SEQ ID NO.: 396) | NEAT1_35 |
| | aaccacctaagttgctaagg (SEQ ID NO.: 397) | NEAT1_36 |
| | tcgtcttaagtggtccctta (SEQ ID NO.: 398) | NEAT1_37 |
| | atccagaagagccatctaa (SEQ ID NO.: 399) | NEAT1_38 |
| | acctgtgacaaatgaggaac (SEQ ID NO.: 400) | NEAT1_39 |
| | agatgtgtttctaaggcacg (SEQ ID NO.: 401) | NEAT1_40 |

```
acagtgaccacaaaaggtta  (SEQ ID NO.: 402)        NEAT1_41
agcaaaggtacatggattct  (SEQ ID NO.: 403)        NEAT1_42
cagggttttcagatcacaca  (SEQ ID NO.: 404)        NEAT1_43
ccccaagtcattggttaaga  (SEQ ID NO.: 405)        NEAT1_44
tcccaacgacagtaattgtt  (SEQ ID NO.: 406)        NEAT1_45
cccatacatgcgtgactaat  (SEQ ID NO.: 407)        NEAT1_46
caacagcatacccgagacta  (SEQ ID NO.: 408)        NEAT1_47
acagagcaacataccagtac  (SEQ ID NO.: 409)        NEAT1_48
```

Cell Culture and Fixation:

HeLa (ATCC CCL-2) cells and HEK293-FT cells (Invitrogen) were cultured on Nunc Lab-Tek II Chambered Coverglass (Thermo Scientific) in D10 medium (Cellgro) supplemented with 10% FBS (Invitrogen), 1% penicillin/streptomycin (Cellgro), and 1% sodium pyruvate (BioWhittaker). Cells were authenticated by the manufacturer and tested for mycoplasma contamination to their standard levels of stringency, and were here used because they are common cell lines for testing new tools. Cultured cells were washed once with DPBS (Cellgro), fixed with 10% formalin for 10 mins, and washed twice with 1×PBS. Fixed cells were then stored in 70% Ethanol at 4° C. until use.

Preparation of LabelX:

Acryloyl-X, SE (6-((acryloyl)amino)hexanoic acid, succinimidyl ester, here abbreviated AcX; Thermo-Fisher) was resuspended in anhydrous DMSO at a concentration of 10 mg/mL, aliquoted and stored frozen in a desiccated environment. LABEL-IT® Amine Modifying Reagent (Mirus Bio, LLC) was resuspended in the provided Mirus Reconstitution Solution at 1 mg/ml and stored frozen in a desiccated environment. To prepare LabelX, 10 μL of AcX (10 mg/mL) was reacted with 100 μL of LABEL-IT® Amine Modifying Reagent (1 mg/mL) overnight at room temperature with shaking. LabelX was subsequently stored frozen (−20° C.) in a desiccated environment until use.

Mouse Perfusion:

All methods for animal care and use were approved by the Massachusetts Institute of Technology Committee on Animal Care and were in accordance with the National Institutes of Health Guide for the Care and Use of Laboratory Animals. All solutions below were made up in 1× phosphate buffered saline (PBS) prepared from nuclease free reagents. Mice were anesthetized with isoflurane and perfused transcardially with ice cold 4% paraformaldehyde. Brains were dissected out, left in 4% paraformaldehyde at 4° C. for one day, before moving to PBS containing 100 mM glycine. Slices (50 μm and 200 μm) were sliced on a vibratome (Leica VT1000S) and stored at 4° C. in PBS until use. The mouse used in FIG. 3 and related analyses was a Thy1-YFP (Tg(Thy1-YFP)16 Jrs) male mouse in the age range 6-8 weeks. No sample size estimate was performed, since the goal was to demonstrate a technology. No exclusion, randomization or blinding of samples was performed.

Figure 15:
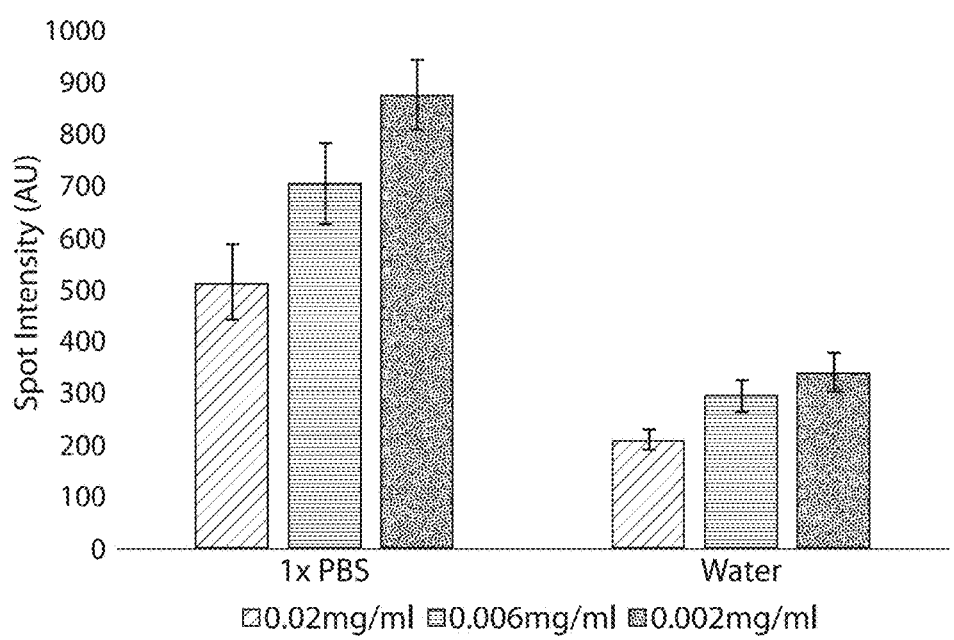
FIG. 15: Dependence of RNA FISH spot intensity on degree of expansion and concentration of LabelX. HeLa cells, treated with LabelX diluted to different final concentrations of Label-It Amine concentration, were expanded and stained with a probe-set against GAPDH. After staining, the gelled samples were expanded in 1×PBS (~2× expansion ratio) and water (~4× expansion ratio) and the spot intensity for the different samples was quantified. Plotted are mean±standard error; N=6 cells.

LabelX Treatment of Cultured Cells and Brain Slices:

Fixed cells were washed twice with 1×PBS, once with 20 mM MOPS pH 7.7, and incubated with LabelX diluted to a desired final concentration in MOPS buffer (20 mM MOPS pH 7.7) at 37° C. overnight followed by two washes with 1×PBS. For cells, ranges of LabelX were used that resulted in a LABEL-IT® Amine concentration of 0.006-0.02 mg/mL; higher concentrations resulted in somewhat dimmer smFISH staining (FIG. 15), but otherwise no difference in staining quality was observed with LABEL-IT® Amine concentrations in this range. For FIG. 1e, FIG. 4, FIG. 5, and FIG. 6 fixed cells were incubated with LabelX diluted to a final LABEL-IT® Amine concentration of 0.02 mg/mL. For all other experiments in cells, fixed cells were treated with LabelX diluted to a final LABEL-IT® Amine concentration of 0.006 mg/mL.

Brain slices, as prepared above, were incubated with 20 mM MOPS pH 7.7 for 30 mins and subsequently incubated with LabelX diluted to a final LABEL-IT® Amine concentration of 0.1 mg/mL (due to their increased thickness and increased fragmentation from formaldehyde post-fixation) in MOPS buffer (20 mM MOPS pH 7.7) at 37° C. overnight. For YFP retention, slices were treated with 0.05 mg/mL AcX in PBS for >6 hours @ RT.

smFISH in Fixed Cultured Cells Before Expansion:

Fixed cells were briefly washed once with wash buffer (10% formamide, 2×SSC) and hybridized with RNA FISH probes in hybridization buffer (10% formamide, 10% dextran sulfate, 2×SSC) overnight at 37° C. Following hybridization, samples were washed twice with wash buffer, 30 mins per wash, and washed once with 1×PBS. Imaging was performed in 1× PBS.

smFISH probe sets targeting the human transcripts for TFRC, ACTB, GAPDH, XIST, and 5' portion of NEAT1 were ordered from Stellaris with Quasar 570 dye. Probe sets against UBC, EEF2, USF2, TOP2A and full length NEAT1 were synthesized, conjugated to fluorophores, and subsequently purified by HPLC as described previously[37]. Oligonucleotide sequences for probe sets and accession numbers can be found in Table 4.

Gelation, Digestion and Expansion:

Monomer solution (1×PBS, 2 M NaCl, 8.625% (w/w) sodium acrylate, 2.5% (w/w) acrylamide, 0.15% (w/w) N,N'-methylenebisacrylamide) was mixed, frozen in aliquots, and thawed before use. Monomer solution was cooled to 4° C. before use. For gelling cultured cells treated with LabelX, a concentrated stock of VA-044 (25% w/w, chosen instead of the Ammonium persulfate (APS)/Tetramethylethylenediamine (TEMED) of the original ExM protocol[1] because APS/TEMED resulted in autofluorescence that was small in magnitude but appreciable in the context of smFISH) was added to the monomer solution to a final concentration of 0.5% (w/w) and degassed in 200 μl aliquots for 15 mins. Cells were briefly incubated with the monomer solution plus VA-044 and transferred to a humidified chamber. Subsequently, the humidified chamber was purged with nitrogen gas. To initiate gelation, the humidified chamber was transferred to a 60° C. incubator for two hours. For gelling brain slices treated with LabelX, gelation was performed as in the original ExM protocol (since, with HCR amplification, the slight autofluorescence of APS/TEMED was negligible). Gelled cultured cells and brain slices were digested with Proteinase K (New England Biolabs) diluted 1:100 to 8 units/mL in digestion buffer (50 mM Tris (pH 8), 1 mM EDTA, 0.5% Triton X-100, 500 mM NaCl) and digestion was carried out overnight at 37° C. The gels expand slightly in the high osmolarity digestion buffer (~1.5×). After digestion, gels were stored in 1×PBS until use and expansion was carried out as previously described.

smFISH Staining after Expansion:

Expanded gels were incubated with wash buffer (10% formamide, 2×SSC) for 30 mins at room temperature and hybridized with RNA FISH probes in hybridization buffer (10% formamide, 10% dextran sulfate, 2×SSC) overnight at 37° C. Following hybridization, samples were washed twice with wash buffer, 30 minutes per wash, and washed once with 1×PBS for another 30 mins. Imaging was performed in 1×PBS.

Image Processing and Analysis of smFISH Performed on Cultured Cells:

Widefield images of smFISH staining performed before or after expansion were first processed using a rolling-ball background subtraction algorithm (FIJI)[38] with a 200 pixel radius. Subsequently, maximum intensity Z-projections of these images were generated. Spots were then localized and counted using a code developed by the Raj lab and available online (http://rajlab.seas.upenn.edu/StarSearch/launch.html). This image analysis was performed for FIGS. 1C-E, FIGS. 2A-C, FIG. FIGS. 5A-E, FIGS. 6A-G, FIGS. 7A-E, FIGS. 9A-B, 11A-C.

Analysis of Expansion Isotropy:

smFISH images before and after expansion of TOP2A was rigidly aligned via two control points using the FIJI plugin Turboreg[39]. Spots were localized and counted via a custom spot counting Matlab code developed by the Raj lab (complete source code and instructions can be found at https://bitbucket.org/arjunrajlaboratory/rajlabimagetools/wiki/Home). Length measurements were performed among all pairs of points before expansion and the corresponding pairs of points after expansion via a custom Matlab script. Measurement error was defined as the absolute difference between the before and after expansion length measurements (FIG. 8C).

Re-Embedding of Expanded Gels in Acrylamide Matrix:

For serial staining in cells, expanded gels were re-embedded in acrylamide to stabilize the gels in the expanded state. Briefly: gels were expanded in water and cut manually to ~1 mm thickness with a stainless steel blade. Cut gels were incubated in 3% acrylamide, 0.15% N,N'-Methylenebisacrylamide with 0.05% APS, 0.05% TEMED and 5 mM Tris ph 10.5 for 20 minutes on a shaker. There is a ~30% reduction in gel size during this step. Excess solution is removed from the gels and the gels are dried with light wicking from a laboratory wipe. Gels are placed on top of a bind-silane treated (see below) coverslip or glass bottom plate with a coverslip placed on top of the gels before moving into a container and purged with nitrogen. The container is moved to a 37° C. incubator for gelation for 1.5 hours.

Staining of Re-Embedded Gels:

Re-embedded staining of gels were performed with exact conditions as described above for expanded gels, except post-hybridization washes were changed to twice with wash buffer (10% formamide), 60 minutes per wash.

Probes were removed for multiple rounds of hybridization via treatment with DNAse I or 100% formamide. For DNAse I, samples were treated with DNAse I at 0.5 U/μL for 6 hours at RT. For formamide stripping, samples were treated with 100% formamide at 6 hours at 37 C.

Bind-Silane Treatment of Coverslips:

Coverslips and glass bottom 24 well plates were treated with Bind-Silane, a silanization reagent which incorporates acryloyl groups onto the surface of glass to perform in free radical polymerization. Briefly, 5 μL of Bind-Silane reagent was diluted into 8 mL of ethanol, 1.8 mL of ddH$_2$O and 200 μL of acetic acid. Coverslips and glass bottom 24 well plates were washed with ddH$_2$O followed by 100% ethanol, followed by the diluted Bind-Silane reagent. After a brief wash with the diluted Bind-Silane reagent, the cover-slip was dried, then washed with 100% ethanol, and then dried again. Coverslips were prepared immediately before use.

Probe Design for HCR-FISH:

Probe sequences and accession numbers for mRNA targets can be found in Table 4. Probes were designed for HCR-FISH by tiling the CDS of mRNA targets with 22-mer oligos spaced by 3-7 bases. HCR initiators were appended to tiled sequences via a 2 base spacer (AA). For 2 color probe-sets, even and odd tiled probes were assigned different HCR-initiators to allow for amplification in different color channel.

RNA FISH with Hybridization Chain Reaction (HCR) Amplification:

Gelled samples were incubated with wash buffer (20% formamide, 2×SSC) for 30 mins at room temperature and hybridized with HCR initiator tagged FISH probes in hybridization buffer (20% formamide, 10% dextran sulfate, 2×SSC) overnight at 37° C. Following hybridization, samples were washed twice with wash buffer, 30 mins per wash, and incubated with 1×PBS for 2 hrs at 37° C. Subsequently, samples were incubated with 1×PBS for at least 6 hrs at room temperature. Before HCR amplification, hybridized samples were pre-incubated with amplification buffer (10% dextran sulfate, 5×SSC, 0.1% Tween 20) for 30 mins. To initiate amplification, HCR hairpin stocks (Alexa 456 and Alexa 647 fluorophores) at 3 μM were snap-cooled by heating to 95° C. for 90 seconds, and leaving to cool at room temperature for 30 mins. Gelled samples were then incubated with HCR hairpins diluted to 60 nM in amplification buffer for 3 hrs at room temperature. After amplification, gels were washed with 5×SSCT (5×SSC, 0.1% Tween 20) twice with one hour per wash.

Imaging of Cultured Cells Using ExFISH:

Both cultured cells as well as LabelX treated and expanded cultured cells were imaged on a Nikon Ti-E epifluorescence microscope with a SPECTRA X light engine (Lumencor), and a 5.5 Zyla sCMOS camera (Andor), controlled by NIS-Elements AR software. For FIGS. 1C, 1D, and FIGS. 6A-G, FIGS. 7A-E, and FIGS. 8-D a 40×1.15 NA water immersion objective was used. For all other experiments with cultured cells, a 60×1.4 NA oil immersion objective was used.

For imaging smFISH probes labeled with fluorophores, the following filter cubes (Semrock, Rochester, N.Y.) were used: Alexa 488, GFP-1828A-NTE-ZERO; Quasar 570, LF561-B-000; Alexa 594, FITC/TXRED-2X-B-NTE; Atto 647N, Cy5-4040C-000.

Imaging of Expanded Brain Slices:

For epifluorescence imaging of brain sections before and after expansion (FIGS. 3A-E) and to quantify expansion factors of tissue slices specimens were imaged on a Nikon Ti-E epifluorescence microscope with a 4×0.2 NA air objective, a SPECTRA X light engine (Lumencor), and a 5.5 Zyla sCMOS camera (Andor), controlled by NIS-Elements AR software.

Post-expansion confocal imaging of expanded brain tissue was performed on an Andor spinning disk (CSU-X1 Yokogawa) confocal system with a 40×1.15 NA water objective (FIGS. 3F-K, FIGS. 13A-G) on a Nikon TI-E microscope body. GFP was excited with a 488 nm laser, with 525/40 emission filter. Alexa 546 HCR amplicons were excited with a 561 nm laser with 607/36 emission filter. Alexa 647 amplicons were excited with a 640 nm laser with 685/40 emission filter.

Gels were expanded in with 3 washes, 15 minutes each of 0.05×SSC. The expansion factor can be controlled with the salt concentration. It was found that 0.05×SSC gives 3× expansion, while still giving enough salt for hybridization stability. To stabilize the gels against drift during imaging following expansion, gels were placed in glass bottom 6 well plates with all excess liquid removed. If needed, liquid low melt agarose (2% w/w) was pipetted around the gel and allowed to solidify, to encase the gels before imaging.

Lightsheet imaging was performed on a Zeiss Z.1 lightsheet microscope. Briefly, the sample was fixed on a custommade plastic holder using super glue and mounted on the freely rotating stage of the Z.1 lightsheet. Lightsheets were generated by two illumination objectives (5×, NA 0.1), and the fluorescence signal detected by a 20× water immersion objective (NA 1.0). Both lightsheets were used for data collection. The image volume dimensions of a single tile were 1400×1400×1057 pixels, with a voxel size of 227 nm laterally and 469 nm axially. The laserlines used for excitation were 488 nm, 561 nm and 638 nm. The individual laser transmissions were set to 5%, with the maximum output of 50 mW (488 nm and 561 nm) and 75 mW (638 nm). Optical filters used to separate and clean the fluorescence response included a Chroma T5601pxr as a dichroic, and a Chroma 59001m for GFP and 59007m for Alexa 546 and Alexa 647. Two PCO.Edge 5.5 m sCMOS cameras were used to capture two fluorescence channels simultaneously. Tiled datasets were taken with the Zeiss ZEN Software, and subsequently merged and processed with FIJI, Arivis Vision4D and Bitplane Imaris.

Two Color Analysis in Slices:

A sliding window averaging (or minimization) scheme in Z (3 optical sections) was used to suppress movement artifacts before spot detection processing. RNA puncta were detected via a custom 3D spot counting Matlab code developed by the Raj lab; complete source code and instructions can be found at https://bitbucket.org/arjunrajlaboratory/rajlabimagetools/wiki/Home.

Spot centroids were extracted from both color channels, and spots were determined to be co-localized if their centroids were within a 3 pixel radius in the x,y dimensions and a 2 pixel radius in the z dimension.

HCR Reversal Via Toe-Hold Mediated Strand Displacement:

HCR amplification commences upon the addition of two HCR metastable amplifier hairpins. We designed a pair of HCR amplifiers, B2H1T and B2H2 (see below for sequence), where B2H1T bears a 6 bp toe-hold for strand displacement. To initiate HCR amplification, aliquots of these amplifiers at 3 µM were snap-cooled by heating to 95° C. for 90 seconds, and leaving to cool at room temperature for 30 mins. Gelled samples were then incubated with HCR hairpins diluted to 60 nM in amplification buffer for 3 hrs at room temperature. After amplification, gels were washed with 5×SSCT (5×SSC, 0.1% Tween 20) twice with one hour per wash. Subsequently, HCR reversal was initiated by the addition of a displacement strand (see below for sequence) at 200 nM in 5×SSCT.

B2H1T:
ggCggTTTACTggATgATTgATgAggATTTACgAggAgCTCAgTCCATCC

TCgTAAATCCTCATCAATCATCAAATAG (SEQ ID NO.: 410).

B2H2:
/5'-Alexa546-C12/
CCTCgTAAATCCTCATCAATCATCCAgTAAACCgCCgATgATTgATgAgg

ATTTACgAggATggACTgAgCT (SEQ ID NO.: 411).

Displacement Strand:
CTATTTGATGATTGATGAGGATTTAcGAGGA-
TGGAcTGAGcT (SEQ ID NO.: 412).

REFERENCES

1. Chen, F., Tillberg, P. W. & Boyden, E. S. Expansion microscopy. *Science* (80-.). 347, 543-548 (2015).
2. Femino, A. M., Fay, F., Fogarty, K. & Singer, R. Visualization of Single RNA Transcripts in Situ. *Science* (80,). 280, 585-590 (1998).
3. Levsky, J. M. & Singer, R. H. Fluorescence in situ hybridization: past, present and future. *J. Cell Sci.* 116, 2833-2838 (2003).
4. Raj, A., van den Bogaard, P., Rifkin, S. A., van Oudenaarden, A. & Tyagi, S. Imaging individual mRNA molecules using multiple singly labeled probes. *Nat. Methods* 5, 877-9 (2008).
5. Choi, H. M. T. et al. Programmable in situ amplification for multiplexed imaging of mRNA expression. *Nat. Biotechnol.* 28, 1208-12 (2010).
6. Choi, H. M. T., Beck, V. A. & Pierce, N. A. Next-Generation in Situ Hybridization Chain Reaction: Higher Gain, Lower Cost, Greater Durability. *ACS Nano* 8, 4284-4294 (2014).
7 Cajigas, I. J. et al. The local transcriptome in the synaptic neuropil revealed by deep sequencing and high-resolution imaging. *Neuron* 74, 453-66 (2012).
8. Wang, F. et al. RNAscope: A novel in situ RNA analysis platform for formalin-fixed, paraffin-embedded tissues. *J. Mol. Diagnostics* 14, 22-29 (2012).
9. Tillberg, P. W. et al. Expansion Microscopy of Biological Specimens with Protein Retention. *Nat. Biotechnol.*
10. Chozinski, T. J. et al. Expansion microscopy with conventional antibodies and fluorescent proteins. *Nat. Methods* (2016). doi:10.1038/nmeth.3833
11. Engreitz, J. M. et al. The Xist lncRNA exploits three-dimensional genome architecture to spread across the X chromosome. *Science* 341, 1237973 (2013).
12. Panning, B., Dausman, J. & Jaenisch, R. X chromosome inactivation is mediated by Xist RNA stabilization. *Cell* 90, 907-16 (1997).
13. Plath, K., Mlynarczyk-Evans, S., Nusinow, D. A. & Panning, B. Xist RNA and the mechanism of X chromosome inactivation. *Annu. Rev. Genet.* 36, 233-78 (2002).
14. Mito, M., Kawaguchi, T., Hirose, T. & Nakagawa, S. Simultaneous multicolor detection of RNA and proteins using super-resolution microscopy. *Methods* (2015). doi:10.1016/j.ymeth.2015.11.007
15. Clemson, C. M. et al. An architectural role for a nuclear noncoding RNA: NEAT1 RNA is essential for the structure of paraspeckles. *Mol. Cell* 33, 717-26 (2009).
16. Lieberman-Aiden, E. et al. Comprehensive mapping of long-range interactions reveals folding principles of the human genome. *Science* 326, 289-93 (2009).
17. Lubeck, E. & Cai, L. Single-cell systems biology by super-resolution imaging and combinatorial labeling. *Nat. Methods* 9, 743-8 (2012).

18. Lubeck, E., Coskun, A. F., Zhiyentayev, T., Ahmad, M. & Cai, L. Single-cell in situ RNA profiling by sequential hybridization. *Nat. Methods* 11, 360-1 (2014).
19. Chen, K. H., Boettiger, A. N., Moffitt, J. R., Wang, S. & Zhuang, X. Spatially resolved, highly multiplexed RNA profiling in single cells. *Science (80-.)*. 348, aaa6090-aaa6090 (2015).
20. Beliveau, B. J. et al. Versatile design and synthesis platform for visualizing genomes with Oligopaint FISH probes. *Proc. Natl. Acad. Sci. U.S.A.* 109, 21301-6 (2012).
21. Feng, G. et al. Imaging neuronal subsets in transgenic mice expressing multiple spectral variants of GFP. *Neuron* 28, 41-51 (2000).
22. Lein, E. S. et al. Genome-wide atlas of gene expression in the adult mouse brain. *Nature* 445, 168-76 (2007).
23. Huisken, J., Swoger, J., Bene, F. Del, Wittbrodt, J. & Stelzer, E. H. K. Optical Sectioning Deep Inside Live Embryos by Selective Plane Illumination Microscopy. *Science* 305, 1007-1009 (2004).
24. Batish, M., van den Bogaard, P., Kramer, F. R. & Tyagi, S. Neuronal mRNAs travel singly into dendrites. *Proc. Natl. Acad. Sci.* 109, 4645-4650 (2012).
25. Cabili, M. N. et al. Localization and abundance analysis of human lncRNAs at single-cell and single-molecule resolution. *Genome Biol.* 16, 20 (2015).
26. Zhang, D. Y. & Seelig, G. Dynamic DNA nanotechnology using strand-displacement reactions. *Nat. Chem.* 3, 103-113 (2011).
27. Lee, J. H. et al. Highly Multiplexed Subcellular RNA Sequencing in Situ. *Science (80-.)*. 343, 1360-1363 (2014).
28. Ke, R. et al. In situ sequencing for RNA analysis in preserved tissue and cells. *Nat. Methods* 10, 857-60 (2013).
29. Shah, S. et al. Single-molecule RNA detection at depth via hybridization chain reaction and tissue hydrogel embedding and clearing. *Development* In Review, (2016).
30. Bruchez, M. et al. Semiconductor nanocrystals as fluorescent biological labels. *Science* 281, 2013-6 (1998).
31. Fouz, M. F. et al. Bright Fluorescent Nanotags from Bottlebrush Polymers with DNA-Tipped Bristles. *ACS Cent. Sci.* 1, 431-438 (2015).
32. Steward, O., Wallace, C. S., Lyford, G. L. & Worley, P. F. Synaptic activation causes the mRNA for the leg Arc to localize selectively near activated postsynaptic sites on dendrites. *Neuron* 21, 741-751 (1998).
33. Buckley, P. T. et al. Cytoplasmic Intron Sequence-Retaining Transcripts Can Be Dendritically Targeted via ID Element Retrotransposons. *Neuron* 69, 877-884 (2011).
34. Steward, 0. & Schuman, E. M. Compartmentalized synthesis and degradation of proteins in neurons. *Neuron* 40, 347-359 (2003).
35. Buxbaum, A. R., Wu, B. & Singer, R. H. Single-Actin mRNA Detection in Neurons Reveals a Mechanism for Regulating Its Translatability. *Science (80-.)*. 343, 419-422 (2014).
36. Jung, H., Yoon, B. C. & Holt, C. E. Axonal mRNA localization and local protein synthesis in nervous system assembly, maintenance and repair. *Nat. Rev. Neurosci.* 13, 308-24 (2012).
37. Raj, A. & Tyagi, S. *Detection of individual endogenous RNA transcripts in situ using multiple singly labeled probes. Methods in enzymology* 472, (Elsevier Inc., 2010).
38. Schindelin, J. et al. Fiji: an open-source platform for biological-image analysis. *Nat. Methods* 9, 676-82 (2012).
39. Thévenaz, P., Ruttimann, U. E. & Unser, M. A pyramid approach to subpixel registration based on intensity. *IEEE Trans. Image Process.* 7, 27-41 (1998).

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for in situ genomic and transcriptomic assessment of target nucleic acids present in a biological sample comprising the steps of:
   a) treating the biological sample with a small molecule linker comprising a chemical reactive group capable of covalently binding at least one target nucleic acid and a chemical group that can be incorporated into the a swellable material;
   b) permeating the biological sample with a composition comprising precursors of a swellable material;
   c) initiating polymerization of the precursors to form a swellable material, wherein the small molecule linker is bound to the at least one target nucleic acid in the biological sample and to the swellable material;
   d). subjecting the biological sample to a physical disruption method;
   e). swelling the swellable material to form an expanded biological sample;
   f). providing at least one oligonucleotide complementary to the at least one target nucleic acid, wherein the at least one oligonucleotide hybridizes to the at least one target nucleic acid; and
   g). genomically or transcriptomically assessing the expanded biological sample.

2. The method according to claim 1, wherein the small molecule linker is labeled.

3. The method according to claim 2, wherein the expanded biological sample expresses one or more labeled target nucleic acids.

4. The method according to claim 1, wherein the at least one oligonucleotide is labeled.

5. The method according to claim 1, wherein the at least one target nucleic acid is anchored to the swellable material.

6. The method according to claim 1, wherein the physical disruption method is an enzymatic digestion.

7. The method according to claim 1, wherein the target nucleic acids are DNA and/or RNA.

8. The method according to claim 1, further comprising the additional step of buffering the expanded sample.

9. The method according to claim 8, further comprising the additional step of re-embedding the buffered expanded biological sample in a non-swellable material.

10. The method according to claim 9, further comprising the step of removing the at least one oligonucleotide complementary to the at least one target nucleic acid.

11. The method according to claim 10, wherein the steps of providing at least one oligonucleotide, genomically or transcriptomically assessing the expanded biological sample and removing the at least one oligonucleotide are repeated so as to allow serial or sequential genomic or transcriptomic assessments of the expanded biological sample.

12. The method of claim 10, wherein removing the at least one oligonucleotide which is hybridized to the at least one target nucleic acid comprises formamide and high temperatures.

13. The method of claim 10, wherein removing the at least one oligonucleotide which is hybridized to the at least one target nucleic acid comprises endonucleases that specifically digest the at least one oligonucleotide.

* * * * *

UNITED STATES PATENT AND TRADEMARK OFFICE
CERTIFICATE OF CORRECTION

PATENT NO. : 10,364,457 B2
APPLICATION NO. : 15/229539
DATED : July 30, 2019
INVENTOR(S) : Wassie et al.

Page 1 of 1

It is certified that error appears in the above-identified patent and that said Letters Patent is hereby corrected as shown below:

In the Specification

In Column 1, Lines 10-14, delete:
"This invention was made with government support under 5-DPI-NS087724 awarded by NIH, Hertz Foundation, ODGE Lemelson & Viterbi, 5-DPI-N S087724 awarded by NIH and NSF. The government has certain rights in the invention."

And insert:
-- This invention was made with government support under HG005550, HG008525, and NS087724 awarded by the National Institutes of Health, and DGE1144152 awarded by the National Science Foundation. The government has certain rights in the invention. --

Signed and Sealed this
Ninth Day of December, 2025

John A. Squires
*Director of the United States Patent and Trademark Office*

SEQUENCE LISTING

```
<160> NUMBER OF SEQ ID NOS: 412

<210> SEQ ID NO 1
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 1
gaggagggca gcaaacggga agagtcttcc tttacgtaat ctcgcccttg ctcaccat      58

<210> SEQ ID NO 2
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 2
gaggagggca gcaaacggga agagtcttcc tttacgtaat caccacccg gtgaacag       58
```

```
<210> SEQ ID NO 3
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 3
gaggagggca gcaaacggga agagtcttcc tttacgtaat tccagctcga ccaggatg      58

<210> SEQ ID NO 4
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 4
gaggagggca gcaaacggga agagtcttcc tttacgtaat tgtggccgtt tacgtcgc      58

<210> SEQ ID NO 5
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 5
gaggagggca gcaaacggga agagtcttcc tttacgtaat ctcgccggac acgctgaa      58

<210> SEQ ID NO 6
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 6
gaggagggca gcaaacggga agagtcttcc tttacgtaat taggtggcat cgccctcg      58

<210> SEQ ID NO 7
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 7
gaggagggca gcaaacggga agagtcttcc tttacgtaat acttcagggt cagcttgc      58

<210> SEQ ID NO 8
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

```
<400> SEQUENCE: 8
gaggagggca gcaaacggga agagtcttcc tttacgtaat cttgccggtg gtgcagat        58

<210> SEQ ID NO 9
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 9
gaggagggca gcaaacggga agagtcttcc tttacgtaat gtgggccagg gcacgggc        58

<210> SEQ ID NO 10
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 10
gaggagggca gcaaacggga agagtcttcc tttacgtaat agccgaaggt ggtcacga        58

<210> SEQ ID NO 11
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 11
gaggagggca gcaaacggga agagtcttcc tttacgtaat ggcgaagcac tgcaggcc        58

<210> SEQ ID NO 12
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 12
gaggagggca gcaaacggga agagtcttcc tttacgtaat ttcatgtggt cggggtag        58

<210> SEQ ID NO 13
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 13
gaggagggca gcaaacggga agagtcttcc tttacgtaat acttgaagaa gtcgtgct        58

<210> SEQ ID NO 14
<211> LENGTH: 58
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic probe"

<400> SEQUENCE: 14
gaggagggca gcaaacggga agagtcttcc tttacgtaat gtagccttcg ggcatggc        58

<210> SEQ ID NO 15
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 15
gaggagggca gcaaacggga agagtcttcc tttacgtaat aagatggtgc gctcctgg        58

<210> SEQ ID NO 16
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 16
gaggagggca gcaaacggga agagtcttcc tttacgtaat agttgccgtc gtccttga        58

<210> SEQ ID NO 17
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 17
gaggagggca gcaaacggga agagtcttcc tttacgtaat cacctcggcg cgggtctt        58

<210> SEQ ID NO 18
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 18
gaggagggca gcaaacggga agagtcttcc tttacgtaat agggtgtcgc cctcgaac        58

<210> SEQ ID NO 19
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 19
gaggagggca gcaaacggga agagtcttcc tttacgtaat tcagctcgat gcggttca        58
```

<210> SEQ ID NO 20
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 20
gaggagggca gcaaacggga agagtcttcc tttacgtaat ctccttgaag tcgatgcc        58

<210> SEQ ID NO 21
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 21
gaggagggca gcaaacggga agagtcttcc tttacgtaat tgccccagga tgttgccg        58

<210> SEQ ID NO 22
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 22
gaggagggca gcaaacggga agagtcttcc tttacgtaat tgtagttgta ctccagct        58

<210> SEQ ID NO 23
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 23
gaggagggca gcaaacggga agagtcttcc tttacgtaat gatatagacg ttgtggct        58

<210> SEQ ID NO 24
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 24
gaggagggca gcaaacggga agagtcttcc tttacgtaat ttcttctgct tgtcggcc        58

<210> SEQ ID NO 25
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 25
gaggagggca gcaaacggga agagtcttcc tttacgtaat tgaagttcac cttgatgc         58

<210> SEQ ID NO 26
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 26
gaggagggca gcaaacggga agagtcttcc tttacgtaat ctcgatgttg tggcggat         58

<210> SEQ ID NO 27
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 27
gaggagggca gcaaacggga agagtcttcc tttacgtaat gcgagctgca cgctgccg         58

<210> SEQ ID NO 28
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 28
gaggagggca gcaaacggga agagtcttcc tttacgtaat tgttctgctg gtagtggt         58

<210> SEQ ID NO 29
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 29
gaggagggca gcaaacggga agagtcttcc tttacgtaat ggggccgtcg ccgatggg         58

<210> SEQ ID NO 30
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 30
gaggagggca gcaaacggga agagtcttcc tttacgtaat tggttgtcgg gcagcagc         58

<210> SEQ ID NO 31
<211> LENGTH: 58
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 31
gaggagggca gcaaacggga agagtcttcc tttacgtaat cggactggta gctcaggt       58

<210> SEQ ID NO 32
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 32
gaggagggca gcaaacggga agagtcttcc tttacgtaat gttggggtct ttgctcag       58

<210> SEQ ID NO 33
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 33
gaggagggca gcaaacggga agagtcttcc tttacgtaat accatgtgat cgcgcttc       58

<210> SEQ ID NO 34
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 34
gaggagggca gcaaacggga agagtcttcc tttacgtaat cggtcacgaa ctccagca       58

<210> SEQ ID NO 35
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 35
gaggagggca gcaaacggga agagtcttcc tttacgtaat gccgagagtg atcccggc       58

<210> SEQ ID NO 36
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 36
gaggagggca gcaaacggga agagtcttcc tttacgtaat tacttgtaca gctcgtcc       58

<210> SEQ ID NO 37
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 37
ttgaaaaatc gagggtgacc tgaaagctca gtccatcctc gtaaatcctc atcaatcatc    60

<210> SEQ ID NO 38
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 38
ccaatgatat ccaaaccagt agaagcattc tttcttgagg agggcagcaa acgggaagag    60

<210> SEQ ID NO 39
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 39
gatgtcagcc attcaccagc taaaagctca gtccatcctc gtaaatcctc atcaatcatc    60

<210> SEQ ID NO 40
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 40
tcatatgtga acatattggt ataagcattc tttcttgagg agggcagcaa acgggaagag    60

<210> SEQ ID NO 41
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 41
atgagaacaa acacgggtgc aaaaagctca gtccatcctc gtaaatcctc atcaatcatc    60

<210> SEQ ID NO 42
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic probe"

<400> SEQUENCE: 42
tctctcatct tcttaagagt aaaagcattc tttcttgagg agggcagcaa acgggaagag     60

<210> SEQ ID NO 43
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 43
tctttatttg accatccaac gaaaagctca gtccatcctc gtaaatcctc atcaatcatc     60

<210> SEQ ID NO 44
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 44
gctcccccag gagaaaatat ccaagcattc tttcttgagg agggcagcaa acgggaagag     60

<210> SEQ ID NO 45
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 45
atgatgctgt acatattgga taaaagctca gtccatcctc gtaaatcctc atcaatcatc     60

<210> SEQ ID NO 46
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 46
acttctggga agtacttgta acaagcattc tttcttgagg agggcagcaa acgggaagag     60

<210> SEQ ID NO 47
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 47
acagccgcca tgccttttgt ctaaagctca gtccatcctc gtaaatcctc atcaatcatc     60

<210> SEQ ID NO 48
<211> LENGTH: 60

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 48
tgttctgagg tgaagaggac caaagcattc tttcttgagg agggcagcaa acgggaagag      60

<210> SEQ ID NO 49
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 49
gctttcttta tggaatagtg acaaagctca gtccatcctc gtaaatcctc atcaatcatc      60

<210> SEQ ID NO 50
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 50
ttgtcggttc caaagccaag cgaagcattc tttcttgagg agggcagcaa acgggaagag      60

<210> SEQ ID NO 51
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 51
tcattgcact ttatcaaaat caaaagctca gtccatcctc gtaaatcctc atcaatcatc      60

<210> SEQ ID NO 52
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 52
tctaaatcag ccggaattat ctaagcattc tttcttgagg agggcagcaa acgggaagag      60

<210> SEQ ID NO 53
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 53
```
tgtttggcat caagaattt tgaaagctca gtccatcctc gtaaatcctc atcaatcatc    60

<210> SEQ ID NO 54
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 54
gcattgacat aaagggaac ataagcattc tttcttgagg agggcagcaa acgggaagag    60

<210> SEQ ID NO 55
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 55
ccgtaaacag tcgtgcctgc ggaaagctca gtccatcctc gtaaatcctc atcaatcatc    60

<210> SEQ ID NO 56
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 56
tccgcaattt cctggattgg ataagcattc tttcttgagg agggcagcaa acgggaagag    60

<210> SEQ ID NO 57
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 57
caaaggttgt atttctcaca taaagctca gtccatcctc gtaaatcctc atcaatcatc    60

<210> SEQ ID NO 58
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 58
ccaccacccc aggcagcatc caaagcattc tttcttgagg agggcagcaa acgggaagag    60

<210> SEQ ID NO 59
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 59
cggtgcttcc gggacatgag caaaagctca gtccatcctc gtaaatcctc atcaatcatc    60

<210> SEQ ID NO 60
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 60
ttggcccttt ctatgccgct gaaagcattc tttcttgagg agggcagcaa acgggaagag    60

<210> SEQ ID NO 61
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 61
ttgtgagggt tccaggtgac tgaaagctca gtccatcctc gtaaatcctc atcaatcatc    60

<210> SEQ ID NO 62
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 62
gcagagcact ggagcagcac gcaagcattc tttcttgagg agggcagcaa acgggaagag    60

<210> SEQ ID NO 63
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 63
ataccctttt ccttgaccag aaaaagctca gtccatcctc gtaaatcctc atcaatcatc    60

<210> SEQ ID NO 64
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 64
cctgcacaca tctggttgca tcaagcattc tttcttgagg agggcagcaa acgggaagag    60

<210> SEQ ID NO 65

```
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 65
cctcgtaaat cctcatcaat catccagtaa accgccaagg aatacagccc ggggagcatc    60

<210> SEQ ID NO 66
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 66
cctcgtaaat cctcatcaat catccagtaa accgccaaca cccacatagg agtccttctg    60

<210> SEQ ID NO 67
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 67
cctcgtaaat cctcatcaat catccagtaa accgccaaca atggggtact tcagggtcag    60

<210> SEQ ID NO 68
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 68
cctcgtaaat cctcatcaat catccagtaa accgccaagg tgccagatct tctccatgtc    60

<210> SEQ ID NO 69
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 69
cctcgtaaat cctcatcaat catccagtaa accgccaatc atcttttcac ggttggcctt    60

<210> SEQ ID NO 70
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 70
```
cctcgtaaat cctcatcaat catccagtaa accgccaatg gctacgtaca tggctggggt    60

<210> SEQ ID NO 71
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 71
cctcgtaaat cctcatcaat catccagtaa accgccaaca atgcctgtgg tacgaccaga    60

<210> SEQ ID NO 72
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 72
cctcgtaaat cctcatcaat catccagtaa accgccaacc tcgtagatgg gcacagtgtg    60

<210> SEQ ID NO 73
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 73
cctcgtaaat cctcatcaat catccagtaa accgccaaat cttcatgagg tagtctgtca    60

<210> SEQ ID NO 74
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 74
cctcgtaaat cctcatcaat catccagtaa accgccaaat ttccctctca gctgtggtgg    60

<210> SEQ ID NO 75
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 75
cctcgtaaat cctcatcaat catccagtaa accgccaatc gaagtctaga gcaacatagc    60

<210> SEQ ID NO 76
<211> LENGTH: 60
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic probe"

<400> SEQUENCE: 76
cctcgtaaat cctcatcaat catccagtaa accgccaata gctcttctcc agggaggaag    60

<210> SEQ ID NO 77
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 77
cctcgtaaat cctcatcaat catccagtaa accgccaacg gaaccgctcg ttgccaatag    60

<210> SEQ ID NO 78
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 78
cctcgtaaat cctcatcaat catccagtaa accgccaaca ggattccata cccaagaagg    60

<210> SEQ ID NO 79
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 79
cctcgtaaat cctcatcaat catccagtaa accgccaatc aacgtcacac ttcatgatgg    60

<210> SEQ ID NO 80
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 80
cctcgtaaat cctcatcaat catccagtaa accgccaagt ggtaccacca gacagcactg    60

<210> SEQ ID NO 81
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 81
cctcgtaaat cctcatcaat catccagtaa accgccaaag agcagtaatc tccttctgca    60
```

```
<210> SEQ ID NO 82
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 82
cctcgtaaat cctcatcaat catccagtaa accgccaatt gcgctcagga ggagcaatga    60

<210> SEQ ID NO 83
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 83
cctcgtaaat cctcatcaat catccagtaa accgccaaaa ggtggacagt gaggccagga    60

<210> SEQ ID NO 84
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 84
cctcgtaaat cctcatcaat catccagtaa accgccaaga ggggccggac tcatcgtact    60

<210> SEQ ID NO 85
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 85
gaggagggca gcaaacggga agagtcttcc tttacgttgc gcagcgatat cgtcatccat    60

<210> SEQ ID NO 86
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 86
gaggagggca gcaaacggga agagtcttcc tttacgttcc attcccacca tcacaccctg    60

<210> SEQ ID NO 87
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

```
<400> SEQUENCE: 87
gaggagggca gcaaacggga agagtcttcc tttacgttta cctctcttgc tctgggcctc    60

<210> SEQ ID NO 88
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 88
gaggagggca gcaaacggga agagtcttcc tttacgttcc cagttggtaa caatgccatg    60

<210> SEQ ID NO 89
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 89
gaggagggca gcaaacggga agagtcttcc tttacgttca cgcagctcat tgtagaaggt    60

<210> SEQ ID NO 90
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 90
gaggagggca gcaaacggga agagtcttcc tttacgtttg aaggtctcaa acatgatctg    60

<210> SEQ ID NO 91
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 91
gaggagggca gcaaacggga agagtcttcc tttacgttca tacagggaca gcacagcctg    60

<210> SEQ ID NO 92
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 92
gaggagggca gcaaacggga agagtcttcc tttacgtttg accccgtctc cggagtccat    60

<210> SEQ ID NO 93
<211> LENGTH: 60
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic probe"

<400> SEQUENCE: 93
gaggagggca gcaaacggga agagtcttcc tttacgttgg atggcgtgag ggagagcata    60

<210> SEQ ID NO 94
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 94
gaggagggca gcaaacggga agagtcttcc tttacgttaa gctgtagcca cgctcggtca    60

<210> SEQ ID NO 95
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 95
gaggagggca gcaaacggga agagtcttcc tttacgttag cttctctttg atgtcacgca    60

<210> SEQ ID NO 96
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 96
gaggagggca gcaaacggga agagtcttcc tttacgttga tgcggcagtg gccatctcct    60

<210> SEQ ID NO 97
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 97
gaggagggca gcaaacggga agagtcttcc tttacgttat gacctggccg tcaggcagct    60

<210> SEQ ID NO 98
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 98
gaggagggca gcaaacggga agagtcttcc tttacgttgg ctggaaaaga gcctcagggc    60
```

```
<210> SEQ ID NO 99
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 99
gaggagggca gcaaacggga agagtcttcc tttacgtttt gaatgtagtt tcatggatgc      60

<210> SEQ ID NO 100
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 100
gaggagggca gcaaacggga agagtcttcc tttacgtttt ggcatagagg tctttacgga      60

<210> SEQ ID NO 101
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 101
gaggagggca gcaaacggga agagtcttcc tttacgttct gtcagcaatg cctgggtaca      60

<210> SEQ ID NO 102
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 102
gaggagggca gcaaacggga agagtcttcc tttacgtttt gatcttcatg gtgctaggag      60

<210> SEQ ID NO 103
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 103
gaggagggca gcaaacggga agagtcttcc tttacgttga gccaccgatc cacacagagt      60

<210> SEQ ID NO 104
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

<400> SEQUENCE: 104
gaggagggca gcaaacggga agagtcttcc tttacgtttg cttgctgatc cacatctgct    60

<210> SEQ ID NO 105
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 105
gaggagggca gcaaacggga agagtcttcc tttacgttta gaagcacttg cggtgcacga    60

<210> SEQ ID NO 106
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 106
gaggagggca gcaaacggga agagtcttcc tttacgttta gaagcacttg cggtgcacga    60

<210> SEQ ID NO 107
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 107
gggctgtgtt ccagaggggg cgaagcattc tttcttgagg agggcagcaa acgggaagag    60

<210> SEQ ID NO 108
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 108
gtgtccgtgt tgacaatcac agaagcattc tttcttgagg agggcagcaa acgggaagag    60

<210> SEQ ID NO 109
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 109
tcctcatact ccatctcccc ctaagcattc tttcttgagg agggcagcaa acgggaagag    60

<210> SEQ ID NO 110
<211> LENGTH: 60
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 110
gtgccacctg cgatgctgaa gcaagcattc tttcttgagg agggcagcaa acgggaagag    60

<210> SEQ ID NO 111
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 111
ggaatgatct tggtgataaa gaaagcattc tttcttgagg agggcagcaa acgggaagag    60

<210> SEQ ID NO 112
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 112
aacaggatgc tgtcgttgac ccaagcattc tttcttgagg agggcagcaa acgggaagag    60

<210> SEQ ID NO 113
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 113
agggcctcca ctgcagctga ataagcattc tttcttgagg agggcagcaa acgggaagag    60

<210> SEQ ID NO 114
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 114
gctgggggtt tccggcgcat gaaagcattc tttcttgagg agggcagcaa acgggaagag    60

<210> SEQ ID NO 115
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 115
ctgaagccaa gtcctttagg ccaagcattc tttcttgagg agggcagcaa acgggaagag    60
```

<210> SEQ ID NO 116
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 116
acgtagatgc tattatctcc agaagcattc tttcttgagg agggcagcaa acgggaagag    60

<210> SEQ ID NO 117
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 117
ccgatctgca acctgccatc ctaagcattc tttcttgagg agggcagcaa acgggaagag    60

<210> SEQ ID NO 118
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 118
tcctcatgca tgacatcctc taaagcattc tttcttgagg agggcagcaa acgggaagag    60

<210> SEQ ID NO 119
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 119
ttggccacct ttaggtacac aaaagcattc tttcttgagg agggcagcaa acgggaagag    60

<210> SEQ ID NO 120
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 120
gaggttgtga tgtctggggg agaagcattc tttcttgagg agggcagcaa acgggaagag    60

<210> SEQ ID NO 121
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic probe"

<400> SEQUENCE: 121
tcggtgccca agtagctgct ataagcattc tttcttgagg agggcagcaa acgggaagag         60

<210> SEQ ID NO 122
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 122
tcttcatctt ggtagcggta ttaaagctca gtccatcctc gtaaatcctc atcaatcatc         60

<210> SEQ ID NO 123
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 123
ggagaattgg cctggttggg gaaaagctca gtccatcctc gtaaatcctc atcaatcatc         60

<210> SEQ ID NO 124
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 124
gttccgttca catatcctgg ggaaagctca gtccatcctc gtaaatcctc atcaatcatc         60

<210> SEQ ID NO 125
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 125
agacctgagt tacccctttc caaaagctca gtccatcctc gtaaatcctc atcaatcatc         60

<210> SEQ ID NO 126
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 126
gatgggtcgt caccgatgtg tgaaagctca gtccatcctc gtaaatcctc atcaatcatc         60

<210> SEQ ID NO 127
<211> LENGTH: 60

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 127
aggcggccat cctgggctgc agaaagctca gtccatcctc gtaaatcctc atcaatcatc    60

<210> SEQ ID NO 128
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 128
gtcacctccc ggacatccac ttaaagctca gtccatcctc gtaaatcctc atcaatcatc    60

<210> SEQ ID NO 129
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 129
tagaggcgaa cgatggaacc cgaaagctca gtccatcctc gtaaatcctc atcaatcatc    60

<210> SEQ ID NO 130
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 130
ttgataagct tgatctctat gaaaagctca gtccatcctc gtaaatcctc atcaatcatc    60

<210> SEQ ID NO 131
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 131
atgtgctggt tcccaacgcc ccaaagctca gtccatcctc gtaaatcctc atcaatcatc    60

<210> SEQ ID NO 132
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 132
```
tgggcagcgc ctccttcgat gaaaagctca gtccatcctc gtaaatcctc atcaatcatc    60

<210> SEQ ID NO 133
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 133
cccacactgt tgaccgccag gaaaagctca gtccatcctc gtaaatcctc atcaatcatc    60

<210> SEQ ID NO 134
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 134
tcatatgtgt tcttcagggc tgaaagctca gtccatcctc gtaaatcctc atcaatcatc    60

<210> SEQ ID NO 135
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 135
tagctgtcac tcaggtaggc ataaagctca gtccatcctc gtaaatcctc atcaatcatc    60

<210> SEQ ID NO 136
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 136
ctgatctcat tgtccaggtg ctaaagctca gtccatcctc gtaaatcctc atcaatcatc    60

<210> SEQ ID NO 137
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 137
gaggagggca gcaaacggga agagtcttcc tttacgaacg ggtgcaggtg atggtagcca    60

<210> SEQ ID NO 138
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 138
cctcgtaaat cctcatcaat catccagtaa accgccaatc ctcaaagagc tggtactctt    60

<210> SEQ ID NO 139
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 139
gaggagggca gcaaacggga agagtcttcc tttacgaaac agagaaggct ccctttccca    60

<210> SEQ ID NO 140
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 140
cctcgtaaat cctcatcaat catccagtaa accgccaacc agccagcacc ttcacacacc    60

<210> SEQ ID NO 141
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 141
gaggagggca gcaaacggga agagtcttcc tttacgaaat aatcttggca gcatactcct    60

<210> SEQ ID NO 142
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 142
cctcgtaaat cctcatcaat catccagtaa accgccaatg atctctggct gaaagcttct    60

<210> SEQ ID NO 143
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 143
gaggagggca gcaaacggga agagtcttcc tttacgaacg ggcctcacgc tccagcttct    60

<210> SEQ ID NO 144

```
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 144
cctcgtaaat cctcatcaat catccagtaa accgccaaat attggggtgc ttcaacaagc      60

<210> SEQ ID NO 145
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 145
gaggagggca gcaaacggga agagtcttcc tttacgaaga gatgctgtca tggagtcgga      60

<210> SEQ ID NO 146
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 146
cctcgtaaat cctcatcaat catccagtaa accgccaatc gaagataagg tagtggtgcc      60

<210> SEQ ID NO 147
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 147
gaggagggca gcaaacggga agagtcttcc tttacgaaaa cagttcccca ccagtaacca      60

<210> SEQ ID NO 148
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 148
cctcgtaaat cctcatcaat catccagtaa accgccaact gtaatactcc cgggccacaa      60

<210> SEQ ID NO 149
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 149
```
gaggagggca gcaaacggga agagtcttcc tttacgaaat acagtggctg gcatcagctt    60

<210> SEQ ID NO 150
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic probe"

<400> SEQUENCE: 150
cctcgtaaat cctcatcaat catccagtaa accgccaaca gtgtagcaca gcctccaaga    60

<210> SEQ ID NO 151
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic probe"

<400> SEQUENCE: 151
gaggagggca gcaaacggga agagtcttcc tttacgaacg atgcaccacc cccatctggt    60

<210> SEQ ID NO 152
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic probe"

<400> SEQUENCE: 152
cctcgtaaat cctcatcaat catccagtaa accgccaagc cagcaacaga ttctcaggct    60

<210> SEQ ID NO 153
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic probe"

<400> SEQUENCE: 153
gaggagggca gcaaacggga agagtcttcc tttacgaaac agcagcgccc ttgagcttcg    60

<210> SEQ ID NO 154
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic probe"

<400> SEQUENCE: 154
cctcgtaaat cctcatcaat catccagtaa accgccaatc tatggccagg ccaaagtctg    60

<210> SEQ ID NO 155
<211> LENGTH: 60
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic probe"

<400> SEQUENCE: 155
gaggagggca gcaaacggga agagtcttcc tttacgaaca tgcctgctgc tcccctcca    60

<210> SEQ ID NO 156
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 156
cctcgtaaat cctcatcaat catccagtaa accgccaaag gtatccaggt gtccctgcga    60

<210> SEQ ID NO 157
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 157
gaggagggca gcaaacggga agagtcttcc tttacgaatc cttcctcagc acttctgggg    60

<210> SEQ ID NO 158
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 158
cctcgtaaat cctcatcaat catccagtaa accgccaagc ccacaggtcc acgggcttcc    60

<210> SEQ ID NO 159
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 159
gaggagggca gcaaacggga agagtcttcc tttacgaaaa gatatacagg atgacgccac    60

<210> SEQ ID NO 160
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 160
cctcgtaaat cctcatcaat catccagtaa accgccaatc atcccagaac gggggatacc    60

```
<210> SEQ ID NO 161
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 161
gaggagggca gcaaacggga agagtcttcc tttacgaatg ctggtacagg cgatgctggt    60

<210> SEQ ID NO 162
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 162
cctcgtaaat cctcatcaat catccagtaa accgccaaga tgggaaatca taggcaccag    60

<210> SEQ ID NO 163
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 163
gaggagggca gcaaacggga agagtcttcc tttacgaagg ggtgacggtg tcccattctg    60

<210> SEQ ID NO 164
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 164
cctcgtaaat cctcatcaat catccagtaa accgccaaag catcttattg atcagatcct    60

<210> SEQ ID NO 165
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 165
gaggagggca gcaaacggga agagtcttcc tttacgaaat gcgtttggac gggttgatgg    60

<210> SEQ ID NO 166
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

<400> SEQUENCE: 166
cctcgtaaat cctcatcaat catccagtaa accgccaaca tgggtgcttg agagcctcag    60

<210> SEQ ID NO 167
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 167
gaggagggca gcaaacggga agagtcttcc tttacgaagc cacggtggag cggtgcgaga    60

<210> SEQ ID NO 168
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 168
cctcgtaaat cctcatcaat catccagtaa accgccaatc cacggtctcc tgtctgtgca    60

<210> SEQ ID NO 169
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 169
gaggagggca gcaaacggga agagtcttcc tttacgaact ggcattgaac ttcttcaggc    60

<210> SEQ ID NO 170
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 170
cctcgtaaat cctcatcaat catccagtaa accgccaagt ggtgaggatg gctcccttca    60

<210> SEQ ID NO 171
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 171
gaggagggca gcaaacggga agagtcttcc tttacgaaga gaagttcctg gtggccagca    60

<210> SEQ ID NO 172
<211> LENGTH: 60
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic probe"

<400> SEQUENCE: 172
cctcgtaaat cctcatcaat catccagtaa accgccaatt cttcttgttt cctccgctct      60

<210> SEQ ID NO 173
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 173
gaggagggca gcaaacggga agagtcttcc tttacgaatc agaagattcc ttcacaccat      60

<210> SEQ ID NO 174
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 174
cctcgtaaat cctcatcaat catccagtaa accgccaatc ttcgtcctca atggtggtgt      60

<210> SEQ ID NO 175
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 175
gaggagggca gcaaacggga agagtcttcc tttacgaaat ttcctgtttg cgcactttgg      60

<210> SEQ ID NO 176
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 176
cctcgtaaat cctcatcaat catccagtaa accgccaagc ttcgatcagc tgctctgtca      60

<210> SEQ ID NO 177
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 177
gaggagggca gcaaacggga agagtcttcc tttacgaaga ctcaaagtct ccattgctta      60
```

<210> SEQ ID NO 178
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 178
cctcgtaaat cctcatcaat catccagtaa accgccaagt cattccaggg tcgcacatct    60

<210> SEQ ID NO 179
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 179
gaggagggca gcaaacggga agagtcttcc tttacgaacc cagggcctct ggttcaaagg    60

<210> SEQ ID NO 180
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 180
cctcgtaaat cctcatcaat catccagtaa accgccaacg atgaaagtcc aggccctcca    60

<210> SEQ ID NO 181
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 181
gaggagggca gcaaacggga agagtcttcc tttacgaaga ccacaggttt tcaaaataga    60

<210> SEQ ID NO 182
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 182
cctcgtaaat cctcatcaat catccagtaa accgccaaat ggtggtgtgc acgggcttgc    60

<210> SEQ ID NO 183
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 183
gaggagggca gcaaacggga agagtcttcc tttacgaaat caggtggatg tgagggttca    60

<210> SEQ ID NO 184
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 184
cctcgtaaat cctcatcaat catccagtaa accgccaaat ataggcgatg caggctgact    60

<210> SEQ ID NO 185
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 185
cttcttcacc ttttgaaacc ataagcattc tttcttgagg agggcagcaa acgggaagag    60

<210> SEQ ID NO 186
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 186
ccatatgaac tttaaatctc ataagcattc tttcttgagg agggcagcaa acgggaagag    60

<210> SEQ ID NO 187
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 187
cttcaccttc accttcaatt tcaagcattc tttcttgagg agggcagcaa acgggaagag    60

<210> SEQ ID NO 188
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 188
cacctttagt aactttcaat ttaagcattc tttcttgagg agggcagcaa acgggaagag    60

<210> SEQ ID NO 189
<211> LENGTH: 60
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 189
catacataaa ttgtggtgac aaaagcattc tttcttgagg agggcagcaa acgggaagag      60

<210> SEQ ID NO 190
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 190
ttaaataatc tggaatatca gcaagcattc tttcttgagg agggcagcaa acgggaagag      60

<210> SEQ ID NO 191
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 191
tcaaaattca taactctttc ccaagcattc tttcttgagg agggcagcaa acgggaagag      60

<210> SEQ ID NO 192
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 192
ctctcaattt aactttataa ataagcattc tttcttgagg agggcagcaa acgggaagag      60

<210> SEQ ID NO 193
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 193
ccatagtttt tttttgcata acaagcattc tttcttgagg agggcagcaa acgggaagag      60

<210> SEQ ID NO 194
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 194
tcaatctttg tttaatttca ccaagcattc tttcttgagg agggcagcaa acgggaagag      60
```

<210> SEQ ID NO 195
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 195
taatattaac attataagca ccaagcattc tttcttgagg agggcagcaa acgggaagag    60

<210> SEQ ID NO 196
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 196
tttcatattg ttcaacaata gtaagcattc tttcttgagg agggcagcaa acgggaagag    60

<210> SEQ ID NO 197
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 197
attctttaat aatagccata ttaaagctca gtccatcctc gtaaatcctc atcaatcatc    60

<210> SEQ ID NO 198
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 198
attcatgacc attaactgaa ccaaagctca gtccatcctc gtaaatcctc atcaatcatc    60

<210> SEQ ID NO 199
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 199
cagtttgagt accttcatat ggaaagctca gtccatcctc gtaaatcctc atcaatcatc    60

<210> SEQ ID NO 200
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic probe"

<400> SEQUENCE: 200
tatcccaagc aaatggtaat ggaaagctca gtccatcctc gtaaatcctc atcaatcatc     60

<210> SEQ ID NO 201
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 201
gatgtttaac ataagctttt gaaaagctca gtccatcctc gtaaatcctc atcaatcatc     60

<210> SEQ ID NO 202
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 202
ttaaaacctt ctggaaatga caaaagctca gtccatcctc gtaaatcctc atcaatcatc     60

<210> SEQ ID NO 203
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 203
gagtaacagt aacaacacca ccaaagctca gtccatcctc gtaaatcctc atcaatcatc     60

<210> SEQ ID NO 204
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 204
gaccatctga tggaaaatta gtaaagctca gtccatcctc gtaaatcctc atcaatcatc     60

<210> SEQ ID NO 205
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 205
ttctttctga tgaagcttcc caaaagctca gtccatcctc gtaaatcctc atcaatcatc     60

<210> SEQ ID NO 206
<211> LENGTH: 60

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 206
gtaattgaac tggttttta gcaaagctca gtccatcctc gtaaatcctc atcaatcatc       60

<210> SEQ ID NO 207
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 207
tcattatgtg aagtaatatc caaaagctca gtccatcctc gtaaatcctc atcaatcatc       60

<210> SEQ ID NO 208
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 208
atttatataa ttcatccata ccaaagctca gtccatcctc gtaaatcctc atcaatcatc       60

<210> SEQ ID NO 209
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 209
aataccgcta ccaagatgaa gaaaagctca gtccatcctc gtaaatcctc atcaatcatc       60

<210> SEQ ID NO 210
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 210
tccccaacca ggccaattct ccaaagctca gtccatcctc gtaaatcctc atcaatcatc       60

<210> SEQ ID NO 211
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 211
``` cccaggata tgtgaacgga acaaagctca gtccatcctc gtaaatcctc atcaatcatc    60

<210> SEQ ID NO 212
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 212
tggaaagggg taactcaggt ctaaagctca gtccatcctc gtaaatcctc atcaatcatc    60

<210> SEQ ID NO 213
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 213
cacacatcgg tgacgaccca tcaaagctca gtccatcctc gtaaatcctc atcaatcatc    60

<210> SEQ ID NO 214
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 214
ctgcagccca ggatggccgc ctaaagctca gtccatcctc gtaaatcctc atcaatcatc    60

<210> SEQ ID NO 215
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 215
aagtggatgt ccgggaggtg acaaagctca gtccatcctc gtaaatcctc atcaatcatc    60

<210> SEQ ID NO 216
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 216
cgggttccat cgttcgcctc taaagctca gtccatcctc gtaaatcctc atcaatcatc    60

<210> SEQ ID NO 217
<211> LENGTH: 60
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic probe"

<400> SEQUENCE: 217
tcatagagat caagcttatc aaaaagctca gtccatcctc gtaaatcctc atcaatcatc    60

<210> SEQ ID NO 218
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 218
ggggcgttgg gaaccagcac ataaagctca gtccatcctc gtaaatcctc atcaatcatc    60

<210> SEQ ID NO 219
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 219
tcatcgaagg aggcgctgcc caaaagctca gtccatcctc gtaaatcctc atcaatcatc    60

<210> SEQ ID NO 220
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 220
tcctggcggt caacagtgtg ggaaagctca gtccatcctc gtaaatcctc atcaatcatc    60

<210> SEQ ID NO 221
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 221
cagccctgaa gaacacatat gaaaagctca gtccatcctc gtaaatcctc atcaatcatc    60

<210> SEQ ID NO 222
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 222
atgcctacct gagtgacagc taaaagctca gtccatcctc gtaaatcctc atcaatcatc    60

<210> SEQ ID NO 223
```

```
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 223
agcacctgga caatgagatc agaaagctca gtccatcctc gtaaatcctc atcaatcatc    60

<210> SEQ ID NO 224
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 224 cgcccctct ggaacacagc ccaagcattc tttcttgagg agggcagcaa acgggaagag    60

<210> SEQ ID NO 225
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 225
ctgtgattgt caacacggac acaagcattc tttcttgagg agggcagcaa acgggaagag    60

<210> SEQ ID NO 226
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 226 aggggagat ggagtatgag gaaagcattc tttcttgagg agggcagcaa acgggaagag    60

<210> SEQ ID NO 227
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 227
gcttcagcat cgcaggtggc acaagcattc tttcttgagg agggcagcaa acgggaagag    60

<210> SEQ ID NO 228
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 228
```
tctttatcac caagatcatt ccaagcattc tttcttgagg agggcagcaa acgggaagag    60

<210> SEQ ID NO 229
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 229
gggtcaacga cagcatcctg ttaagcattc tttcttgagg agggcagcaa acgggaagag    60

<210> SEQ ID NO 230
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 230
attcagctgc agtggaggcc ctaagcattc tttcttgagg agggcagcaa acgggaagag    60

<210> SEQ ID NO 231
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 231
tcatgcgccg gaaaccccca gcaagcattc tttcttgagg agggcagcaa acgggaagag    60

<210> SEQ ID NO 232
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 232
ggcctaaagg acttggcttc agaagcattc tttcttgagg agggcagcaa acgggaagag    60

<210> SEQ ID NO 233
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 233
ctggagataa tagcatctac gtaagcattc tttcttgagg agggcagcaa acgggaagag    60

<210> SEQ ID NO 234
<211> LENGTH: 60
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic probe"

<400> SEQUENCE: 234
aggatggcag gttgcagatc ggaagcattc tttcttgagg agggcagcaa acgggaagag      60

<210> SEQ ID NO 235
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 235
tagaggatgt catgcatgag gaaagcattc tttcttgagg agggcagcaa acgggaagag      60

<210> SEQ ID NO 236
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 236
ttgtgtacct aaaggtggcc aaaagcattc tttcttgagg agggcagcaa acgggaagag      60

<210> SEQ ID NO 237
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 237
ctcccccaga catcacaacc tcaagcattc tttcttgagg agggcagcaa acgggaagag      60

<210> SEQ ID NO 238
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 238
atagcagcta cttgggcacc gaaagcattc tttcttgagg agggcagcaa acgggaagag      60

<210> SEQ ID NO 239
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 239
atggtcttac cagtcagagt                                                  20
```

```
<210> SEQ ID NO 240
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 240
gacattctcg atggtgtcac                                                   20

<210> SEQ ID NO 241
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 241
gggatgcctt ccttatcttg                                                   20

<210> SEQ ID NO 242
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 242
atcttccagc tgttttccag                                                   20

<210> SEQ ID NO 243
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 243
cagtgagtgt cttcacgaag                                                   20

<210> SEQ ID NO 244
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 244
tcctggatct ttgctttgac                                                   20

<210> SEQ ID NO 245
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

<400> SEQUENCE: 245
cagggtagac tctttctgga                                              20

<210> SEQ ID NO 246
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 246
cttcacgaag atctgcatcc                                              20

<210> SEQ ID NO 247
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 247
tcttggatct ttgccttgac                                              20

<210> SEQ ID NO 248
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 248
cagtgagtgt cttcacgaag                                              20

<210> SEQ ID NO 249
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 249
tgacgttctc gatagtgtca                                              20

<210> SEQ ID NO 250
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 250
tccttgtctt ggatctttgc                                              20

<210> SEQ ID NO 251
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic probe"

<400> SEQUENCE: 251
cagggtagac tctttctgga                                                   20

<210> SEQ ID NO 252
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 252
cttcacgaag atctgcatcc                                                   20

<210> SEQ ID NO 253
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 253
agagtgatgg tcttaccagt                                                   20

<210> SEQ ID NO 254
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 254
tcttggatct ttgccttgac                                                   20

<210> SEQ ID NO 255
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 255
cttcacgaag atctgcatcc                                                   20

<210> SEQ ID NO 256
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 256
agagtgatgg tcttaccagt                                                   20
```

<210> SEQ ID NO 257
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 257
tcttggatct ttgccttgac                                              20

<210> SEQ ID NO 258
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 258
tgtttcccag caaagatcaa                                              20

<210> SEQ ID NO 259
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 259
cttcacgaag atctgcatcc                                              20

<210> SEQ ID NO 260
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 260
agagtgatgg tcttaccagt                                              20

<210> SEQ ID NO 261
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 261
tcttggatct ttgccttgac                                              20

<210> SEQ ID NO 262
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

```
<400> SEQUENCE: 262
tgtttcccag caaagatcaa                                              20

<210> SEQ ID NO 263
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 263
cttcacgaag atctgcatcc                                              20

<210> SEQ ID NO 264
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 264
agagtgatgg tcttaccagt                                              20

<210> SEQ ID NO 265
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 265
tcttggatct ttgccttgac                                              20

<210> SEQ ID NO 266
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 266
tgtttcccag caaagatcaa                                              20

<210> SEQ ID NO 267
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 267
gacattctcg atggtgtcac                                              20

<210> SEQ ID NO 268
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 268
gggatgcctt ccttatcttg                                            20

<210> SEQ ID NO 269
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 269
tgtttcccag caaagatcaa                                            20

<210> SEQ ID NO 270
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 270
agagtggact ctttctggat                                            20

<210> SEQ ID NO 271
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 271
atctggtcta ccgtgaagtt                                            20

<210> SEQ ID NO 272
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 272
ttggccttct tgtccatgat                                            20

<210> SEQ ID NO 273
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 273
gtatcagtga agcgtgtctc                                            20
```

```
<210> SEQ ID NO 274
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 274
ttgacttgat ggtgatgcaa                                                     20

<210> SEQ ID NO 275
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 275
ctcgtagaag agggagatgg                                                     20

<210> SEQ ID NO 276
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 276
tccttgctct gcttgatgaa                                                     20

<210> SEQ ID NO 277
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 277
gggagtcaat gaggttgatg                                                     20

<210> SEQ ID NO 278
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 278
cggtccatct tgttcatcat                                                     20

<210> SEQ ID NO 279
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic probe"

<400> SEQUENCE: 279
gtggagatga tgacgttcac                                        20

<210> SEQ ID NO 280
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 280
gtaccgagga caggatcgat                                        20

<210> SEQ ID NO 281
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 281
caaactgctt cagggtgaag                                        20

<210> SEQ ID NO 282
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 282
aacttggcca catacatctc                                        20

<210> SEQ ID NO 283
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 283
atgtcctcta ctttcttggc                                        20

<210> SEQ ID NO 284
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 284
ttcatgatcg catcaaacac                                        20

<210> SEQ ID NO 285
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 285
gtccagtttg atgtccagtt                                              20

<210> SEQ ID NO 286
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 286
gatggtgatc atctgcaaca                                              20

<210> SEQ ID NO 287
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 287
tttggggtca cagcttttaa                                              20

<210> SEQ ID NO 288
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 288
gtagaaccga cctttgtcgg                                              20

<210> SEQ ID NO 289
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 289
ccatgatcct gaccttcagg                                              20

<210> SEQ ID NO 290
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 290
```
ttcttcccag gggtatagtt                                              20

<210> SEQ ID NO 291
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 291
tctggattgg cttcaggtag                                              20

<210> SEQ ID NO 292
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 292
ggcccatcat caagattgtt                                              20

<210> SEQ ID NO 293
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 293
gtcttcacca ggaactggtc                                              20

<210> SEQ ID NO 294
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 294
ctgacgctga acttcatcac                                              20

<210> SEQ ID NO 295
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 295
atgatatgct ctcccgactc                                              20

<210> SEQ ID NO 296
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic probe"

<400> SEQUENCE: 296
gactcttcac tgaccgtctc                                            20

<210> SEQ ID NO 297
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 297
cttcatgtac agccggttgt                                            20

<210> SEQ ID NO 298
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 298
tcgcctttat cgatgtcctc                                            20

<210> SEQ ID NO 299
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 299
tgatgtcggt gaggatgttg                                            20

<210> SEQ ID NO 300
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 300
cactgtcctt gatctcgttg                                            20

<210> SEQ ID NO 301
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 301
gtcagcacac tggcatagag                                            20

<210> SEQ ID NO 302
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 302
atctccacaa ggtagatggg                                              20

<210> SEQ ID NO 303
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 303
ggatccagac ccgggtccag                                              20

<210> SEQ ID NO 304
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 304
tactggatgt tgtggtcgcc                                              20

<210> SEQ ID NO 305
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 305
catttgtctc tgtgcggaac                                              20

<210> SEQ ID NO 306
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 306
attttggatc acagcctgtc                                              20

<210> SEQ ID NO 307
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 307
```
gactgccacc attgctgaag                                               20

<210> SEQ ID NO 308
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 308
ctgggaaata ggcaaatcgt                                               20

<210> SEQ ID NO 309
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 309
gacacagccg tagtatctcc                                               20

<210> SEQ ID NO 310
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 310
gtctgaagca catcctgggg                                               20

<210> SEQ ID NO 311
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 311
ggcgatcgtc ctctgtgttc                                               20

<210> SEQ ID NO 312
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 312
tggttccatc aatttttgga                                               20

<210> SEQ ID NO 313
<211> LENGTH: 20
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic probe"

<400> SEQUENCE: 313
ttctcctctc atctcggggt                                                  20

<210> SEQ ID NO 314
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 314
ctccacttcg ttgtgctggg                                                  20

<210> SEQ ID NO 315
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 315
cagttgttga tcttgtccct                                                  20

<210> SEQ ID NO 316
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 316
gattttcgaa agctggacga                                                  20

<210> SEQ ID NO 317
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 317
gttgtctgcg ttacagtctg                                                  20

<210> SEQ ID NO 318
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 318
ggccttggac aggatccctc                                                  20
```

```
<210> SEQ ID NO 319
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 319
cgcaactccc ggatgtaatc                                                 20

<210> SEQ ID NO 320
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 320
ctgcatgcgc tggttggtct                                                 20

<210> SEQ ID NO 321
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 321
gctcggcctc tttgaaggtc                                                 20

<210> SEQ ID NO 322
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 322
agctcgttgt ccatctgcag                                                 20

<210> SEQ ID NO 323
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 323
caccatctcc aggttgtgct                                                 20

<210> SEQ ID NO 324
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

```
-continued

<400> SEQUENCE: 324
tgtatccaca gaaatgcatt                                               20

<210> SEQ ID NO 325
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 325
ggaggatacc gtttccaagt                                               20

<210> SEQ ID NO 326
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 326
gtgagaccac tagaagtgcc                                               20

<210> SEQ ID NO 327
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 327
cataggtcca ggccccgggt                                               20

<210> SEQ ID NO 328
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 328
cagggaccca gaaacaagag                                               20

<210> SEQ ID NO 329
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 329
gggccagttt attgcagtta                                               20

<210> SEQ ID NO 330
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic probe"

<400> SEQUENCE: 330
ctgggcggag caaaatatgt                                              20

<210> SEQ ID NO 331
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 331
tcttcatcgt aaacccacat                                              20

<210> SEQ ID NO 332
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 332
ccggatcaat tgtgactcta                                              20

<210> SEQ ID NO 333
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 333 cctttccat tattccatat                                               20

<210> SEQ ID NO 334
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 334
agaagttagg agctgtccaa                                              20

<210> SEQ ID NO 335
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 335
ccagcaatat catatgctct                                              20
```

```
<210> SEQ ID NO 336
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 336
ttactggcag tttatttcca                                           20

<210> SEQ ID NO 337
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 337
tgttgatcca aagctcttgg                                           20

<210> SEQ ID NO 338
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 338
aactggactt gggccttaaa                                           20

<210> SEQ ID NO 339
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 339
atcattggca tcatcgagtt                                           20

<210> SEQ ID NO 340
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 340
gtcaggataa gcgtacactc                                           20

<210> SEQ ID NO 341
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

```
<400> SEQUENCE: 341
ggaaaacccc atatttgtct                                               20

<210> SEQ ID NO 342
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 342
tttcttgtac tgaagaccca                                               20

<210> SEQ ID NO 343
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 343
ttggtcctga tctgtcataa                                               20

<210> SEQ ID NO 344
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 344
ctccagaaaa cgatgtcgca                                               20

<210> SEQ ID NO 345
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 345
gttaaccatt cctttcgatc                                               20

<210> SEQ ID NO 346
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 346
agctaattgg gcaaccttta                                               20

<210> SEQ ID NO 347
<211> LENGTH: 20
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 347
atgtatcgtg gactagcaga                                                 20

<210> SEQ ID NO 348
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 348
acgctggttg tcatcatata                                                 20

<210> SEQ ID NO 349
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 349
ttcttctcca tccatcaaac                                                 20

<210> SEQ ID NO 350
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 350
cccttgaagt tctttgtaact                                                20

<210> SEQ ID NO 351
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 351
tatgagagga ggtgtcttct                                                 20

<210> SEQ ID NO 352
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 352
tgtatggtat tccctatagt                                                 20
```

```
<210> SEQ ID NO 353
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 353
tcagtttagc agattcagca                                              20

<210> SEQ ID NO 354
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 354
cttcacagga tccgaatcat                                              20

<210> SEQ ID NO 355
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 355
gtggaatgac tctttgacca                                              20

<210> SEQ ID NO 356
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 356
tgctcctatc tgattctgaa                                              20

<210> SEQ ID NO 357
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 357
agtggaggtg gaagactgac                                              20

<210> SEQ ID NO 358
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic probe"

<400> SEQUENCE: 358
aattcaaagc tggatccctt                                          20

<210> SEQ ID NO 359
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 359
caggatcagg cttttgagag                                          20

<210> SEQ ID NO 360
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 360
cttggatttc ttgcttgtga                                          20

<210> SEQ ID NO 361
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 361
tatggaagtc atcactctcc                                          20

<210> SEQ ID NO 362
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 362
gacctagtct ccttgccaag                                          20

<210> SEQ ID NO 363
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 363
ggatattttc catgcagcct                                          20

<210> SEQ ID NO 364
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 364
acaagttgaa gattagccct                                               20

<210> SEQ ID NO 365
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 365
ccttggtctg gaaaaaaagg                                               20

<210> SEQ ID NO 366
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 366
cgagctaagt tcagttccac                                               20

<210> SEQ ID NO 367
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 367
ggccgagcga aaattacata                                               20

<210> SEQ ID NO 368
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 368
cctgtcaaac atgctaggtg                                               20

<210> SEQ ID NO 369
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 369
```
actgccacct ggaaaataaa                                               20

<210> SEQ ID NO 370
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 370
gtgagctcac aagaagagtt                                               20

<210> SEQ ID NO 371
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 371
accagatgac caggtaatgt                                               20

<210> SEQ ID NO 372
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 372
cggtccatga agcatttttg                                               20

<210> SEQ ID NO 373
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 373
tcgccatgag gaacactata                                               20

<210> SEQ ID NO 374
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 374
aatctgcagg catcaattga                                               20

<210> SEQ ID NO 375
<211> LENGTH: 20
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic probe"

<400> SEQUENCE: 375
cctggaaaca gaacattgga                                              20

<210> SEQ ID NO 376
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 376
gcatctgctg tggactttt                                               20

<210> SEQ ID NO 377
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 377
ggctctggaa caagcattta                                              20

<210> SEQ ID NO 378
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 378
tgcagcatct gaaaaccttt                                              20

<210> SEQ ID NO 379
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 379
accggaggct caatttagaa                                              20

<210> SEQ ID NO 380
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 380
caaggttcca agcacaaaac                                              20

<210> SEQ ID NO 381
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 381
acagcttagg gatcttcttg                                                    20

<210> SEQ ID NO 382
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 382
tggcatcaac gttaaaatgt                                                    20

<210> SEQ ID NO 383
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 383
tctacaaggc atcaatctgc                                                    20

<210> SEQ ID NO 384
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 384
aagaacttct ccgagaaacg                                                    20

<210> SEQ ID NO 385
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 385
gccccaagtt atttcatcag                                                    20

<210> SEQ ID NO 386
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 386
```
gcgtttagca caacacaatg                                              20

<210> SEQ ID NO 387
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 387
ggaatgacca acttgtaccc                                              20

<210> SEQ ID NO 388
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 388
caatgcccaa actagacctg                                              20

<210> SEQ ID NO 389
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 389
tcctagtaat ctgcaatgca                                              20

<210> SEQ ID NO 390
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 390
agcaagaaca aaagagcact                                              20

<210> SEQ ID NO 391
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 391
ggtcctctta ctagaatgcc                                              20

<210> SEQ ID NO 392
<211> LENGTH: 20
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic probe"

<400> SEQUENCE: 392
ctgtgtcacc tgttttcagt                                              20

<210> SEQ ID NO 393
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 393
cctttggttc tcggaaaact                                              20

<210> SEQ ID NO 394
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 394
agctggtaaa gacatttccc                                              20

<210> SEQ ID NO 395
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 395
ctctgaaaca ggctgtcttg                                              20

<210> SEQ ID NO 396
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 396
gcccatcttt caagtgacta                                              20

<210> SEQ ID NO 397
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 397
aaccacctaa gttgctaagg                                              20

```
<210> SEQ ID NO 398
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 398
tcgtcttaag tggtcccttc                                              20

<210> SEQ ID NO 399
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 399
atccagaaga gcccatctaa                                              20

<210> SEQ ID NO 400
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 400
acctgtgaca aatgaggaac                                              20

<210> SEQ ID NO 401
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 401
agatgtgttt ctaaggcacg                                              20

<210> SEQ ID NO 402
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 402
acagtgacca caaaaggtta                                              20

<210> SEQ ID NO 403
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
```

```
<400> SEQUENCE: 403
agcaaaggta catggattct                                              20

<210> SEQ ID NO 404
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 404
cagggttttc agatcacaca                                              20

<210> SEQ ID NO 405
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 405
ccccaagtca ttggttaaga                                              20

<210> SEQ ID NO 406
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 406
tcccaacgac agtaattgtt                                              20

<210> SEQ ID NO 407
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 407
cccatacatg cgtgactaat                                              20

<210> SEQ ID NO 408
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 408
caacagcata cccgagacta                                              20

<210> SEQ ID NO 409
<211> LENGTH: 20
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic probe"

<400> SEQUENCE: 409
acagagcaac ataccagtac                                                20

<210> SEQ ID NO 410
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
ggcggtttac tggatgattg atgaggattt acgaggagct cagtccatcc tcgtaaatcc     60
tcatcaatca tcaaatag                                                  78

<210> SEQ ID NO 411
<211> LENGTH: 72
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
cctcgtaaat cctcatcaat catccagtaa accgccgatg attgatgagg atttacgagg     60
atggactgag ct                                                        72

<210> SEQ ID NO 412
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
ctatttgatg attgatgagg atttacgagg atggactgag ct                       42
```